(12) United States Patent
Howell et al.

(10) Patent No.: US 11,644,361 B2
(45) Date of Patent: May 9, 2023

(54) EYEWEAR WITH DETECTION SYSTEM

(71) Applicant: IngenioSpec, LLC, San Jose, CA (US)

(72) Inventors: Thomas A. Howell, San Jose, CA (US);
David Chao, Saratoga, CA (US); C. Douglass Thomas, Saratoga, CA (US);
Peter P. Tong, Mountain View, CA (US)

(73) Assignee: IngenioSpec, LLC, San Jose, CA (US)

( * ) Notice: Subject to any disclaimer, the term of this patent is extended or adjusted under 35 U.S.C. 154(b) by 0 days.

(21) Appl. No.: 17/681,593

(22) Filed: Feb. 25, 2022

(65) Prior Publication Data

US 2022/0178743 A1 Jun. 9, 2022

Related U.S. Application Data

(63) Continuation of application No. 16/703,805, filed on Dec. 4, 2019, now Pat. No. 11,326,941, which is a continuation of application No. 16/426,351, filed on May 30, 2019, now Pat. No. 10,539,459, which is a continuation of application No. 16/102,859, filed on
(Continued)

(51) Int. Cl.
*G01J 1/42* (2006.01)
*G01J 1/02* (2006.01)
*G02C 5/00* (2006.01)
*G02C 11/00* (2006.01)
*G01J 1/44* (2006.01)
*A61B 5/00* (2006.01)

(52) U.S. Cl.
CPC ............. *G01J 1/429* (2013.01); *G01J 1/0238* (2013.01); *G01J 1/0271* (2013.01); *G01J 1/44* (2013.01); *G02C 5/001* (2013.01); *G02C 11/00* (2013.01); *G02C 11/10* (2013.01); *A61B 5/746* (2013.01); *G01J 2001/0257* (2013.01)

(58) Field of Classification Search
CPC ........ G01J 1/429; G01J 1/0238; G01J 1/0271; G01J 1/44; G02C 5/001; G02C 11/00; G02C 11/10
USPC .......................................................... 250/372
See application file for complete search history.

(56) References Cited

U.S. PATENT DOCUMENTS 320,558 A 6/1885 Hull
669,949 A 3/1901 Underwood
(Continued)

FOREIGN PATENT DOCUMENTS

CA 2 487 391 12/2003
CN 88203065 11/1988
(Continued)

OTHER PUBLICATIONS

Office Action for U.S. Appl. No. 11/078,855, dated Jan. 16, 2007.
(Continued)

*Primary Examiner* — James R Greece

(57) ABSTRACT

Eyewear having monitoring capability, such as for radiation or motion, is disclosed. Radiation, such as ultraviolet (UV) radiation, infrared (IR) radiation or light, can be measured by a detector. The measured radiation can then be used in providing radiation-related information to a user of the eyewear. Motion can be measure by a detector, and the measured motion can be used to determine whether the eyewear is being worn.

46 Claims, 39 Drawing Sheets

Related U.S. Application Data

Aug. 14, 2018, now Pat. No. 10,359,311, which is a continuation of application No. 15/343,472, filed on Nov. 4, 2016, now Pat. No. 10,060,790, which is a continuation of application No. 14/313,989, filed on Jun. 24, 2014, now Pat. No. 9,488,520, which is a continuation of application No. 12/322,377, filed on Feb. 2, 2009, now Pat. No. 8,770,742, which is a continuation of application No. 11/078,855, filed on Mar. 11, 2005, now Pat. No. 7,500,746.

(60) Provisional application No. 60/647,826, filed on Jan. 31, 2005, provisional application No. 60/647,836, filed on Jan. 31, 2005, provisional application No. 60/620,238, filed on Oct. 18, 2004, provisional application No. 60/618,107, filed on Oct. 12, 2004, provisional application No. 60/605,191, filed on Aug. 28, 2004, provisional application No. 60/592,045, filed on Jul. 28, 2004, provisional application No. 60/583,169, filed on Jun. 26, 2004, provisional application No. 60/562,798, filed on Apr. 15, 2004.

(56) References Cited

U.S. PATENT DOCUMENTS

| | | |
|---|---|---|
| 1,255,265 A | 2/1918 | Zachara |
| 1,917,745 A | 7/1933 | Weiss |
| 2,249,572 A | 7/1941 | Lieber |
| 2,638,532 A | 5/1953 | Brady |
| 2,794,085 A | 5/1957 | Angelis |
| 2,818,511 A | 12/1957 | Ullery et al. |
| 2,830,132 A | 4/1958 | Borg |
| 2,874,230 A | 2/1959 | Carlson |
| 2,904,670 A | 9/1959 | Calmes |
| 3,060,308 A | 10/1962 | Fortuna |
| 3,104,290 A | 9/1963 | Rosemond et al. |
| 3,119,903 A | 1/1964 | Rosemond et al. |
| 3,597,054 A | 8/1971 | Winter |
| 3,710,115 A | 1/1973 | Jubb |
| 3,858,001 A | 12/1974 | Bonne |
| 3,883,701 A | 5/1975 | Delorenzo |
| 4,165,487 A | 8/1979 | Corderman |
| 4,254,451 A | 3/1981 | Cochran, Jr. |
| 4,283,127 A | 8/1981 | Rosenwinkel et al. |
| 4,322,585 A | 3/1982 | Liautaud |
| 4,348,664 A | 9/1982 | Boschetti et al. |
| 4,389,217 A | 6/1983 | Baughman et al. |
| 4,526,473 A | 7/1985 | Zahn, III |
| 4,535,244 A | 8/1985 | Burnham |
| 4,608,492 A | 8/1986 | Burnham |
| 4,683,587 A | 7/1987 | Silverman |
| 4,751,691 A | 6/1988 | Perera |
| 4,757,714 A | 7/1988 | Purdy et al. |
| 4,773,095 A | 9/1988 | Zwicker et al. |
| 4,806,011 A | 2/1989 | Bettinger |
| 4,822,160 A | 4/1989 | Tsai |
| 4,822,161 A | 4/1989 | Jimmy |
| 4,851,686 A | 7/1989 | Pearson |
| 4,856,086 A | 8/1989 | McCullough |
| 4,859,047 A | 8/1989 | Badewitz |
| 4,882,769 A | 11/1989 | Gallimore |
| 4,904,078 A | 2/1990 | Gorike |
| 4,942,629 A | 7/1990 | Stadlmann |
| 4,962,469 A | 10/1990 | Ono et al. |
| 4,967,268 A | 10/1990 | Lipton et al. |
| 4,985,632 A | 1/1991 | Bianco et al. |
| 5,008,548 A | 4/1991 | Gat |
| 5,015,086 A | 5/1991 | Okaue et al. |
| 5,020,150 A | 5/1991 | Shannon |
| 5,026,151 A | 6/1991 | Waltuck et al. |
| 5,036,311 A | 7/1991 | Moran et al. |
| 5,050,150 A | 9/1991 | Ikeda |
| 5,064,410 A | 11/1991 | Frenkel et al. |
| 5,093,576 A | 3/1992 | Edmond et al. |
| 5,106,179 A | 4/1992 | Kamaya et al. |
| 5,144,344 A | 9/1992 | Takahashi et al. |
| 5,148,023 A | 9/1992 | Hayashi et al. |
| 5,151,600 A | 9/1992 | Black |
| 5,161,250 A | 11/1992 | Ianna et al. |
| 5,172,256 A | 12/1992 | Sethofer et al. |
| 5,264,877 A | 11/1993 | Hussey |
| 5,306,917 A | 4/1994 | Black et al. |
| 5,353,378 A | 10/1994 | Hoffman et al. |
| 5,359,370 A | 10/1994 | Mugnier |
| 5,359,444 A | 10/1994 | Piosenka et al. |
| 5,367,345 A | 11/1994 | da Silva |
| 5,379,464 A | 1/1995 | Schleger et al. |
| 5,382,986 A | 1/1995 | Black et al. |
| 5,394,005 A | 2/1995 | Brown et al. |
| 5,452,026 A | 9/1995 | Marcy, III |
| 5,452,480 A | 9/1995 | Ryden |
| 5,455,637 A | 10/1995 | Kallman et al. |
| 5,455,640 A | 10/1995 | Gertsikov |
| 5,457,751 A | 10/1995 | Such |
| 5,463,428 A | 10/1995 | Lipton et al. |
| 5,475,798 A | 12/1995 | Handles |
| 5,500,532 A | 3/1996 | Kozicki |
| D369,167 S | 4/1996 | Hanson et al. |
| 5,510,961 A | 4/1996 | Peng |
| 5,513,384 A | 4/1996 | Brennan et al. |
| 5,533,130 A | 7/1996 | Staton |
| 5,541,641 A | 7/1996 | Shimada |
| 5,581,090 A | 12/1996 | Goudjil |
| 5,585,871 A | 12/1996 | Linden |
| 5,589,398 A | 12/1996 | Krause et al. |
| 5,590,417 A | 12/1996 | Rydbeck |
| 5,606,743 A | 2/1997 | Vogt et al. |
| 5,608,808 A | 3/1997 | da Silva |
| 5,634,201 A | 5/1997 | Mooring |
| 5,671,035 A | 9/1997 | Barnes |
| 5,686,727 A | 11/1997 | Reenstra et al. |
| 5,694,475 A | 12/1997 | Boyden |
| 5,715,323 A | 2/1998 | Walker |
| 5,737,436 A | 4/1998 | Boyden et al. |
| 5,777,715 A | 7/1998 | Kruegle et al. |
| 5,818,381 A | 10/1998 | Williams |
| 5,835,185 A | 11/1998 | Kallman et al. |
| 5,900,720 A | 5/1999 | Kallman et al. |
| 5,903,395 A | 5/1999 | Rallison et al. |
| 5,923,398 A | 7/1999 | Goldman |
| 5,941,837 A | 8/1999 | Amano et al. |
| 5,946,071 A | 8/1999 | Feldman |
| 5,949,516 A | 9/1999 | McCurdy |
| 5,966,746 A | 10/1999 | Reedy et al. |
| 5,980,037 A | 11/1999 | Conway |
| 5,988,812 A | 11/1999 | Wingate |
| 5,991,085 A | 11/1999 | Rallison et al. |
| 5,992,996 A | 11/1999 | Sawyer |
| 5,995,592 A | 11/1999 | Shirai et al. |
| 6,010,216 A | 1/2000 | Jesiek |
| 6,013,919 A | 1/2000 | Schneider et al. |
| 6,028,627 A | 2/2000 | Helmsderfer |
| 6,046,455 A | 4/2000 | Ribi et al. |
| 6,060,321 A | 5/2000 | Hovorka |
| 6,061,580 A | 5/2000 | Altschul et al. |
| 6,091,546 A | 7/2000 | Spitzer |
| 6,091,832 A | 7/2000 | Shurman et al. |
| 6,115,177 A | 9/2000 | Vossler |
| 6,132,681 A | 10/2000 | Faran et al. |
| 6,145,983 A | 11/2000 | Schiffer |
| 6,154,552 A | 11/2000 | Koroljow et al. |
| 6,176,576 B1 | 1/2001 | Green et al. |
| 6,225,897 B1 | 5/2001 | Doyle et al. |
| 6,231,181 B1 | 5/2001 | Swab |
| 6,236,969 B1 | 5/2001 | Ruppert et al. |
| 6,243,578 B1 | 6/2001 | Koike |
| 6,259,367 B1 | 7/2001 | Klein |
| 6,270,466 B1 | 8/2001 | Weinstein et al. |
| 6,292,213 B1 | 9/2001 | Jones |
| 6,292,685 B1 | 9/2001 | Pompei |
| 6,301,050 B1 | 10/2001 | DeLeon |
| 6,301,367 B1 | 10/2001 | Boyden et al. |

(56) References Cited

U.S. PATENT DOCUMENTS

| | | | |
|---|---|---|---|
| 6,307,526 B1 | 10/2001 | Mann | |
| 6,311,155 B1 | 10/2001 | Vaudrey et al. | |
| 6,343,858 B1 | 2/2002 | Zelman | |
| 6,346,929 B1 | 2/2002 | Fukushima et al. | |
| 6,349,001 B1 | 2/2002 | Spitzer | |
| 6,349,422 B1 | 2/2002 | Schleger et al. | |
| 6,409,335 B1 | 6/2002 | Lipawsky | |
| 6,409,338 B1 | 6/2002 | Jewell | |
| 6,426,719 B1 | 7/2002 | Nagareda et al. | |
| 6,431,705 B1 | 8/2002 | Linden | |
| 6,474,816 B2 | 11/2002 | Butler et al. | |
| 6,478,736 B1 | 11/2002 | Mault | |
| 6,506,142 B2 | 1/2003 | Itoh et al. | |
| 6,511,175 B2 | 1/2003 | Hay et al. | |
| 6,513,532 B2 | 2/2003 | Mault et al. | |
| 6,517,203 B1 | 2/2003 | Blum et al. | |
| 6,539,336 B1 | 3/2003 | Vock et al. | |
| 6,542,081 B2 | 4/2003 | Torch | |
| 6,546,101 B1 | 4/2003 | Murray et al. | |
| 6,554,763 B1 | 4/2003 | Amano et al. | |
| 6,582,075 B1 | 6/2003 | Swab et al. | |
| 6,619,799 B1 | 9/2003 | Blum et al. | |
| 6,629,076 B1 | 9/2003 | Haken | |
| 6,717,737 B1 | 4/2004 | Haglund | |
| 6,729,726 B2 | 5/2004 | Miller et al. | |
| 6,736,759 B1 | 5/2004 | Stubbs et al. | |
| 6,764,194 B1 | 7/2004 | Cooper | |
| 6,769,767 B2 | 8/2004 | Swab et al. | |
| 6,771,423 B2 | 8/2004 | Geist | |
| 6,788,309 B1 | 9/2004 | Swan et al. | |
| 6,792,401 B1 | 9/2004 | Nigro et al. | |
| 6,816,314 B2 | 11/2004 | Shimizu et al. | |
| 6,824,265 B1 | 11/2004 | Harper | |
| 6,857,741 B2 * | 2/2005 | Blum | G02B 27/017 351/159.39 |
| 6,871,951 B2 | 3/2005 | Blum et al. | |
| 6,879,930 B2 | 4/2005 | Sinclair et al. | |
| 6,912,386 B1 | 6/2005 | Himberg et al. | |
| 6,929,365 B2 | 8/2005 | Swab et al. | |
| 6,932,090 B1 | 8/2005 | Reschke et al. | |
| 6,947,219 B1 | 9/2005 | Ou | |
| 7,004,582 B2 | 2/2006 | Jannard et al. | |
| 7,013,009 B2 | 3/2006 | Warren | |
| 7,023,594 B2 * | 4/2006 | Blum | G02F 1/134309 351/159.03 |
| 7,030,902 B2 | 4/2006 | Jacobs | |
| 7,031,667 B2 | 4/2006 | Horiguchi | |
| 7,033,025 B2 | 4/2006 | Winterbotham | |
| 7,059,717 B2 | 6/2006 | Bloch | |
| 7,073,905 B2 | 7/2006 | Da Pra' | |
| 7,079,876 B2 | 7/2006 | Levy | |
| 7,123,215 B2 | 10/2006 | Nakada | |
| 7,192,136 B2 | 3/2007 | Howell et al. | |
| 7,255,437 B2 * | 8/2007 | Howell | G02C 11/10 351/158 |
| 7,265,358 B2 | 9/2007 | Fontaine | |
| 7,274,292 B2 | 9/2007 | Velhal et al. | |
| 7,289,767 B2 | 10/2007 | Lai | |
| 7,312,699 B2 | 12/2007 | Chornenky | |
| 7,331,666 B2 | 2/2008 | Swab et al. | |
| 7,376,238 B1 | 5/2008 | Rivas et al. | |
| 7,380,936 B2 | 6/2008 | Howell et al. | |
| 7,401,918 B2 | 7/2008 | Howell et al. | |
| 7,405,801 B2 | 7/2008 | Jacobs | |
| 7,429,965 B2 | 9/2008 | Weiner | |
| 7,438,409 B2 | 10/2008 | Jordan | |
| 7,438,410 B1 | 10/2008 | Howell et al. | |
| 7,445,332 B2 | 11/2008 | Jannard et al. | |
| 7,481,531 B2 | 1/2009 | Howell et al. | |
| 7,500,746 B1 | 3/2009 | Howell et al. | |
| 7,500,747 B2 | 3/2009 | Howell et al. | |
| 7,512,414 B2 | 3/2009 | Jannard et al. | |
| 7,517,083 B2 * | 4/2009 | Blum | G02B 27/017 351/159.44 |
| 7,527,374 B2 | 5/2009 | Chou | |
| 7,543,934 B2 | 6/2009 | Howell et al. | |
| 7,581,833 B2 | 9/2009 | Howell et al. | |
| 7,621,634 B2 | 11/2009 | Howell et al. | |
| 7,648,236 B1 | 1/2010 | Dobson | |
| 7,677,723 B2 | 3/2010 | Howell et al. | |
| 7,760,898 B2 | 7/2010 | Howell et al. | |
| 7,771,046 B2 | 8/2010 | Howell et al. | |
| 7,792,552 B2 | 9/2010 | Thomas et al. | |
| 7,806,525 B2 | 10/2010 | Howell et al. | |
| 7,922,321 B2 | 4/2011 | Howell et al. | |
| 7,976,159 B2 | 7/2011 | Jacobs et al. | |
| 8,109,629 B2 | 2/2012 | Howell et al. | |
| 8,142,015 B2 | 3/2012 | Paolino | |
| 8,174,569 B2 | 5/2012 | Tanijiri et al. | |
| 8,337,013 B2 | 12/2012 | Howell et al. | |
| 8,430,507 B2 | 4/2013 | Howell et al. | |
| 8,434,863 B2 | 5/2013 | Howell et al. | |
| 8,465,151 B2 | 6/2013 | Howell et al. | |
| 8,485,661 B2 | 7/2013 | Yoo et al. | |
| 8,500,271 B2 | 8/2013 | Howell et al. | |
| 8,770,742 B2 | 7/2014 | Howell et al. | |
| 8,905,542 B2 | 12/2014 | Howell et al. | |
| 9,033,493 B2 | 5/2015 | Howell et al. | |
| 9,244,292 B2 | 1/2016 | Swab et al. | |
| 9,400,390 B2 | 7/2016 | Osterhout et al. | |
| 9,405,135 B2 | 8/2016 | Sweis et al. | |
| 9,488,520 B2 | 11/2016 | Howell et al. | |
| 9,547,184 B2 | 1/2017 | Howell et al. | |
| 9,690,121 B2 | 6/2017 | Howell et al. | |
| 9,922,236 B2 | 3/2018 | Moore et al. | |
| 10,042,186 B2 | 8/2018 | Chao et al. | |
| 10,060,790 B2 | 8/2018 | Howell et al. | |
| 10,061,144 B2 | 8/2018 | Howell et al. | |
| 10,310,296 B2 | 6/2019 | Howell et al. | |
| 10,345,625 B2 | 7/2019 | Howell et al. | |
| 10,359,311 B2 | 7/2019 | Howell et al. | |
| 10,515,623 B1 | 12/2019 | Grizzel | |
| 10,539,459 B2 | 1/2020 | Howell et al. | |
| 10,571,715 B2 | 2/2020 | Rizzo, III et al. | |
| 10,624,790 B2 | 4/2020 | Chao et al. | |
| 10,777,048 B2 | 9/2020 | Howell et al. | |
| 10,802,582 B1 | 10/2020 | Clements | |
| 10,964,190 B2 | 3/2021 | Peyrard | |
| 11,042,045 B2 | 6/2021 | Chao et al. | |
| 11,069,358 B1 | 7/2021 | Harper | |
| 11,086,147 B2 | 8/2021 | Howell et al. | |
| 11,204,512 B2 | 12/2021 | Howell et al. | |
| 11,243,416 B2 | 2/2022 | Howell et al. | |
| 11,326,941 B2 | 5/2022 | Howell et al. | |
| 11,513,371 B2 | 11/2022 | Howell et al. | |
| 11,536,988 B2 | 12/2022 | Howell et al. | |
| 2001/0005230 A1 | 6/2001 | Ishikawa | |
| 2001/0028309 A1 | 10/2001 | Torch | |
| 2001/0050754 A1 | 12/2001 | Hay et al. | |
| 2002/0017997 A1 | 2/2002 | Felkowitz | |
| 2002/0021407 A1 | 2/2002 | Elliott | |
| 2002/0081982 A1 | 6/2002 | Schwartz et al. | |
| 2002/0084990 A1 | 7/2002 | Peterson, III | |
| 2002/0089639 A1 | 7/2002 | Starner et al. | |
| 2002/0090103 A1 | 7/2002 | Calisto, Jr. | |
| 2002/0098877 A1 | 7/2002 | Glezerman | |
| 2002/0101568 A1 | 8/2002 | Eberl et al. | |
| 2002/0109600 A1 | 8/2002 | Mault et al. | |
| 2002/0140899 A1 | 10/2002 | Blum et al. | |
| 2002/0159023 A1 | 10/2002 | Swab | |
| 2002/0197961 A1 | 12/2002 | Warren | |
| 2003/0018274 A1 | 1/2003 | Takahashi et al. | |
| 2003/0022690 A1 | 1/2003 | Beyda et al. | |
| 2003/0032449 A1 | 2/2003 | Giobbi | |
| 2003/0062046 A1 | 4/2003 | Wiesmann et al. | |
| 2003/0065257 A1 | 4/2003 | Mault et al. | |
| 2003/0067585 A1 | 4/2003 | Miller et al. | |
| 2003/0068057 A1 | 4/2003 | Miller et al. | |
| 2003/0083591 A1 | 5/2003 | Edwards et al. | |
| 2003/0214630 A1 | 11/2003 | Winterbotham | |
| 2003/0226978 A1 | 12/2003 | Ribi et al. | |
| 2003/0231293 A1 * | 12/2003 | Blum | G02F 1/29 356/5.01 |
| 2004/0000733 A1 | 1/2004 | Swab et al. | |

(56) References Cited

U.S. PATENT DOCUMENTS

| | | |
|---|---|---|
| 2004/0029582 A1 | 2/2004 | Swab et al. |
| 2004/0059212 A1 | 3/2004 | Abreu |
| 2004/0063378 A1 | 4/2004 | Nelson |
| 2004/0096078 A1 | 5/2004 | Lin |
| 2004/0100384 A1 | 5/2004 | Chen et al. |
| 2004/0101178 A1 | 5/2004 | Fedorovskaya et al. |
| 2004/0104864 A1 | 6/2004 | Nakada |
| 2004/0128737 A1 | 7/2004 | Gesten |
| 2004/0150986 A1 | 8/2004 | Chang |
| 2004/0156012 A1 | 8/2004 | Jannard et al. |
| 2004/0157649 A1 | 8/2004 | Jannard et al. |
| 2004/0160571 A1 | 8/2004 | Jannard |
| 2004/0160572 A1 | 8/2004 | Jannard |
| 2004/0160573 A1 | 8/2004 | Jannard et al. |
| 2004/0197002 A1 | 10/2004 | Atsumi et al. |
| 2004/0227219 A1 | 11/2004 | Su |
| 2005/0036103 A1 | 2/2005 | Bloch |
| 2005/0067580 A1 | 3/2005 | Fontaine |
| 2005/0078274 A1 | 4/2005 | Howell et al. |
| 2005/0088365 A1 | 4/2005 | Yamazaki et al. |
| 2005/0201585 A1 | 9/2005 | Jannard et al. |
| 2005/0213026 A1 | 9/2005 | Da Pra' |
| 2005/0230596 A1 | 10/2005 | Howell et al. |
| 2005/0238194 A1 | 10/2005 | Chornenky |
| 2005/0239502 A1 | 10/2005 | Swab et al. |
| 2005/0248717 A1 | 11/2005 | Howell et al. |
| 2005/0248718 A1 | 11/2005 | Howell et al. |
| 2005/0248719 A1 | 11/2005 | Howell et al. |
| 2005/0264752 A1 | 12/2005 | Howell et al. |
| 2005/0278446 A1 | 12/2005 | Bryant |
| 2006/0001827 A1 | 1/2006 | Howell et al. |
| 2006/0003803 A1 | 1/2006 | Thomas et al. |
| 2006/0023158 A1 | 2/2006 | Howell et al. |
| 2006/0034478 A1 | 2/2006 | Davenport |
| 2006/0107822 A1 | 5/2006 | Bowen |
| 2006/0132382 A1 | 6/2006 | Jannard |
| 2007/0030442 A1 | 2/2007 | Howell et al. |
| 2007/0035830 A1 | 2/2007 | Matveev et al. |
| 2007/0046887 A1 | 3/2007 | Howell et al. |
| 2007/0055888 A1 | 3/2007 | Miller et al. |
| 2007/0098192 A1 | 5/2007 | Sipkema |
| 2007/0109491 A1 | 5/2007 | Howell et al. |
| 2007/0186330 A1 | 8/2007 | Howell et al. |
| 2007/0200927 A1 | 8/2007 | Krenik |
| 2007/0208531 A1 | 9/2007 | Darley et al. |
| 2007/0248238 A1 | 10/2007 | Abreu et al. |
| 2007/0270663 A1 | 11/2007 | Ng et al. |
| 2007/0271065 A1 | 11/2007 | Gupta et al. |
| 2007/0271116 A1 | 11/2007 | Wysocki et al. |
| 2007/0271387 A1 | 11/2007 | Lydon et al. |
| 2007/0279584 A1 | 12/2007 | Howell et al. |
| 2008/0062338 A1 | 3/2008 | Herzog et al. |
| 2008/0068559 A1 | 3/2008 | Howell et al. |
| 2008/0089545 A1 | 4/2008 | Jannard et al. |
| 2008/0100792 A1 | 5/2008 | Blum et al. |
| 2008/0144854 A1 | 6/2008 | Abreu |
| 2008/0151175 A1 | 6/2008 | Gross |
| 2008/0151179 A1 | 6/2008 | Howell et al. |
| 2008/0158506 A1 | 7/2008 | Fuziak |
| 2008/0211921 A1 | 9/2008 | Sako et al. |
| 2008/0218684 A1 | 9/2008 | Howell et al. |
| 2008/0262392 A1 | 10/2008 | Ananny et al. |
| 2008/0278678 A1 | 11/2008 | Howell et al. |
| 2009/0059159 A1 | 3/2009 | Howell et al. |
| 2009/0059381 A1 | 3/2009 | Jannard |
| 2009/0073375 A1 | 3/2009 | Nakada |
| 2009/0141233 A1 | 6/2009 | Howell et al. |
| 2009/0147215 A1 | 6/2009 | Howell et al. |
| 2009/0156128 A1 | 6/2009 | Franson et al. |
| 2009/0251660 A1 | 10/2009 | Figler et al. |
| 2009/0251661 A1 | 10/2009 | Fuziak, Jr. |
| 2009/0296044 A1 | 12/2009 | Howell et al. |
| 2010/0045928 A1 | 2/2010 | Levy |
| 2010/0061579 A1 | 3/2010 | Rickards et al. |
| 2010/0079356 A1 | 4/2010 | Hoellwarth |
| 2010/0105445 A1 | 4/2010 | Brunton et al. |
| 2010/0110368 A1 | 5/2010 | Chaum |
| 2010/0245754 A1 | 9/2010 | Matsumoto et al. |
| 2010/0296045 A1 | 11/2010 | Agnoli et al. |
| 2010/0309426 A1 | 12/2010 | Howell et al. |
| 2011/0102734 A1 | 5/2011 | Howell et al. |
| 2011/0164122 A1 | 7/2011 | Hardacker |
| 2011/0187990 A1 | 8/2011 | Howell et al. |
| 2011/0241976 A1 | 10/2011 | Boger et al. |
| 2011/0273365 A1 | 11/2011 | West et al. |
| 2012/0033061 A1 | 2/2012 | Ko et al. |
| 2012/0050668 A1 | 3/2012 | Howell et al. |
| 2012/0062357 A1 | 3/2012 | Slamka |
| 2012/0101411 A1 | 4/2012 | Hausdorff et al. |
| 2012/0133885 A1 | 5/2012 | Howell et al. |
| 2012/0176580 A1 | 7/2012 | Sonsino |
| 2013/0072828 A1 | 3/2013 | Sweis et al. |
| 2013/0077175 A1 | 3/2013 | Hotta et al. |
| 2013/0143519 A1 | 6/2013 | Doezema |
| 2013/0172691 A1 | 7/2013 | Tran |
| 2013/0201440 A1 | 8/2013 | Howell et al. |
| 2013/0308089 A1 | 11/2013 | Howell et al. |
| 2014/0132913 A1 | 5/2014 | Sweis et al. |
| 2014/0176902 A1 | 6/2014 | Sweis et al. |
| 2014/0198293 A1 | 7/2014 | Sweis et al. |
| 2014/0226838 A1 | 8/2014 | Wingate et al. |
| 2014/0268008 A1 | 9/2014 | Howell et al. |
| 2014/0268013 A1 | 9/2014 | Howell et al. |
| 2014/0268017 A1 | 9/2014 | Sweis et al. |
| 2014/0361185 A1 | 12/2014 | Howell et al. |
| 2015/0085245 A1 | 3/2015 | Howell et al. |
| 2015/0230988 A1 | 8/2015 | Chao et al. |
| 2015/0253590 A1 | 9/2015 | Howell et al. |
| 2015/0277123 A1 | 10/2015 | Chaum et al. |
| 2015/0338677 A1 | 11/2015 | Block |
| 2016/0098874 A1 | 4/2016 | Handville et al. |
| 2016/0246075 A9 | 8/2016 | Howell et al. |
| 2016/0302992 A1 | 10/2016 | Sweis et al. |
| 2017/0068117 A9 | 3/2017 | Howell et al. |
| 2017/0074721 A1 | 3/2017 | Howell et al. |
| 2017/0090219 A1 | 3/2017 | Howell et al. |
| 2017/0131575 A1 | 5/2017 | Howell et al. |
| 2017/0146829 A1 | 5/2017 | Howell et al. |
| 2017/0303187 A1 | 10/2017 | Crouthamel et al. |
| 2018/0122208 A1 | 5/2018 | Peyrard |
| 2018/0314079 A1 | 11/2018 | Chao et al. |
| 2018/0335650 A1 | 11/2018 | Howell et al. |
| 2018/0348050 A1 | 12/2018 | Howell et al. |
| 2019/0004325 A1 | 1/2019 | Connor |
| 2019/0033622 A1 | 1/2019 | Olgun et al. |
| 2019/0033623 A1 | 1/2019 | Howell et al. |
| 2019/0187492 A1 | 6/2019 | Howell et al. |
| 2019/0272800 A1 | 9/2019 | Tao et al. |
| 2019/0278110 A1 | 9/2019 | Howell et al. |
| 2019/0285913 A1 | 9/2019 | Howell et al. |
| 2019/0310132 A1 | 10/2019 | Howell et al. |
| 2019/0318589 A1 | 10/2019 | Howell et al. |
| 2019/0369402 A1 | 12/2019 | Woodman et al. |
| 2019/0378493 A1 | 12/2019 | Kim et al. |
| 2019/0387351 A1 | 12/2019 | Lyren et al. |
| 2020/0012127 A1 | 1/2020 | Howell et al. |
| 2020/0218094 A1 | 7/2020 | Howell et al. |
| 2020/0364992 A1 | 11/2020 | Howell et al. |
| 2021/0000347 A1 | 1/2021 | Stump |
| 2021/0026146 A1 | 1/2021 | Harder et al. |
| 2021/0271116 A1 | 9/2021 | Chao et al. |
| 2021/0364827 A9 | 11/2021 | Howell et al. |
| 2021/0364828 A1 | 11/2021 | Howell et al. |
| 2021/0379425 A1 | 12/2021 | Tran |
| 2022/0008763 A1 | 1/2022 | Saleh et al. |
| 2022/0011603 A1 | 1/2022 | Howell et al. |
| 2022/0034542 A1 | 2/2022 | Peters et al. |
| 2022/0054092 A1 | 2/2022 | Howell et al. |
| 2022/0335792 A1 | 10/2022 | Howell et al. |
| 2023/0017634 A1 | 1/2023 | Howell et al. |

(56) References Cited

U.S. PATENT DOCUMENTS

| | | | |
|---|---|---|---|
| 2023/0033660 A1 | 2/2023 | Howell et al. | |
| 2023/0057654 A1 | 2/2023 | Howell et al. | |

FOREIGN PATENT DOCUMENTS

| | | |
|---|---|---|
| CN | 89214222.7 | 3/1990 |
| CN | 90208199.3 | 11/1990 |
| DE | 10123226 A1 | 11/2002 |
| EP | 1134491 A2 | 9/2001 |
| EP | 1027626 B1 | 3/2022 |
| EP | 2290433 B1 | 4/2022 |
| FR | 2530039 A1 | 1/1984 |
| GB | 1467982 | 3/1977 |
| JP | 58-113912 | 7/1983 |
| JP | 58-113914 | 7/1983 |
| JP | 02-181722 | 7/1990 |
| JP | 09-017204 | 1/1997 |
| JP | 10-161072 | 6/1998 |
| JP | 2000-039595 | 2/2000 |
| JP | 2002 341059 A | 11/2002 |
| JP | 2005-151292 | 6/2005 |
| JP | 2005-167902 | 6/2022 |
| TW | 484711 | 6/2001 |
| WO | WO 97/12205 A1 | 4/1997 |
| WO | WO 99/50706 A1 | 10/1999 |
| WO | WO 01/06298 A1 | 1/2001 |
| WO | WO 02/06881 A2 | 1/2002 |
| WO | WO 03/069394 A1 | 8/2003 |
| WO | WO 03/100368 A1 | 12/2003 |
| WO | WO 03/100503 A2 | 12/2003 |
| WO | WO 04/012477 A2 | 2/2004 |
| WO | WO 04/025554 A1 | 3/2004 |

OTHER PUBLICATIONS

Office Action for U.S. Appl. No. 11/078,855, dated Aug. 8, 2007.
Office Action for U.S. Appl. No. 11/078,855, dated Dec. 26, 2007.
Office Action for U.S. Appl. No. 11/078,855, dated Jul. 3, 2008.
Notice of Allowance for U.S. Appl. No. 11/078,855, dated Dec. 3, 2008.
Office Action for U.S. Appl. No. 12/322,377, dated Mar. 31, 2010.
Office Action for U.S. Appl. No. 12/322,377, dated Oct. 14, 2010.
Office Action for U.S. Appl. No. 12/322,377, dated Sep. 17, 2013.
Office Action for U.S. Appl. No. 12/322,377, dated Feb. 25, 2014.
Notice of Allowance for U.S. Appl. No. 12/322,377, dated May 2, 2014.
Office Action for U.S. Appl. No. 14/313,989, dated Sep. 24, 2014.
Office Action for U.S. Appl. No. 14/313,989, dated Feb. 9, 2015.
Notice of Allowance for U.S. Appl. No. 14/313,989, dated Jul. 21, 2015.
Notice of Allowance for U.S. Appl. No. 14/313,989, dated Nov. 5, 2015.
Notice of Allowance for U.S. Appl. No. 14/313,989, dated Feb. 17, 2016.
Notice of Allowance for U.S. Appl. No. 14/313,989, dated Jun. 17, 2016.
Office Action for U.S. Appl. No. 15/343,472, dated Jun. 28, 2017.
Notice of Allowance for U.S. Appl. No. 15/343,472, dated Oct. 5, 2017.
Notice of Allowance for U.S. Appl. No. 15/343,472, dated Jan. 26, 2018.
Notice of Allowance for U.S. Appl. No. 15/343,472, dated Jun. 1, 2018.
Office Action for U.S. Appl. No. 16/102,859, dated Sep. 5, 2018.
Notice of Allowance for U.S. Appl. No. 16/102,859, dated Jan. 4, 2019.
Notice of Allowance for U.S. Appl. No. 16/102,859, dated Apr. 15, 2019.
Office Action for U.S. Appl. No. 16/426,351, dated Sep. 18, 2019.
Advisory Action for U.S. Appl. No. 16/426,351, dated Nov. 15, 2019.
Office Action for U.S. Appl. No. 16/703,805, dated Sep. 1, 2020.
Office Action for U.S. Appl. No. 16/703,805, dated Feb. 25, 2021.
Office Action for U.S. Appl. No. 16/703,805, dated Jul. 28, 2021.
Notice of Allowance for U.S. Appl. No. 16/703,805, dated Nov. 9, 2021.
Restriction Requirement for U.S. Appl. No. 11/078,857, dated Jun. 5, 2007.
Office Action for U.S. Appl. No. 11/078,857, dated Sep. 5, 2007.
Office Action for U.S. Appl. No. 11/078,857, dated Apr. 7, 2008.
Advisory Action for U.S. Appl. No. 11/078,857, dated Jun. 27, 2008.
Office Action for U.S. Appl. No. 11/078,857, dated Sep. 22, 2008.
U.S. Appl. No. 13/831,419, filed Mar. 14, 2013.
Office Action for U.S. Appl. No. 13/831,419, dated Apr. 27, 2015.
Office Action for U.S. Appl. No. 13/831,419, dated Aug. 12, 2015.
Notice of Allowance for U.S. Appl. No. 13/831,419, dated Jan. 28, 2016.
Office Action for U.S. Appl. No. 13/831,419, dated Apr. 28, 2016.
Office Action for U.S. Appl. No. 13/831,419, dated Nov. 17, 2016.
Office Action for U.S. Appl. No. 13/831,419, dated Feb. 1, 2017.
Notice of Allowance for U.S. Appl. No. 13/831,419, dated Jun. 6, 2017.
Office Action for U.S. Appl. No. 13/831,419, dated Oct. 20, 2017.
Office Action for U.S. Appl. No. 13/831,419, dated Jun. 8, 2018.
U.S. Appl. No. 13/831,445, filed Mar. 14, 2013.
Office Action for U.S. Appl. No. 13/831,445, dated Feb. 20, 2015.
Notice of Allowance for U.S. Appl. No. 13/831,445, dated Oct. 21, 2016.
Notice of Allowance for U.S. Appl. No. 13/831,445, dated Jan. 9, 2017.
Corrected Notice of Allowance for U.S. Appl. No. 13/831,445, dated Jan. 23, 2017.
Notice of Allowance for U.S. Appl. No. 13/831,445, dated Apr. 25, 2017.
Office Action for U.S. Appl. No. 13/831,445, dated Feb. 6, 2018.
Notice of Allowance for U.S. Appl. No. 13/831,445, dated Aug. 8, 2018.
Office Action for U.S. Appl. No. 16/429,181, dated Sep. 30, 2020.
Notice of Allowance for U.S. Appl. No. 16/429,181, dated Feb. 1, 2021.
Notice of Allowance for U.S. Appl. No. 16/429,181, dated Jun. 17, 2021.
Notice of Allowance for U.S. Appl. No. 16/429,181, dated Aug. 19, 2021.
Notice of Allowance for U.S. Appl. No. 16/429,181, dated Oct. 4, 2021.
Office Action for U.S. Appl. No. 16/424,018, dated Jun. 10, 2020.
Notice of Allowance for U.S. Appl. No. 16/424,018, dated Oct. 20, 2020.
Notice of Allowance for U.S. Appl. No. 16/424,018, dated Mar. 8, 2021.
Office Action for U.S. Appl. No. 16/424,018, dated May 13, 2021.
Office Action for U.S. Appl. No. 16/424,018, dated Sep. 3, 2021.
Notice of Allowance for U.S. Appl. No. 16/424,018, dated Nov. 2, 2021.
Office Action for U.S. Appl. No. 16/424,018, dated Jan. 24, 2022.
"±1.5g Dual Axis Micromachined Accelerometer", Freescale Semiconductor, Inc., Motorola Semiconductor Technical Data, MMA6260Q, Jun. 2004, pp. 1-7.
"APA Announces Shipment of the SunUV™ Personal UV Monitor", Press Release, Nov. 7, 2003, pp. 1-3.
"Camera Specs Take Candid Snaps", BBC News, Sep. 18, 2003, pp. 1-3.
"Cardo Wireless Attaching Clips and Wearing Headset", Cardo Systems, Inc., http://www.cardowireless.com/clips.php, downloaded Nov. 27, 2004, pp. 1-3.
"Environmental Health Criteria 14: Ultraviolet Radiation", International Programme on Chemical Safety, World Health Organization Geneva, 1979 http://www.ichem.org., pp. 1-102.
"Exclusive Media Event Marks Debut of OAKLEY THUMP: World's First Digital Audio Eyewear", Oakley Investor Relations, Press Release, Nov. 15, 2004, pp. 1-2.

(56) References Cited

OTHER PUBLICATIONS

"Eyetop", Product-Features, eyetop eyewear, eyetop belt worn, http://www.eyetop.net/products/eyetop/features.asp., downloaded Nov. 6, 2003, pp. 1-2.
"Heart Rate Monitors", http://www.healthgoods.com, downloaded Dec. 4, 2004.
"How is the UV Index Calculated", SunWise Program, U.S. Environmental Protection Agency, http://www.epa.gov/sunwise/uvcalc.html, downloaded Oct. 14, 2004, pp. 1-2.
"Industrial UV Measurements", APA Optics, Inc., http://www.apaoptics.com/uv/, downloaded Jul. 12, 2004, p. 1.
"Motorola and Oakley Introduce First Bluetooth Sunglasses-Cutting Edge RAZRWire Line Offers Consumers On-The-Go Connections", Motorola Mediacenter-Press Release, Feb. 14, 2005, pp. 1-2.
"Oakley Thump: Sunglasses Meet MP3 Player", with image, http://news.designtechnica.com/article4665.html, Jul. 13, 2004.
"Personal UV monitor," Optics.org, http://optics.org/articles/news/6/6/7/1 (downloaded Dec. 20, 2003), Jun. 9, 2000, pp. 1-2.
"SafeSun Personal Ultraviolet Light Meter", http://healthchecksystems.com/safesun.htm, downloaded Jul. 12, 2004, pp. 1-4.
"SafeSun Personal UV Meter", Introduction, Optix Tech Inc., http://www.safesun.com, downloaded Feb. 5, 2004, pp. 1-2.
SafeSun Personal UV Meter, features, Optix Tech Inc., http://www.safesun.com/features.html, downloaded May 1, 2004, pp. 1-2.
"Sharper Image—The FM Pedometer", e-Corporate Gifts.com, http://www.e-corporategifts.com/sr353.html, downloaded Jan. 22, 2005, pp. 1-2.
"Sun UV™ Personal UV Monitor", APA Optics, Inc., http://www.apaoptics.com/sunuv/uvfacts.html, downloaded Dec. 20, 2003, pp. 1-3.
"Ultraviolet Light and Sunglasses", Oberon's Frequently Asked Questions, http://www.oberoncompany.com/OBEnglish/FAQUV.html, downloaded Feb. 5, 2004, pp. 1-2.
"Ultraviolet Light Sensor", Barrett & Associates Engineering, http://www.barrettengineering.com/project_uvs.htm, downloaded Feb. 5, 2004, pp. 1-3.
"Ultraviolet Radiation (UVR)", Forum North, Ontario Ministry of Labour, http://www3.mb.sympatico.ca/~ericc/ULTRAVIOLET%20RADIATION.htm, downloaded Feb. 5, 2004, pp. 1-6.
"What Are Grippies?", Gripping Eyewear, Inc., http://www.grippingeyewear.com/whatare.html, downloaded Nov. 2, 2005.
"With Racing Heart", Skaloud et al., GPS World, Oct. 1, 2001, http://www.gpsworld.com/gpsworld/content/printContentPopup.jsp?id=1805, pp. 1-5.
Abrisa Product Information: Cold Mirrors, Abrisa, Jun. 2001, p. 1.
Abrisa Product Information: Commercial Hot Mirror, Abrisa, Jun. 2001, p. 1.
Alps Spectacle, Air Conduction Glass, Bone Conduction Glass, http://www.alps-inter.com/spec.htm, downloaded Dec. 10, 2003, pp. 1-2.
Altimeter and Compass Watches, http://store.yahoo.com/snowshack/altimeter-watches.html, downloaded May 3, 2004, pp. 1-2.
Bone Conduction Headgear HG16 Series, "Voiceducer," http://www.temco-j.co.jp/html/English/HG16.html, downloaded Dec. 10, 2003, pp. 1-3.
Carney, David, "The Ultimate MP3 Player for Athletes? Could be.", CNET Reviews, May 14, 2004, pp. 1-4.
Clifford, Michelle A., "Accelerometers Jump into the Consumer Goods Market", Sensors Online, http://www.sensorsmag.com, Aug. 2004.
Comfees.com, Adjustable Sports Band Style No. 1243, http://shop.store.yahoo.com/comfees/adsportbansty.html, downloaded Apr. 18, 2003, pp. 1-2.
Cool Last Minute Gift Ideas!, UltimateFatBurner Reviews and Articles, http://www.ultimatefatburner.com/gift-ideas.html, downloaded May 10, 2005, pp. 1-3.
Dickie et al. "Eye Contact Sensing Glasses for Attention-Sensitive Wearable Video Blogging," Human Media Lab, Queen's University, Kingston, ON K7L3N6, Canada, est. Apr. 2004, pp. 1-2.

Dixen, Brian, "ear-catching", Supertesten, Mobil, Apr. 2003 (estimated), pp. 37-41.
Global Solar UV Index, a Practical Guide, World Health Organization, 2002, pp. 1-28.
Grobart, Sam, "Digit-Sizing Your Computer Data", News Article, Sep. 2004, p. 1.
Life Monitor V1.1, Rhusoft Technologies Inc., http://www.rhusoft.com/lifemonitor/, Mar. 1, 2003, pp. 1-6.
Manes, Stephen, "Xtreme Cam", Forbes Magazine, Sep. 5, 2005, p. 96.
Mio, Physical, http://www.gophysical.com/, downloaded Jan. 27, 2004, 5 pages.
Monitoring Athletes Performance—2002 Winter Olympic News from KSL, Jan. 23, 2002, http://2002.ksl.com/news-3885i, pp. 1-3.
NIWA, "UV Index Information", http://www.niwa.cri.nz/services/uvozone/uvi-info, downloaded Jul. 15, 2004, pp. 1-2.
NuVision 60GX Steroscopic Wireless Glasses, Product Information, NuVision by MacNaughton, c. 1997, MacNaughton, Inc., pp. 1-2.
Pärkkä, Juha, et al., "A Wireless Wellness Monitor for Personal Weight Management", VTT Information Technology, Tampere, Finland, Nov. 2000, p. 1.
Pedometer, Model HJ-112, Omron Instruction Manual, Omron Healthcare, Inc., 2003, pp. 1-27.
PNY Announces Executive Attaché USB 2.0 Flash Drive and Pen Series, Press Release, PNY Technologies, Las Vegas, Jan. 8, 2004, pp. 1-2.
PNY Technologies, "Executive Attaché" http://www.pny.com/products/flash/execattache.asp downloaded Nov. 16, 2005.
Polar WM41 and 42 weight management monitor, http://www.simplysports/polar/weight_management/wm41-42.htm, downloaded Jan. 28, 2004, pp. 1-3.
Questions Answers, Pedometer.com, http://www.pedometer.com, downloaded May 5, 2005.
RazrWire, copyright Motorola, Inc., Jul. 2005, 1 page.
SafeSun Personal UV Meter, Scientific Data, Optix Tech Inc., http://www.safesun.com/scientific.html, downloaded May 1, 2004, pp. 1-3.
SafeSun Sensor, User's Manual, Optix Tech Inc., Jun. 1998, 2 pages.
Safesun, Personal UV Meter, "Technical Specifications", Optix Tech Inc., http://www.safesun.com/technical.html, downloaded Jul. 12, 2004, pp. 1-2.
SafeSun, Personal UV Meter, Experiments, Optix Tech Inc., http://www.safesun.com/experiments.html, downloaded Feb. 5, 2004, pp. 1-2.
Shades of Fun, Blinking Light Glasses, http://www.shadesoffun.com/Nov/Novpgs-14.html, downloaded Jul. 9, 2005, pp. 1-4.
SportLine Fitness Pedometer-Model 360, UltimateFatBurner Superstore, http://www.ultimatefatburner-store.com/ac_004.html, downloaded May 10, 2005, pp. 1-2.
Steele, Bonnie G. et al., "Bodies in motion: Monitoring daily activity and exercise with motion sensors in people with chronic pulmonary disease", VA Research & Development, Journal of Rehabilitation Research & Development, vol. 40, No. 5, Sep./Oct. 2003, Supplement 2, pp. 45-58.
Stevens, Kathy, "Should I Use a Pedometer When I Walk?", Healtheon/WebMD, Apr. 14, 2000.
Sundgot, Jørgen "2nd-gen Motorola Bluetooth headset", InfoSync World, Mar. 1, 2003, http://www.infosync.no/news/2002/n/2841.html, pp. 1-2.
SunSensors, Segan Industries, Inc., http://www.segan-ind.com/sunsensor.htm, downloaded Feb. 5, 2004, pp. 1-3.
SunUV™, Personal UV Monitor User's Guide, APA Optics, Inc., 2003 pp. 1-52.
SunUV™, Personal UV Monitor, APA Optics, Inc., http://www.apaoptics.com/sunuv/models.html, downloaded Dec. 20, 2003.
Talking Pedometer, Sportline, Inc., Jun. 2001 (*Possibly earlier*), 1 page.
The unofficial ELSA 3D Revelator page, Dec. 30, 1999, pp. 1-15.
Top Silicon PIN Photodiode, PD93-21C, Technical Data Sheet, Everlight Electronics Co., Ltd., 2004, pp. 1-9.

(56) References Cited

OTHER PUBLICATIONS

UV Light Meter, UVA and UVB measurement, UV-340, Instruction Manual, Lutron, Jun. 2003 (*estimated*), pp. 1-5.
UV-Smart, UVA/B Monitor, Model EC-960-PW, Instruction Manual, Tanita Corporation of America, Inc., downloaded Nov. 16, 2001.
Vitaminder Personal Carb Counter, http://www.auravita.com/products/AURA/ORBU11420.asp. Downloaded Nov. 15, 2005, pp. 1-4.
Yamada et al. "Development of an eye-movement analyser possessing functions for wireless transmission and autocalibration," Med. Biol. Eng. Comput., No. 28, v.4, Jul. 28, 1990, http://link.springer.com/article/10.1007%2FBFQ2446149?LI=true, pp. 1-2.
Office Action for U.S. Appl. No. 16/429,181, dated Feb. 9, 2022.
Notice of Allowance for U.S. Appl. No. 16/429,181, dated Aug. 10, 2022.
Office Action for U.S. Appl. No. 16/424,018, dated Sep. 6, 2022.
Office Action for U.S. Appl. No. 16/424,018, dated Nov. 25, 2022.
Notice of Allowance for U.S. Appl. No. 16/424,018, dated Feb. 21, 2023.

\* cited by examiner

EYEWEAR WITH DETECTION SYSTEM

CROSS-REFERENCE TO RELATED APPLICATIONS

This application is a continuation of U.S. patent application Ser. No. 16/703,805, filed Dec. 4, 2019, now U.S. Pat. No. 11,326,941, and entitled "EYEWEAR WITH DETECTION SYSTEM," which is hereby incorporated by reference herein, and which is a continuation of U.S. patent application Ser. No. 16/426,351, filed May 30, 2019, now U.S. Pat. No. 10,539,459, and entitled "EYEWEAR WITH DETECTION SYSTEM," which is hereby incorporated by reference herein, and which is a continuation of U.S. patent application Ser. No. 16/102,859, filed Aug. 14, 2018, now U.S. Pat. No. 10,359,311, and entitled "EYEWEAR WITH RADIATION DETECTION SYSTEM," which is hereby incorporated by reference herein, and which is a continuation of U.S. patent application Ser. No. 15/343,472, filed Nov. 4, 2016, now U.S. Pat. No. 10,060,790, and entitled "EYEWEAR WITH RADIATION DETECTION SYSTEM," which is hereby incorporated by reference herein, and which is a continuation application of U.S. patent application Ser. No. 14/313,989, filed Jun. 24, 2014, now U.S. Pat. No. 9,488,520, entitled "EYEWEAR WITH RADIATION DETECTION SYSTEM," which is hereby incorporated by reference herein, and which is a continuation application of U.S. patent application Ser. No. 12/322,377, filed Feb. 2, 2009, now U.S. Pat. No. 8,770,742, entitled "EYEWEAR WITH RADIATION DETECTION SYSTEM", which is hereby incorporated herein by reference, and which is a continuation application of U.S. patent application Ser. No. 11/078,855, filed Mar. 11, 2005, now U.S. Pat. No. 7,500,746, entitled "EYEWEAR WITH RADIATION DETECTION SYSTEM", which claims priority to: (i) U.S. Provisional Patent Application No. 60/562,798, filed Apr. 15, 2004, entitled "EYEWEAR WITH ULTRAVIOLET DETECTION SYSTEM," and which is hereby incorporated herein by reference; (ii) U.S. Provisional Patent Application No. 60/583,169, filed Jun. 26, 2004, entitled "ELECTRICAL COMPONENTS FOR USE WITH EYEWEAR, AND METHODS THEREFOR," and which is hereby incorporated herein by reference; (iii) U.S. Provisional Patent Application No. 60/592,045, filed Jul. 28, 2004, entitled "EYEGLASSES WITH A CLOCK OR OTHER ELECTRICAL COMPONENT," and which is hereby incorporated herein by reference; (iv) U.S. Provisional Patent Application No. 60/605,191, filed Aug. 28, 2004, entitled "ELECTRICAL COMPONENTS FOR USE WITH EYEWEAR, AND METHODS THEREFOR," and which is hereby incorporated herein by reference; (v) U.S. Provisional Patent Application No. 60/618,107, filed Oct. 12, 2004, and entitled "TETHERED ELECTRICAL COMPONENTS FOR EYEGLASSES," which is hereby incorporated herein by reference; (vi) U.S. Provisional Patent Application No. 60/620,238, filed Oct. 18, 2004, entitled "EYEGLASSES WITH HEARING ENHANCED AND OTHER AUDIO SIGNAL-GENERATING CAPABILITIES," and which is hereby incorporated herein by reference; (vii) U.S. Provisional Patent Application No. 60/647,836, filed Jan. 31, 2005, and entitled "EYEGLASSES WITH HEART RATE MONITOR," which is hereby incorporated herein by reference; and (viii) U.S. Provisional Patent Application No. 60/647,826, filed Jan. 31, 2005, and entitled "EYEWEAR WITH ELECTRICAL COMPONENTS," which is hereby incorporated herein by reference.

In addition, this application is related to: (i) U.S. patent application Ser. No. 10/822,218, filed Apr. 12, 2004, now U.S. Pat. No. 7,792,552, and entitled "EYEGLASSES FOR WIRELESS COMMUNICATIONS," which is hereby incorporated herein by reference; (ii) U.S. patent application Ser. No. 10/964,011, filed Oct. 12, 2004, now U.S. Pat. No. 7,192,136, and entitled "TETHERED ELECTRICAL COMPONENTS FOR EYEGLASSES," which is hereby incorporated herein by reference; (iii) U.S. patent application Ser. No. 11/006,343, filed Dec. 7, 2004, now U.S. Pat. No. 7,116,976, and entitled "ADAPTABLE COMMUNICATION TECHNIQUES FOR ELECTRONIC DEVICES," which is hereby incorporated herein by reference; and (iv) U.S. patent application Ser. No. 11/078,857, filed Mar. 11, 2005, and entitled "RADIATION MONITORING SYSTEM," which is hereby incorporated herein by reference.

BACKGROUND OF THE INVENTION

It is common for people to be exposed to various types of radiation. Often excessive exposure to radiation can be hazardous to one's health. One type of radiation that frequently raises a health concern is ultraviolet (UV) radiation. UV radiation is subdivided into three types: UV-A, UV-B, and UV-C. UV-C radiation has wavelengths in the range of 200 to 285 nanometers (nm) and is totally absorbed by the earth's atmosphere. UV-B, from about 285 to 318 nm, is known to cause skin cancer in humans. UV-A, from about 315 to 400 nm, is mostly responsible for tanning. However, UV-A has also been found to play some role in skin cancer and is the cause of eye cataracts, solar retinitis, and corneal dystrophies.

Although several UV radiation measuring and warning instruments have been developed and made commercially available, these instruments are disadvantageous for various reasons. One disadvantage is that the instruments are often a stand alone, special purpose device. As a result, a user must separately wear the special purpose device, which can be intrusive and often inconvenient. Another disadvantage is that those instruments, even if separate but attachable to other devices, hinder or impede the design for the devices.

Thus, there is a need for improved approaches to measure and inform persons of UV radiation levels.

SUMMARY OF THE INVENTION

Eyewear having monitoring capability, such as for radiation or motion, is disclosed. Radiation, such as ultraviolet (UV) radiation, infrared (IR) radiation or light, can be measured by a detector. The measured radiation can then be used in providing radiation-related information to a user of the eyewear. Motion can be measure by a detector, and the measured motion can be used to determine whether the eyewear is being worn.

In one embodiment, the invention pertains to eyewear having radiation monitoring capability. Radiation, such as ultraviolet (UV) radiation, infrared (IR) radiation or light, can be measured by a detector. The measured radiation can then be used in providing radiation-related information to a user of the eyewear. Advantageously, the user of the eyewear is able to easily monitor their exposure to radiation.

In one embodiment, all components for monitoring radiation can be integrated with the eyewear, such as the frame (e.g., a temple of the frame) of the eyewear. Since any of the components provided can be integrated with the eyewear, the disturbance to design features of the eyewear can be reduced. As an example, the eyewear normally includes a pair of temples, and the components for monitoring radiation can be embedded within one or both of the temples. In one implementation, all components for monitoring radiation are integrated into a temple of the frame of the eyewear. As an example, these components can be formed together on a substrate as a module.

In one embodiment, the eyewear includes a detector, electrical circuitry and an output device. The eyewear can also include one or both of a battery and a solar cell to provide power to the electrical circuitry and possibly other components. Further, the eyewear can also include one or more additional sensors. Still further, the eyewear can also include communication capabilities.

The invention can be implemented in numerous ways, including as a system, device, apparatus, and method. Several embodiments of the invention are discussed below.

As eyewear, one embodiment of the invention can, for example, include at least: a frame including at least a first temple and a second temple; a radiation detector for sensing an amount of radiation; and an electronic circuit operatively connected to the radiation detector. The electronic circuit provides at least radiation information based on at least the amount of radiation sensed by the radiation detector. The radiation detector and the electronic circuit are at least partially internal to the first temple of the frame.

As eyewear, another embodiment of the invention can, for example, include at least: a frame including at least a first temple and a second temple; a radiation detector for sensing an amount of radiation; and an electronic circuit operatively connected to the radiation detector. The electronic circuit provides at least radiation information based on at least the amount of radiation sensed by the radiation detector. The radiation detector includes at least an optical filter for reducing passage of predetermined undesired radiation therethrough, and a photodetector for sensing at least a portion of radiation that passes through the optical filter. The photodetector and the electronic circuit are internal to the frame. Further, the frame has an opening adjacent the optical filter to allow at least a portion of the radiation that passes through the optical filter to impinge on the photodetector.

As a consumer product for monitoring radiation, one embodiment of the invention can, for example, include at least: a radiation detector for sensing an amount of radiation; and an electronic circuit operatively connected to the radiation detector. The electronic circuit provides at least radiation information based on at least the amount of radiation sensed by the radiation detector. The radiation detector and the electronic circuit are at least partially embedded in the consumer product. The radiation being detected by the radiation detector is principally solar radiation from the sun. The consumer product can also be wearable by a user.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION OF THE INVENTION

Figure 1:
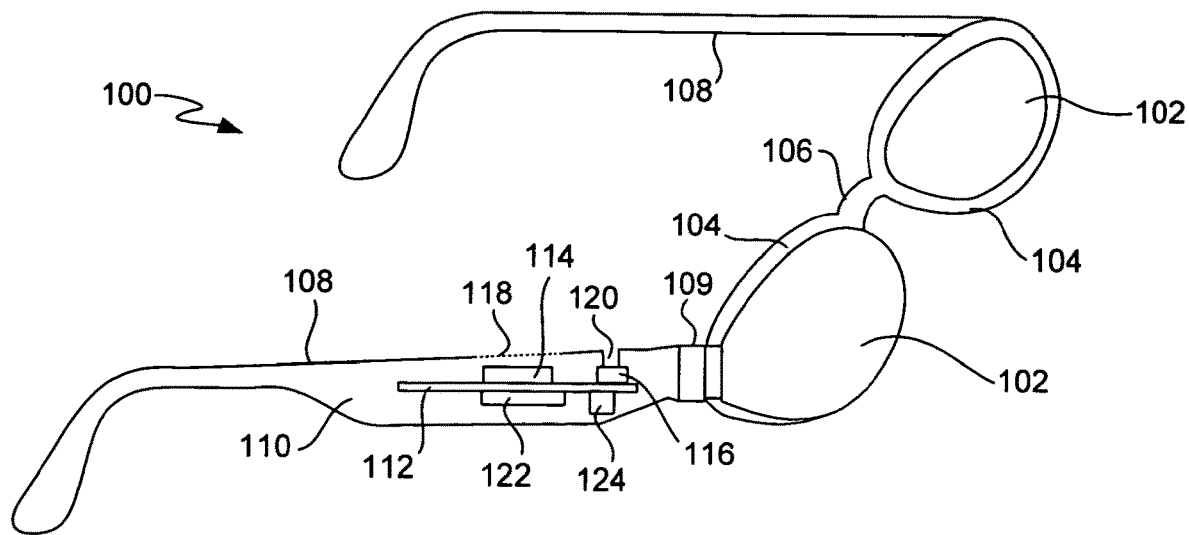
FIG. 1 is a perspective view of UV monitoring glasses according to one embodiment of the invention.

Eyewear having monitoring capability, such as for radiation or motion, is disclosed. Radiation can be measured by a detector. The measured radiation can then be used in providing radiation-related information to a user of the eyewear. Motion can be measured by a detector, and the measured motion can be used to determine whether the eyewear is being worn.

In one embodiment, an electronic circuit having radiation monitoring capability. Radiation, such as ultraviolet (UV) radiation, infrared (IR) radiation or light, can be measured by the electronic circuit. The measured radiation can then be used in providing radiation-related information to a user of the electronic circuit In one embodiment, all components for monitoring radiation can be integrated with eyewear, such as a frame (e.g., a temple of the frame) of the eyewear. Since any of the components provided can be integrated with the eyewear, the disturbance to design features of the eyewear can be reduced. As an example, the eyewear normally includes a pair of temples, and the components for monitoring radiation can be embedded within one or both of the temples. In one implementation, all components for monitoring radiation are integrated into a temple of the frame of the eyewear. As an example, these components can be formed together on a substrate as a module.

In one embodiment, the eyewear includes a detector, electrical circuitry and an output device. The eyewear can also include one or both of a battery and a solar cell to provide power to the electrical circuitry and possibly other components. Further, the eyewear can also include one or more additional sensors. Still further, the eyewear can also include communication capabilities.

In another embodiment, some or all of the components for monitoring radiation can be partially or completely tethered to the eyewear. In still another embodiment, some or all of one or more auxiliary sensors used therewith could be partially or completely tethered to the eyewear. Tethering components allows for increased design freedom with the eyewear as well as additional area with which to house the components.

The eyewear can contain lenses, either vision corrective lenses or non-corrective lenses. Examples of eyewear using corrective lenses include, for example, prescription glasses, bi-focal glasses, reading glasses, driving glasses, and progressive glasses. Examples of eyewear, using corrective or non-corrective lenses, are sunglasses, fit-over glasses, safety glasses, sports glasses, swim masks or goggles and ski goggles. The eyewear can also include wrap-around glasses (with wrap-around lenses), fit-over glasses, or auxiliary frames (which attach to existing frames). Still further, the eyewear can include a strap for glasses, such as a strap to hold glasses on one's head. The strap can include some or all of the components for monitoring radiation, such components can be attached or at least partially embedded in the strap.

Embodiments of the invention are discussed below with reference to FIGS. 1-23G. However, those skilled in the art will readily appreciate that the detailed description given herein with respect to these figures is for explanatory purposes as the invention extends beyond these limited embodiments. Although much of the discussion below pertains to monitoring of UV radiation, it should be understood that the invention is also applicable to other types of radiation (infrared, x-rays, etc.).

FIG. 1 is a perspective view of UV monitoring glasses 100 according to one embodiment of the invention. The UV monitoring glasses 100 include a frame and a pair of lenses 102. The frame has lens holders 104 that hold the lenses 102 in position. The frame also has a bridge 106. The UV monitoring glasses 100 also include a pair of temples (or arms) 108. The temples 108 are considered part of the frame. As shown in FIG. 1, each of the temples 108 is coupled to the frame by a hinge 109. In one embodiment, the temples 108 can be removed from the frame. At least one of the temples 108 includes an internal cavity 110. Within the internal cavity 110 is a circuit board 112. The circuit board 112 can serve as a substrate. The circuit board 112 can have or couple to a solar cell 114 and UV detector 116 which are also at least primarily provided within the internal cavity 110. The circuit board 112 could include a battery (not shown) in addition to or alternative to the solar cell 114. The temple 108 having the cavity region 110 includes an opening 118 for the solar cell 114 (if provided) and an opening 120 for the UV detector 116. In addition, the circuit board 112 can further include or couple to circuitry 122 and a display device 124. For example, the display device 124 can be either a liquid-crystal display (LCD) or a Light-Emitting Diode (LED) display having one or more LED components, either of which can be controlled by the circuitry 122. The solar cell 114 can receive light via the opening 118 so as to provide power to the circuit board 112. The UV detector 116 can receive light via the opening 120. The UV detector 116 is used to provide an indication of UV radiation. The indication of UV radiation detected by the UV detector 116 can be processed by the circuitry 122 to produce an output at the display device 124.

Figure 2A:
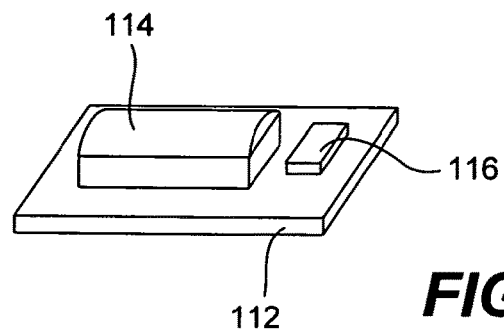
FIGS. 2A and 2B are diagrams of a circuit board according to one embodiment of the invention.
Figure 2B:
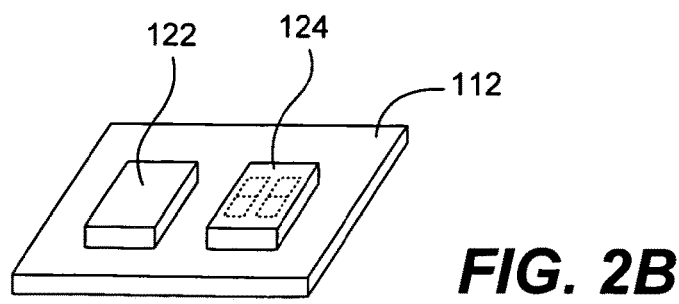

FIGS. 2A and 2B are diagrams of the circuit board 112 according to one embodiment of the invention. In one embodiment, the circuit board includes at least one electronic component.

FIG. 2A shows a first side of the circuit board 112. Typically, the first side would be positioned adjacent a top side or outer side of the temple 108. As shown in FIG. 2A, the first side of the circuit board 112 has the solar cell 114 and the UV detector 116 attached thereto. The first side of the circuit board 112 should be exposed at least partially to external light (e.g., sunlight). Hence, the openings 118 and/or 120 of the temple 108 shown in FIG. 1 can provide openings so that light can impinge upon the solar cell 114 and the UV detector 116.

FIG. 2B shows a second side of the circuit board 112. The second side of the circuit board 112 can be a bottom side or inner side of the temple 108. As shown in FIG. 2B, the second side of the circuit board 112 can have the circuitry 122 and the display device 124 attached thereto. As previously noted, the display device 124 can be a LED or LCD display. As depicted in FIG. 2B, the display device 124 can be a multi-character display. Alternatively, the display device 124 can be a multi-color display, such as provided by a color LCD or a plurality of different color LEDs (e.g., a red LED, yellow LED and green LED). The display device 124 can also be a multi-symbol display. Although not shown in FIG. 1, the UV monitoring glasses 100 can further include an opening or transparent portion at the temple 108 proximate to the display device 124 so that an output from the display device 124 can be visible to a user of the UV monitoring glasses 100.

Figure 3:
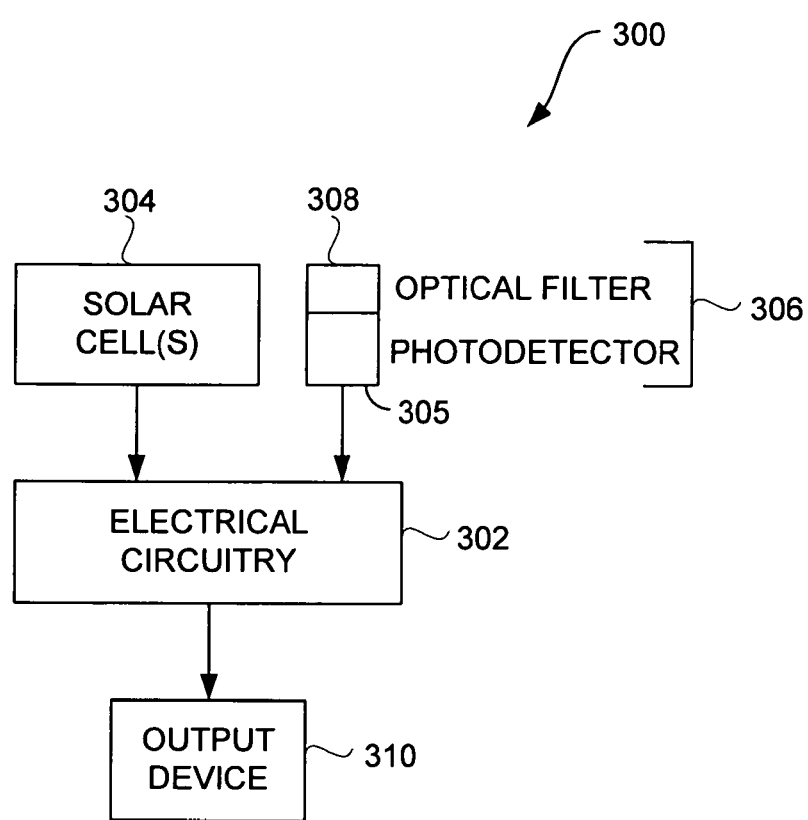
FIG. 3 is a block diagram of a UV monitoring system according to one embodiment of the invention.

FIG. 3 is a block diagram of a UV monitoring system 300 according to one embodiment of the invention. The UV monitoring system 300 can be embedded within (i.e., internal to) the housing (i.e., frame) of a pair of glasses. Glasses refer to eyewear.

The UV monitoring system 300 includes electrical circuitry 302. The electrical circuitry 302 can be one or more electrical components, such as integrated circuits, analog components, and/or digital components. One or more solar cells 304 provide power to the electrical circuitry 302. In other words, when light impinges upon the one or more solar cells 304, power is produced and supplied to the electrical circuitry 302. The electrical circuitry 302 receives a UV level indication from a UV detector 306. In one embodiment, the UV detector 306 includes a photodetector 305 and an optical filter 308. The optical filter 308 can be integral with or positioned proximate to the photodetector 305 so that the optical filter 308 passes radiation associated with the ultraviolet wavelength range, and such radiation is supplied to the photodetector 305. As a result, the UV level indication produced by the UV detector 306 is an indication of the UV radiation impinging upon glasses or the user thereof. The electrical circuitry 302 receives the UV level indication from the UV detector 306 and determines whether an output should be signaled by an output device 310. The output device 310 can take a variety of different forms. For example, the output device 310 can be a display device, such as a LED or LCD display. A display device can produce a visual output. The output device 310 can also be a speaker or a vibration device. The speaker can produce an audio output. For example, the audio output can be a buzzing sound, a beep or a synthesized voice message.

Figure 4A:
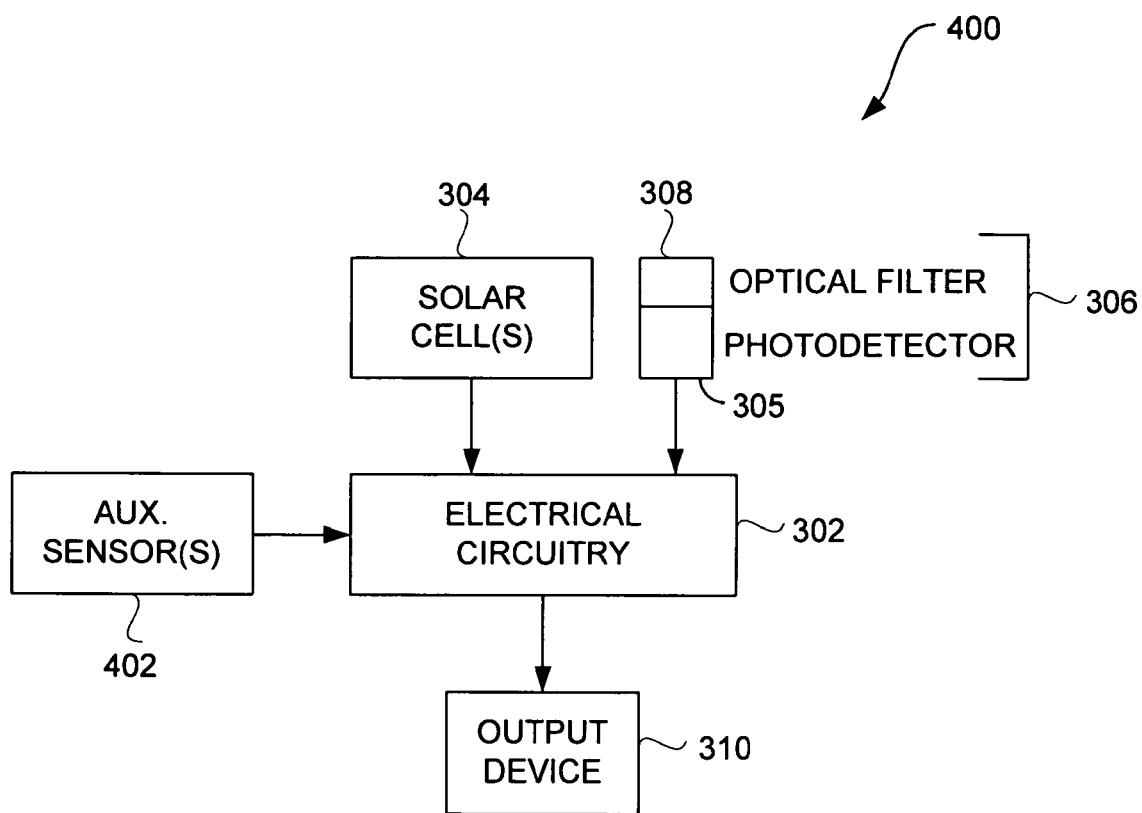
FIG. 4A is a block diagram of a UV monitoring system according to another embodiment of the invention.

FIG. 4A is a block diagram of a UV monitoring system 400 according to another embodiment of the invention. The UV monitoring system 400 includes the electrical circuitry 302, the one or more solar cells 304, the UV detector 306, and the output device 310 shown in FIG. 3. In addition, the UV monitoring system 400 further includes or makes use of one or more auxiliary sensors 402. The one or more auxiliary sensors 402 can provide additional sensor information to the electrical circuitry 302. This additional sensor information can affect the output being provided at the output device 310. For example, the additional sensor information could be used to provide additional output data or could be used to modify the output data associated with the UV level indication provided by the UV detector 306.

Figure 4B:
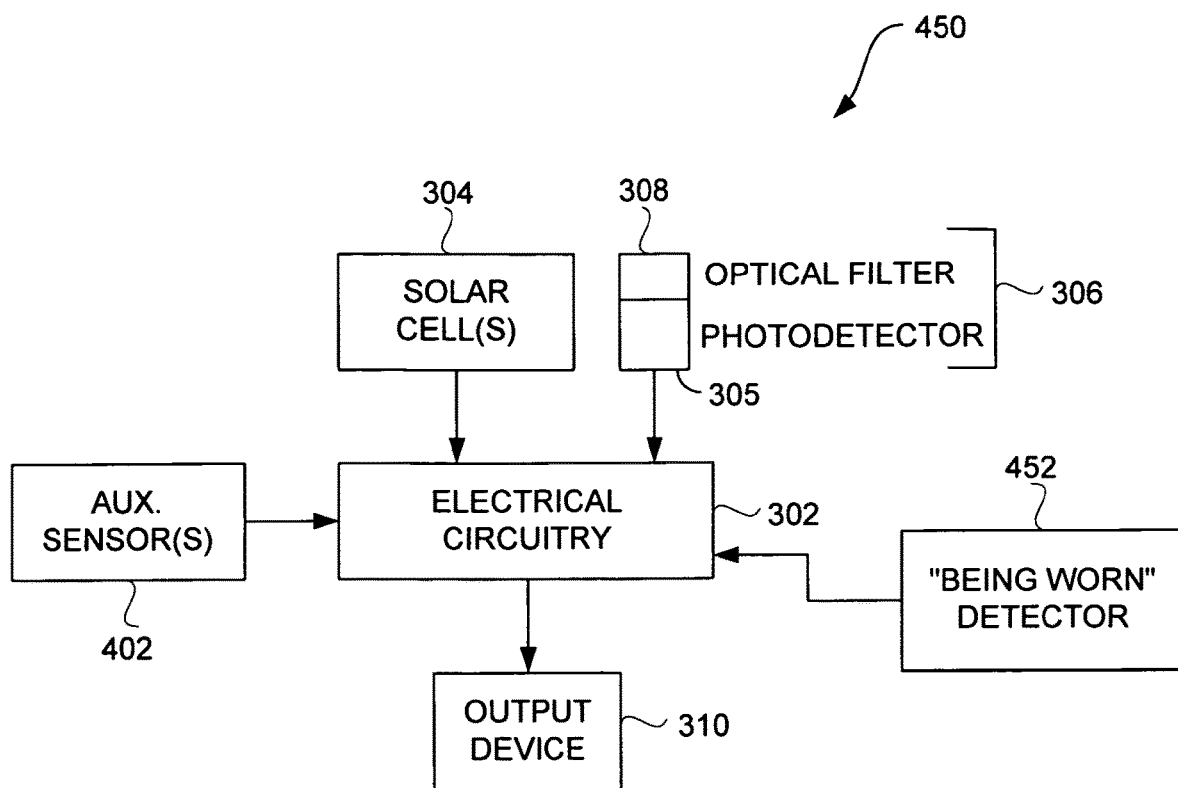
FIG. 4B is a block diagram of a UV monitoring system according to still another embodiment of the invention.

FIG. 4B is a block diagram of a UV monitoring system 450 according to still another embodiment of the invention. The UV monitoring system 450 is generally similar to the UV monitoring system 400 shown in FIG. 4, but further includes or makes use of a "being worn" detector 452. The UV monitoring system 450 can be embedded within (i.e., internal to) the housing (i.e., frame) of a pair of glasses. The "being worn" detector 452 would indicate whether the glasses are being worn by its user. For example, the "being worn" detector 452 can be performed using a thermal sensor, a motion detector, a stress sensor or a switch. Although the "being worn" detector 452 is shown separate from the auxiliary sensors 402, it should be understood that the "being worn" detector 452 can be considered one type of auxiliary sensor.

Figure 4C:
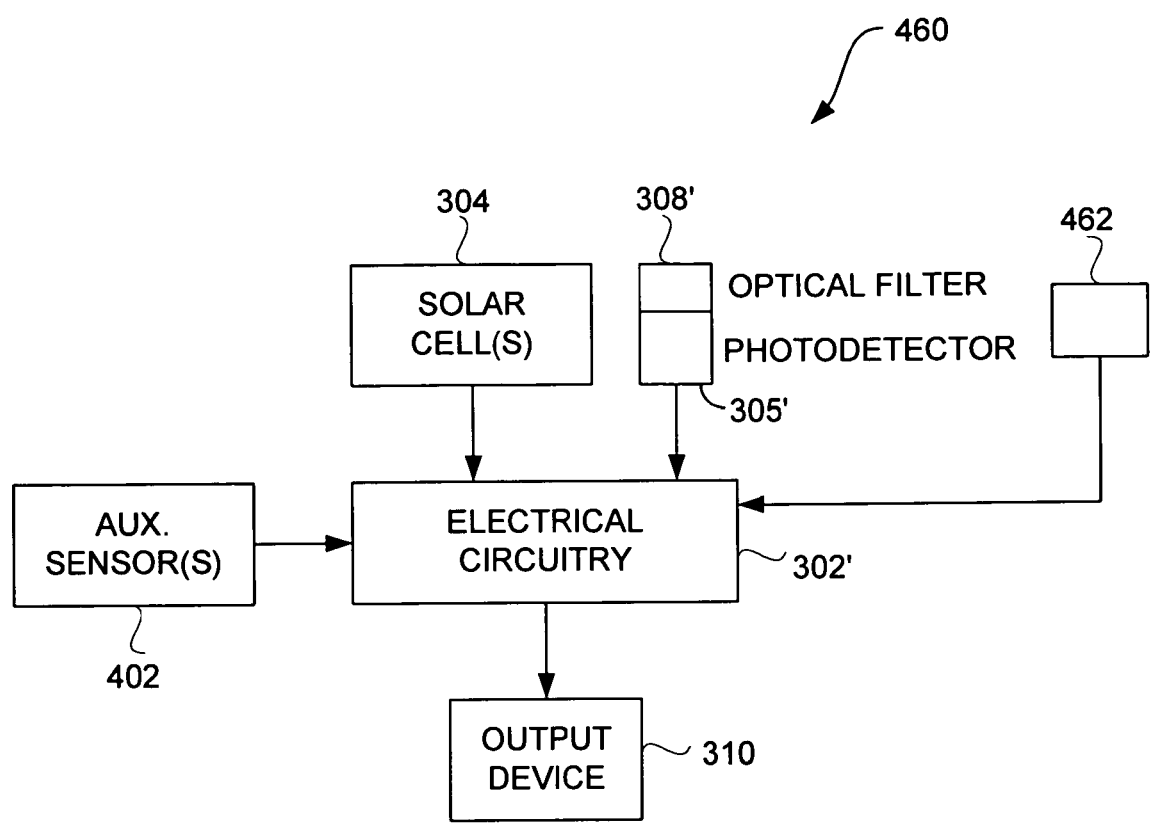
FIG. 4C is a block diagram of a UV monitoring system according to yet another embodiment of the invention.

FIG. 4C is a block diagram of a UV monitoring system 460 according to yet another embodiment of the invention. The UV monitoring system 460 is generally similar to the UV monitoring system 400 shown in FIG. 4A, but further includes a photodetector 462. Also, in this embodiment, the optical filter 308' blocks UV light and passes other light through to the photodetector 305'. As an example, the optical filter 308' can be a thin sheet or coating of polycarbonate. In this embodiment, the photodetector 305' provides an indication of non-UV light, and the photodetector 462 provides an indication of total light. The electrical circuitry 302' receives the indication of non-UV light and the indication of total light. By subtracting the indication of non-UV light from the indication of total light, the electrical circuitry 302' determines an indication of UV light. In one embodiment, the photodetectors 305' and 462 can be Silicon (Si) photodetectors. The electrical circuitry 302' determines whether an output should be signaled by an output device 310 based on the UV level indication. As previously noted, the output device 310 can take a variety of different forms.

Figure 4D:
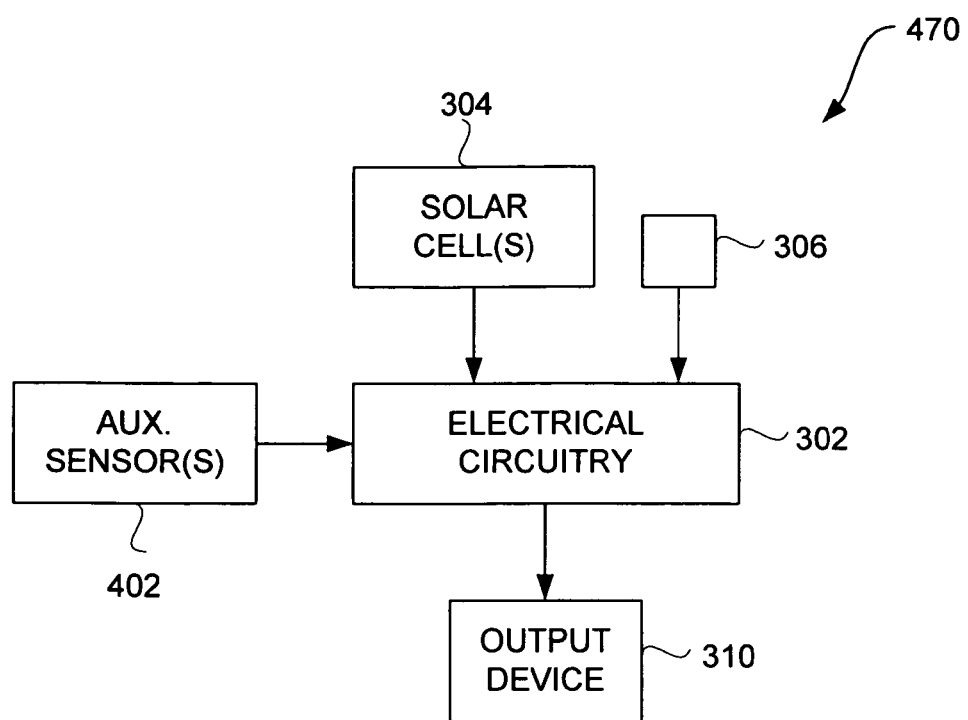
FIG. 4D is a block diagram of a UV monitoring system according to yet another embodiment of the invention.

FIG. 4D is a block diagram of a UV monitoring system 470 according to still yet another embodiment of the invention. The UV monitoring system 470 includes the electrical circuitry 302, the one or more solar cells 304, the UV detector 306 and the output device 310 shown in FIG. 3. In this embodiment, the UV detector 306 measures the UV level indication directly, without the need for an additional optical filter. For example, the UV detector 306 can be a Gallium Nitride (GaN) photodetector since such has a sensitivity to UV radiation. As another example, the UV detector 306 can be a Silicon Carbide (SiC) photodetector since such also has a sensitivity to UV radiation. Silicon Carbide (SiC) detectors may also be suitable for use to detect other types of radiation besides UV. The electrical circuitry 302 receives the UV level indication from the UV detector 306 and determines whether an output should be signaled by the output device 310. As noted above, the output device 310 can take a variety of different forms.

Figure 5:
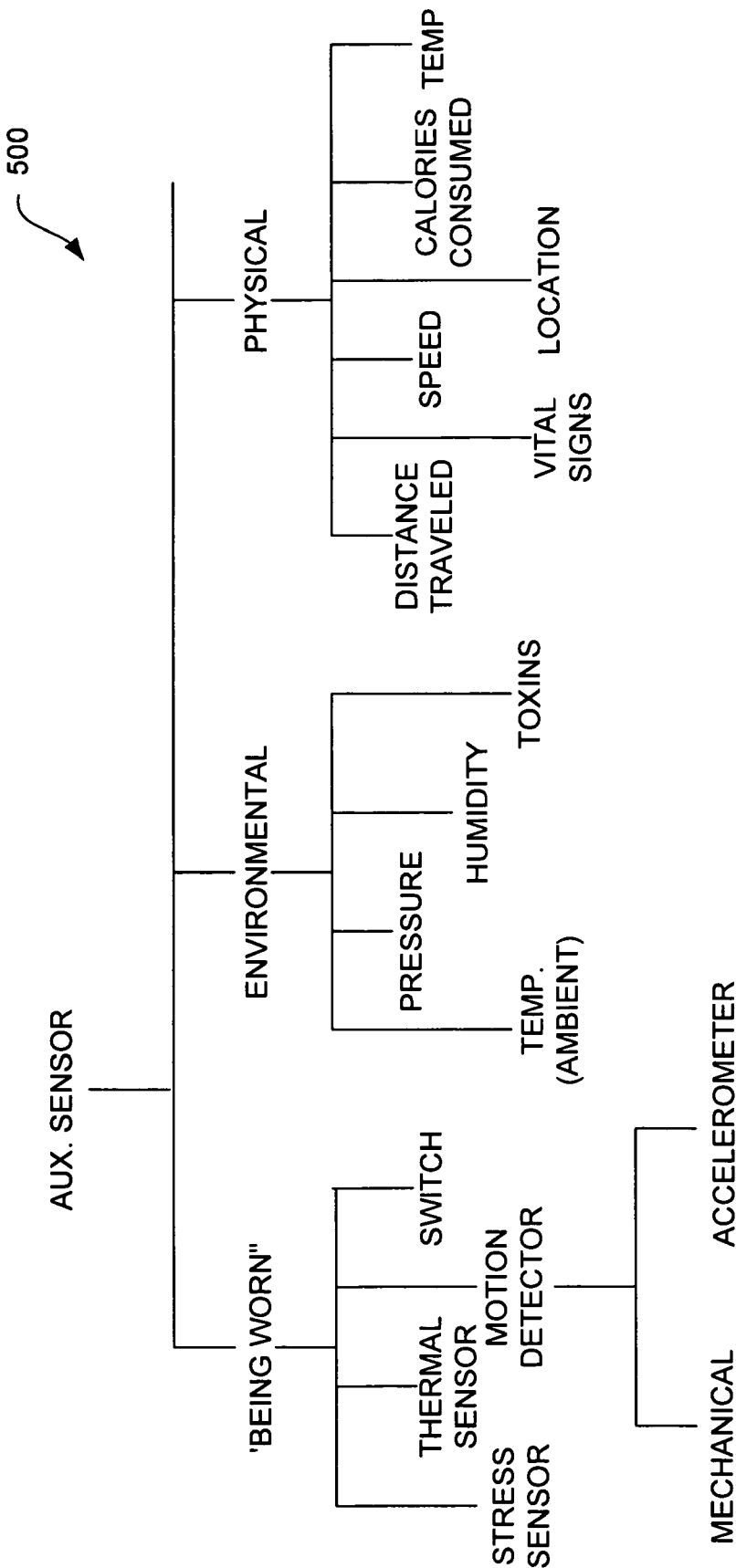
FIG. 5 is a chart that depicts examples of auxiliary sensors that can be utilized as the one or more auxiliary sensors shown in FIGS. 4A-4D.

The one or more auxiliary sensors 402 utilized in the UV monitoring system 400 shown in FIGS. 4A-4D can vary depending upon application. FIG. 5 is a chart 500 that depicts examples of auxiliary sensors that can be utilized as the one or more auxiliary sensors 402 shown in FIGS. 4A and 4D.

The chart 500 indicates that one type of auxiliary sensor is a "being worn" sensor. The "being worn" sensor would indicate whether the glasses are being worn by its user. The "being worn" sensor can be performed using, for example, a thermal sensor, a motion detector, a stress sensor or a switch.

In one embodiment, a motion detector is used as a "being worn" sensor. A threshold can be set, such that if the amount of motion detected exceeds the threshold, the eyewear is assumed to be worn. The motion detector can, for example, be achieved by a mechanical means or an accelerometer.

In another embodiment, the "being worn" sensor includes one or more thermal sensors. In the case where two sensors are used, one sensor can be at approximately the middle of a temple, such as in a region that touches the head of the user wearing the glasses, and the other sensor can be positioned at the end of the same temple close to the hinge. If the temperature differential between the two sensors is beyond a certain preset value, the eyewear would be assumed to be worn.

In yet another embodiment, the "being worn" sensor includes a stress sensor at the hinge of the temple. The assumption is that when the eyewear is worn, the hinge is typically slightly stretched because typically the width of the head of the user is slightly wider than the width between the temples when the two temples are in the extended positions. If the value of the stress sensor is beyond a certain preset value, the glasses would be assumed to be worn.

In still yet another embodiment, the "being worn" sensor can be implemented as a switch. For example, the switch can utilize optical, magnetic or mechanical means. In one embodiment, the switch can be positioned at the temple of the eyewear, such as a forward end of the temple proximate to a corresponding lens holder. Different embodiments of such sensors is also described in U.S. Provisional Patent Application No. 60/583,169, filed Jun. 26, 2004, entitled "ELECTRICAL COMPONENTS FOR USE WITH EYE- WEAR, AND METHODS THEREFOR," which has been incorporated herein by reference, see, e.g., section entitled "EYEGLASSES WITH USER INPUT CAPABILITY."

Another type of auxiliary sensor is an environmental sensor. The environmental sensor can sense environmental conditions, such as one or more of temperature (e.g., ambient temperature), pressure, humidity and toxins (e.g., chemicals, radiation, etc.).

Still another type of auxiliary sensor is a physical sensor. The physical sensor can sense physical conditions of the user of the glasses. Examples of physical sensors include sensing one or more of distance traveled, location, speed, calories consumed, temperature, alertness, and vital signs (e.g., heart rate, blood pressure, etc.) associated with the user of the glasses. The distance traveled could represent the horizontal distance traveled or the vertical distance (i.e. elevation) traveled. As one example, a pedometer can provide an estimate of distance traveled The speed can be acquired or determined, such as the rate of movement along the horizontal distance traveled and/or the vertical distance. As another example, calories consumed can be determined (e.g., estimated) based on various physical and/or environmental conditions that can be measured or determined. Still other physical sensors can sense emotions of the user. For example, the physical sensor could sense whether the user is calm, excited, happy, sad, angry, etc. The physical sensor can also more generally sense user activity level. As an example, the user activity level can be used to provide a lifestyle indication. For example, a lifestyle indication might show that the user was active today or, alternatively, lazy today. Such a lifestyle indication can be displayed as a text or graphic symbol to let the user or others aware of the activity level.

In one embodiment, one particular type of physical sensor is a heart-beat sensor. The heart-beat sensor measures the heart beat of the wearer of the eyewear. One implementation for the heart-beat sensor utilizes an infrared emitter and an infrared detector as a component. The infrared emitter can be a LED and the infrared detector can be a photodiode with an infrared filter. The component can be located at a temple of the eyewear, with both the emitter and the detector both facing the user when the eyewear is worn. In operation, the infrared emitter shines infrared radiation towards the user, and the detector captures the infrared signals reflected back by the skin of the user. The magnitude of the reflected signals depends on the amount of blood flowing below the skin, which, in turn, depends on the heart beat. The rate of emission by the emitter and reception by the detector can be in a frequency range much higher than the heart beat, such as three thousands cycles per second. And the signals from the detector can be low-pass filtered before they are measured to identify the heart beat of the user. For example, the low-pass filter can be centered at 1 Hz.

In should be understood that the sensors might rely on more than one measured criteria. The one or more measured criteria might be used to determine the sensor output. The determination of the sensor output can involve estimation or prediction.

The auxiliary sensors can be provided in a redundant or fault-tolerant manner. For example, sensors can be provided in pairs. When one sensor of a pair malfunctions, the other one can replace it. In another embodiment, any of the auxiliary sensor information can be processed in a differential manner to examine changes to the auxiliary sensor information. The auxiliary sensors can by powered by a battery, solar energy, or kinetic energy. For reduced power consumption, the auxiliary sensors can remain in a low- power state unless data is being acquired by the auxiliary sensors. In yet another embodiment, two or more of the auxiliary sensors can communicate with one another (wired or wirelessly) to exchange data or control information.

In general, the auxiliary sensors can be fully or partially embedded in the eyewear or a base tethered to the eyewear. Alternatively, one or more of the auxiliary sensors can be separate from the eyewear, or any base tethered thereto, and wirelessly communicate with the eyewear or base.

Figure 6:
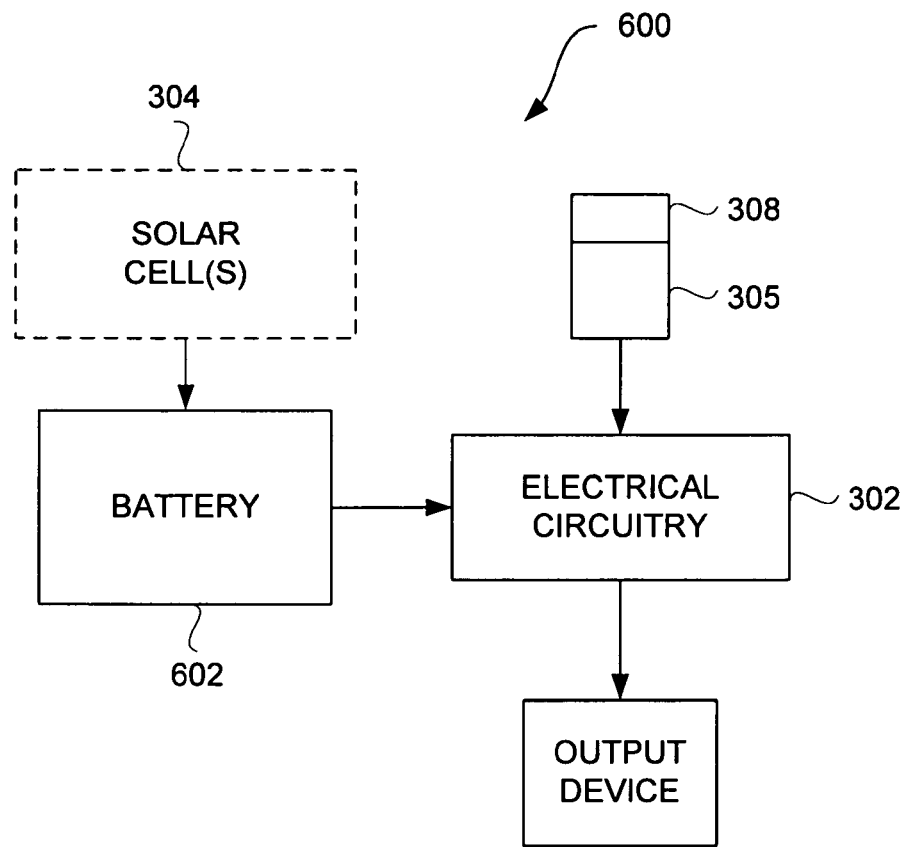
FIG. 6 is a block diagram of a UV monitoring system according to one embodiment of the invention.

FIG. 6 is a block diagram of a UV monitoring system 600 according to one embodiment of the invention. The UV monitoring system 600 is generally similar to the UV monitoring systems illustrated in FIGS. 3-4D. However, in the UV monitoring system 600, a battery 602 provides power to the electrical circuitry 302. In other words, in this embodiment, the one or more solar cells 304 are optional. The UV monitoring system 600 can operate without the need for any light to impinge upon the one or more solar cells 304. If the UV monitoring system 600 does include the one or more solar cells 304, the power produced by the one or more solar cells 304 can be coupled to the battery 602 so as to recharge the battery. The battery 602 also allows the electrical circuitry 302 to maintain data even while no light is present (e.g., if a volatile memory is used to store data). The ability to maintain data (such as in a memory device) can be advantageous. For example, the UV monitoring system 600 may desire to output information over longer durations of time, or may desire to process data in a differential manner. The UV monitoring system 600 can also further include one or more auxiliary sensors.

Figure 7A:
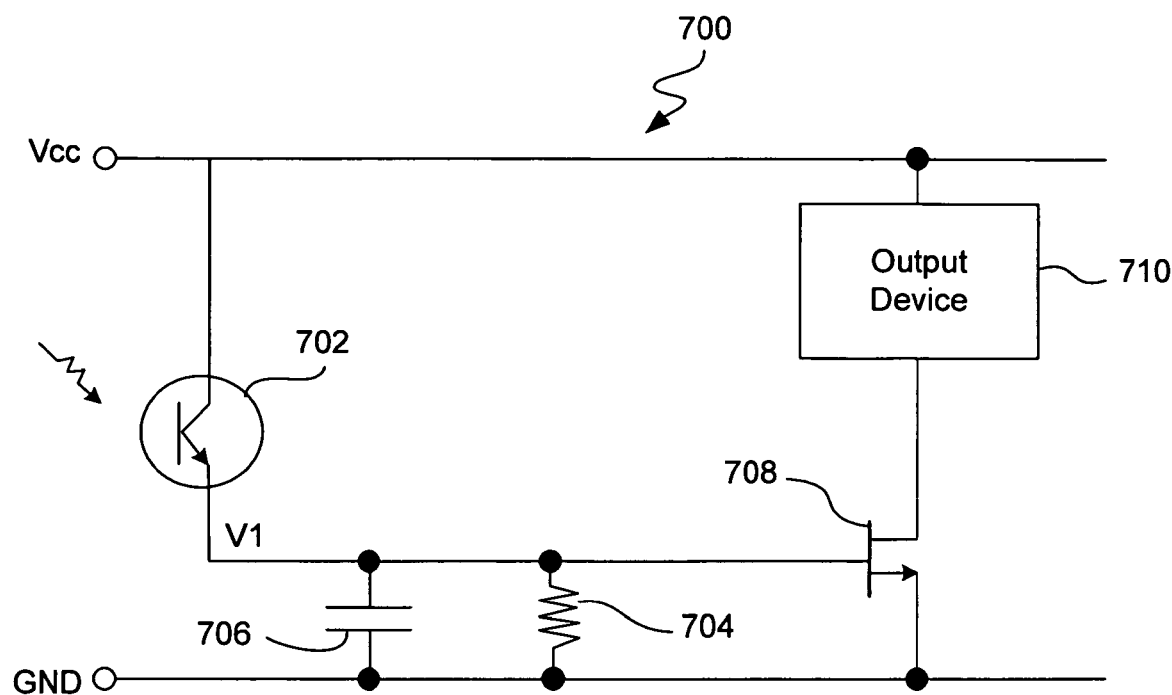
FIG. 7A is a schematic diagram of a UV monitoring circuit according to one embodiment of the invention.

FIG. 7A is a schematic diagram of a UV monitoring circuit 700 according to one embodiment of the invention. The UV monitoring circuit 700 includes a phototransistor 702. Although the phototransistor 702 may itself serve as a UV detector, in some implementations, an optical filter (not shown) would limit the radiation that impinges on the phototransistor 702, in which case the phototransistor 702 together with the optical filter serves as the UV detector. A collector terminal of the phototransistor 702 is coupled to a power source Vcc. The power source Vcc can be provided by a battery or solar cell(s). An emitter terminal of the phototransistor 702 is coupled to a first end of a resistor 704, a first end of the capacitor 706 and a gate terminal of a transistor 708. As an example, the transistor 708 can be an n-channel metal-oxide-semiconductor, enhancement-mode, field-effect transistor (MOSFET). A second end of the resistor 704, a second end of the capacitor 706 and a source terminal of the transistor 708 are coupled to ground. An output device 710 couples between the power source Vcc and a drain terminal of the transistor 708. As sufficient radiation, such as UV radiation, impinges on the phototransistor 702, the phototransistor 702 conducts so that the emitter terminal of the phototransistor 702 outputs the voltage V1 by coupling to the power source Vcc through the phototransistor 702. The voltage V1 is dependent on the amount of UV radiation that impinges on the phototransistor 702. The capacitor 706 then charges up in accordance with a time constant determined by the capacitance of the capacitor 706 and the resistance of the resistor 704. When the voltage V1 exceeds a turn-on voltage for the transistor 708, the transistor 708 conducts and the output device 710 is activated. For example, the output device 710 can indicate that the UV monitoring circuit has detected exposure to a large amount of UV radiation. The amount of UV radiation exposure being detected can vary depending on the capacitance of the capacitor 706 and the resistance of the resistor 704.

Figure 7B:
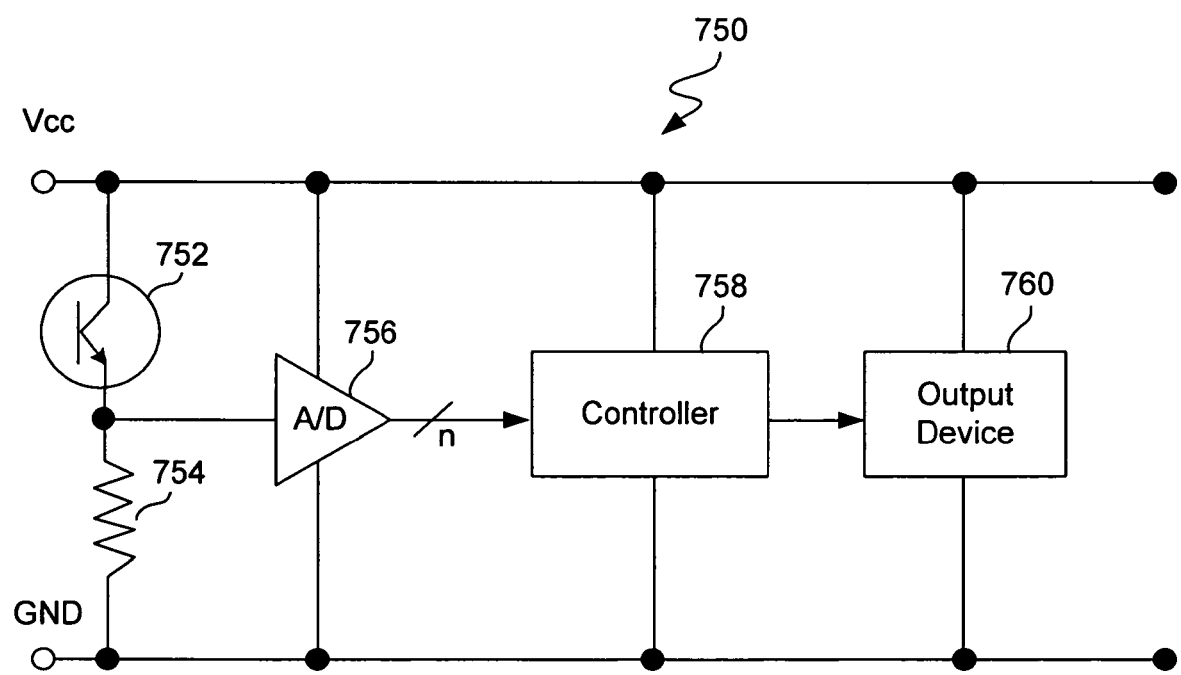
FIG. 7B is a schematic diagram of a UV monitoring circuit according to another embodiment of the invention.

FIG. 7B is a schematic diagram of a UV monitoring circuit 750 according to another embodiment of the invention. The UV monitoring circuit 750 includes a phototransistor 752. Although the phototransistor 752 may itself serve as a UV detector, in some implementations, an optical filter (not shown) would limit the radiation that impinges on the phototransistor 752 in which case the phototransistor 752 together with the optical filter serves as the UV detector. A collector terminal of the phototransistor 752 is coupled to a power source Vcc. The power source Vcc can be a battery or solar cell(s). An emitter terminal of the phototransistor 752 is coupled to a first end of a resistor 754 as well as to an input to an analog-to-digital (A/D) converter 756. The second end of the resistor 754 couples to ground. The A/D converter 756 converts the voltage level at the emitter terminal of the phototransistor 752 to a digital voltage value having n bits. The digital voltage value represents the UV radiation impinging on the phototransistor 752. The digital voltage value is supplied to a controller 758. The controller 758 can, for example, be a microcontroller. In one embodiment, the microcontroller is a microprocessor. An output device 760 couples between the power source Vcc and ground. The output device 760 also couples to an output terminal of the controller 758. As sufficient radiation, such as UV radiation, impinges on the phototransistor 752, the phototransistor 752 conducts so that a voltage is supplied to the A/D converter 756 which produces the corresponding digital voltage value. The digital voltage value is dependent on the amount of UV radiation that impinges on the phototransistor 752. The controller 758 can then determine whether to activate the output device 760. For example, controller 758 can activate the output device 760 to indicate that the UV monitoring circuit 750 has detected (i) current exposure to a substantial (e.g., large) amount of UV radiation (e.g., amount of UV radiation greater than a threshold amount), and/or (ii) exposure to a substantial (e.g., large) amount of UV radiation accumulated over a time period (e.g., accumulated amount of UV radiation greater than a threshold amount). Although not shown, the controller 758 can also receive sensor information from one or more other auxiliary sensors and signal other types of outputs via the output device 760.

Figure 7C:
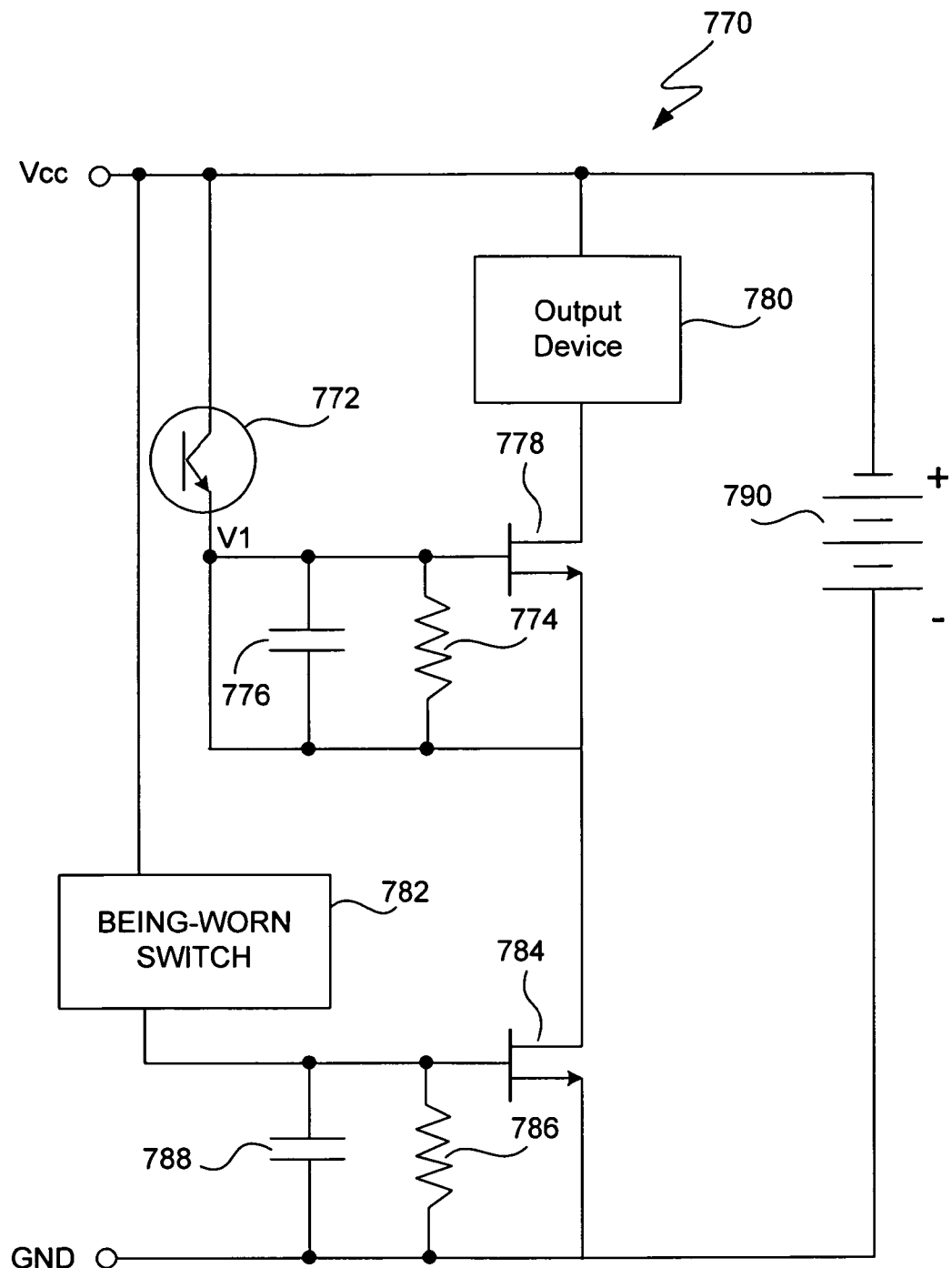
FIG. 7C is a schematic diagram of a UV monitoring circuit according to yet another embodiment of the invention.

FIG. 7C is a schematic diagram of a UV monitoring circuit 770 according to yet another embodiment of the invention. The UV monitoring circuit 770 includes a phototransistor 772. Although the phototransistor 772 may itself serve as a UV detector, in some implementations, an optical filter (not shown) would limit the radiation that impinges on the phototransistor 772 in which case the phototransistor 772 together with the optical filter serves as the UV detector. A collector terminal of the phototransistor 772 is coupled to a power source Vcc. An emitter terminal of the phototransistor 772 is coupled to a first end of a resistor 774, a first end of a capacitor 776 and a gate terminal of a transistor 778. An output device 780 couples between the power source Vcc and a drain terminal of the transistor 778. A second end of the resistor 774, a second end of a capacitor 776 and a source terminal of the transistor 778 are coupled to a drain terminal of a transistor 784. As an example, the transistors 778 and 784 can be n-channel metal-oxide-semiconductor, enhancement-mode, field-effect transistors (MOSFETs). As one example, MOSFETs can be 2N7008 MOSFETs. The source terminal of the transistor 784 is coupled to ground. The gate terminal of the transistor 784 is coupled to a first end of a resistor 786 and a first end of a capacitor 788. A second end of the resistor 786 and the second end of the capacitor 788 are coupled to ground. The gate terminal of the transistor 784 is also coupled to the power source Vcc through a being-worn switch 782. A battery 790 can supply power to the UV monitoring circuit 770. As one example, the battery 790 can be a three (3) Volt lithium battery. The size and configuration of the battery 790 can also vary. In one example, the battery 790 can be a coin battery. In another example, the battery 790 can be a triple-A (AAA) battery. As sufficient radiation, such as UV radiation, impinges on the phototransistor 772, the phototransistor 772 conducts so that the emitter terminal of the phototransistor 772 outputs the voltage V1 by coupling to the power source Vcc through the phototransistor 772. The capacitor 776 then charges up in accordance with a time constant determined by the capacitance of the capacitor 776 and the resistance of the resistor 774. When the voltage V1 exceeds a turn-on voltage for the transistor 778, the transistor 778 conducts. However, in this embodiment, the transistor 784 also must conduct in order for the output device 770 to be activated. The transistor 784 conducts when the "being worn" switch 782 is closed. The "being worn" switch 782 indicates whether the eyewear (including the UV monitoring circuit 770) is being worn by its user. The sensitivity of the "being worn" switch 782 can be controlled by the capacitance of the capacitor 788 and the resistance of the resistor 786. For example, the output device 780 can indicate that the UV monitoring circuit 770 has detected exposure to a large amount of UV radiation while the eyewear is being worn. The amount of UV radiation exposure being detected can vary depending on the capacitance of the capacitor 776 and the resistance of the resistor 774.

The UV monitoring circuits according to the invention can also include switches, such as a "being-worn" switch, skin type, reset switch and/or an on/off switch. A "being-worn" switch was, for example, discussed above with reference to FIG. 7C. The on/off switch can also provide a reset capability. A reset switch and an/on switch are further discussed below with reference to FIG. 7D.

Figure 7D:
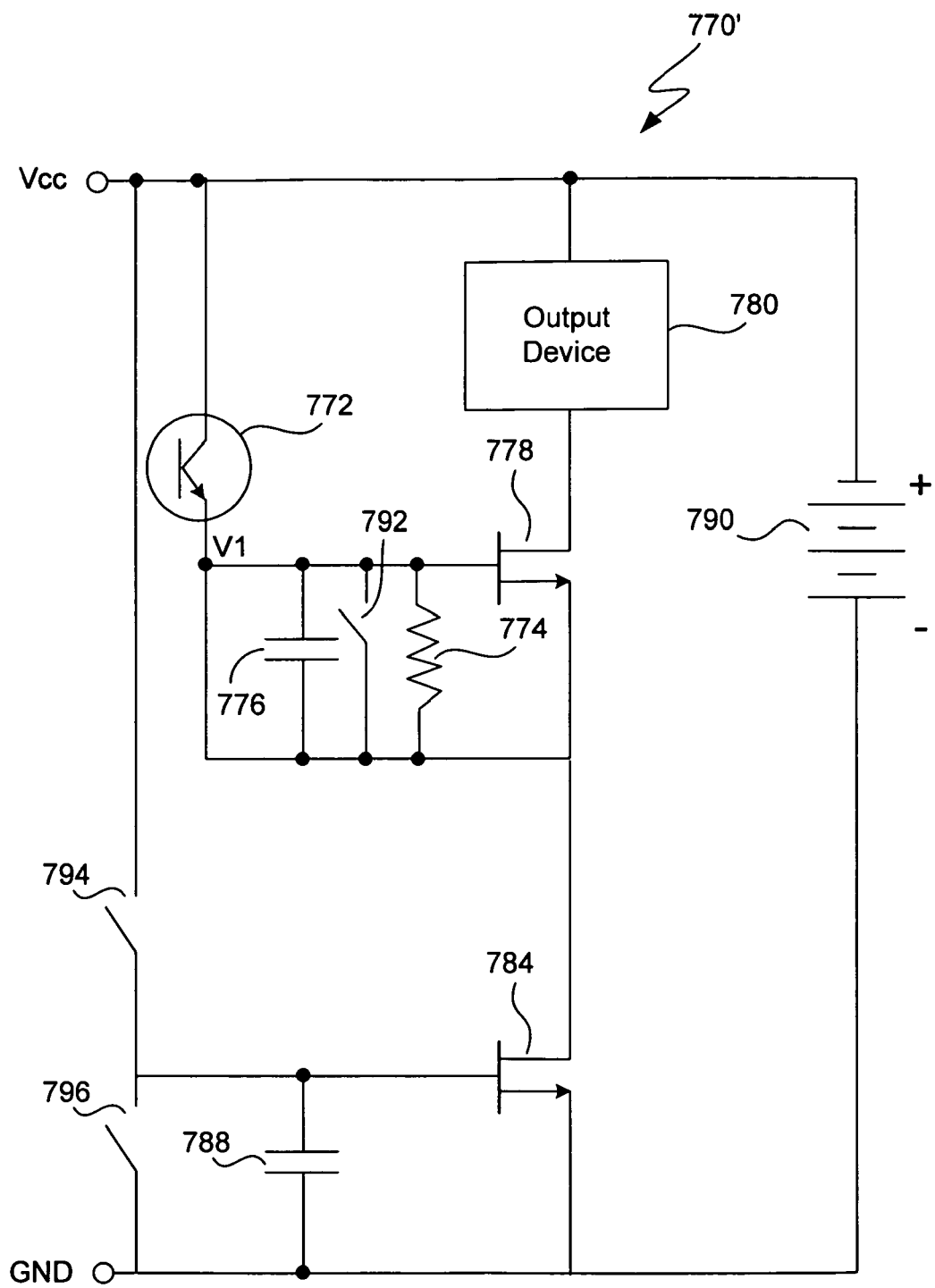
FIG. 7D is a schematic diagram of a UV monitoring circuit according to still yet another embodiment of the invention.

FIG. 7D is a schematic diagram of a UV monitoring circuit 770' according to still yet another embodiment of the invention. The UV monitoring circuit 770' is generally similar to the UV monitoring circuit 770 of FIG. 7C, except that a reset switch 792, an on switch 794 and an off switch 796 are provided. Additionally, the resistor 786 shown in FIG. 7C is removed from the UV monitoring circuit 770'. The reset switch 792 can be a push button, such that when pressed, causes any charge on the capacitor 776 to be discharged. As a result, assuming the transistor 778 is conducting (i.e., on) when the reset switch is pushed, the transistor 778 stops conducting (i.e., off) because the voltage V1 is effectively zeroed and thus does not exceed the turn-on voltage for the transistor 778. Consequently, the output device 780 stops providing any output (e.g., display device cleared or off, audio stopped, etc.). Once the reset switch 792 is released, the capacitor 776 can again begin to accumulate charge representing UV radiation. The on switch 794 and the off switch 796 can also be implemented as push button switches. When the on switch 794 is pressed, the capacitor 788 is charged so that the transistor 784 conducts (i.e., turns-on) and then remains on until the off switch 796 is pressed. In this embodiment, the on switch 794 and the off switch 796 should not both be pressed at the same time. Although the reset switch 792, the on switch 794 and the off switch 796 are implemented as push button switches in FIG. 7D, other types of switches can be used.

Figure 8:
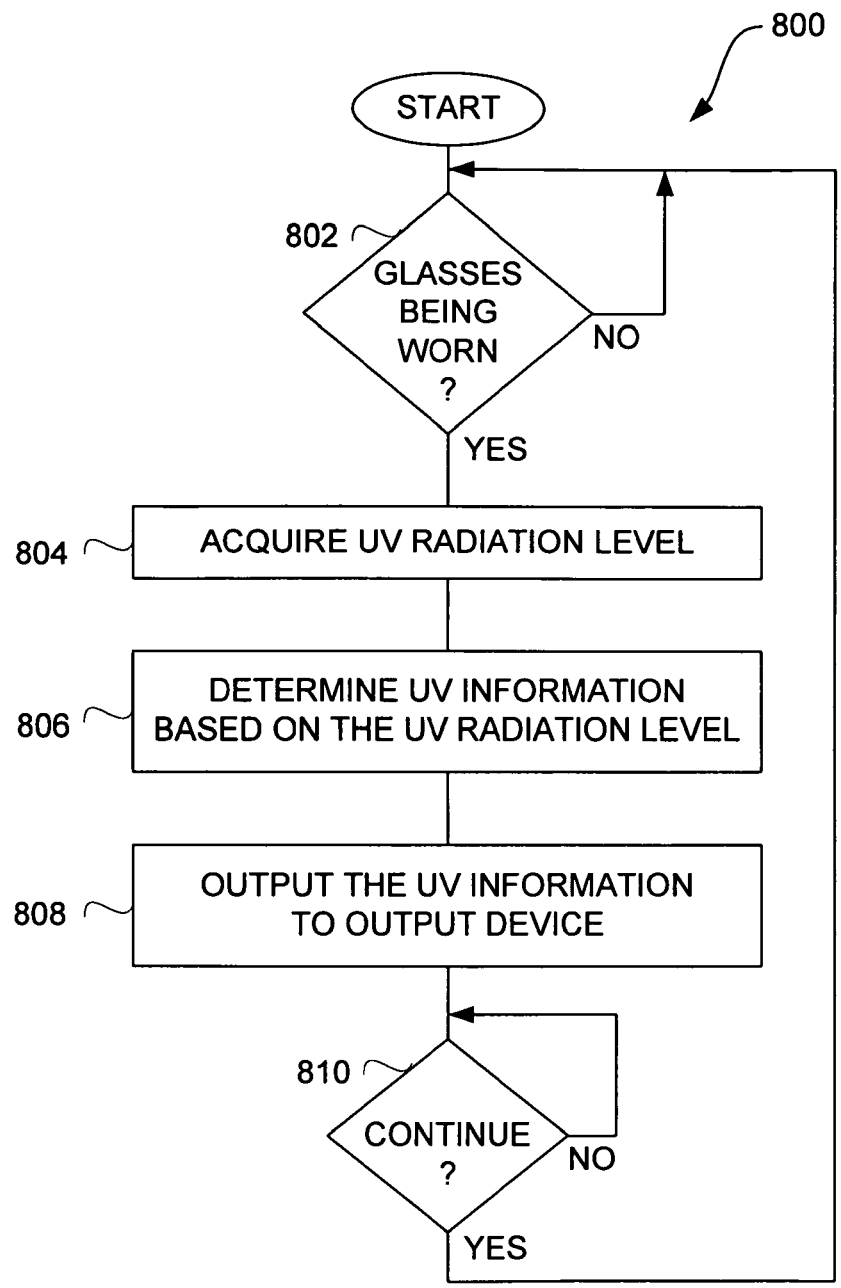
FIG. 8 is a flow diagram of a UV monitoring process according to one embodiment of the invention.

FIG. 8 is a flow diagram of a UV monitoring process 800 according to one embodiment of the invention. The UV monitoring process 800 is, for example, performed by a UV monitoring system embedded within and/or tethered to a pair of glasses. The UV monitoring system can, for example, represent any of the UV monitoring systems 300, 400, 450, 460, 470, 600, 700, 750, 770 or 770' discussed above with reference to FIGS. 3, 4A-4D, 6 and 7A-7D.

The UV monitoring process 800 begins with a decision 802 that determines whether the glasses are being worn. As noted above, the determination of whether the glasses are being worn can be done in a variety of ways. In any case, when the decision 802 determines that the glasses are not being worn, then the UV monitoring process 800 waits until the glasses are being worn. In other words, when the glasses are not being worn, the UV monitoring process 800 can stop, block (pause or wait) or deactivate until it is determined that the glasses are being worn.

On the other hand, when the decision 802 determines that the glasses are being worn, a UV radiation level is acquired 804. For example, the UV radiation level can be acquired 804 from electronic circuitry which can include a UV detector. Next, UV information is determined 806 based on the UV radiation level (radiation data). For example, the UV information can pertain to normalized or calibrated radiation data, accumulated radiation data, or processed radiation data. Hence, although the UV radiation level (radiation data) could be output to the user, by outputting the UV information to the user of the glasses, more useful information (e.g., easier to comprehend) can be presented to the user. Other examples of UV information are referenced elsewhere, such as the UV radiation information discussed below in FIG. 9.

Next, the UV information can be output 808 to the output device. The UV information need not always be output 808 to the output device. For example, the UV information could be output 808 to the output device depending upon whether it signals a particular condition to the user. As another example, the UV information could be output to the output device on request by the user. As still another example, the UV information could be output to the output device based on a sensed condition or event. Next, a decision 810 can determine whether the UV monitoring process 800 should continue. When the decision 810 determines that the UV monitoring process 800 should not continue, then the UV monitoring process 800 waits until it is time to be continued. This allows the UV monitoring process 800 to be performed periodically or as needed, which can lead to reduced power consumption and/or more meaningful output information to the user. While the UV monitoring process 800 is waiting, some or all of the UV monitoring system can be in a reduced power consumption state. Nevertheless, when the decision 810 determines that the UV monitoring process 800 should continue, the UV monitoring process 800 returns to repeat the decision 802 and subsequent operations.

Figure 9:
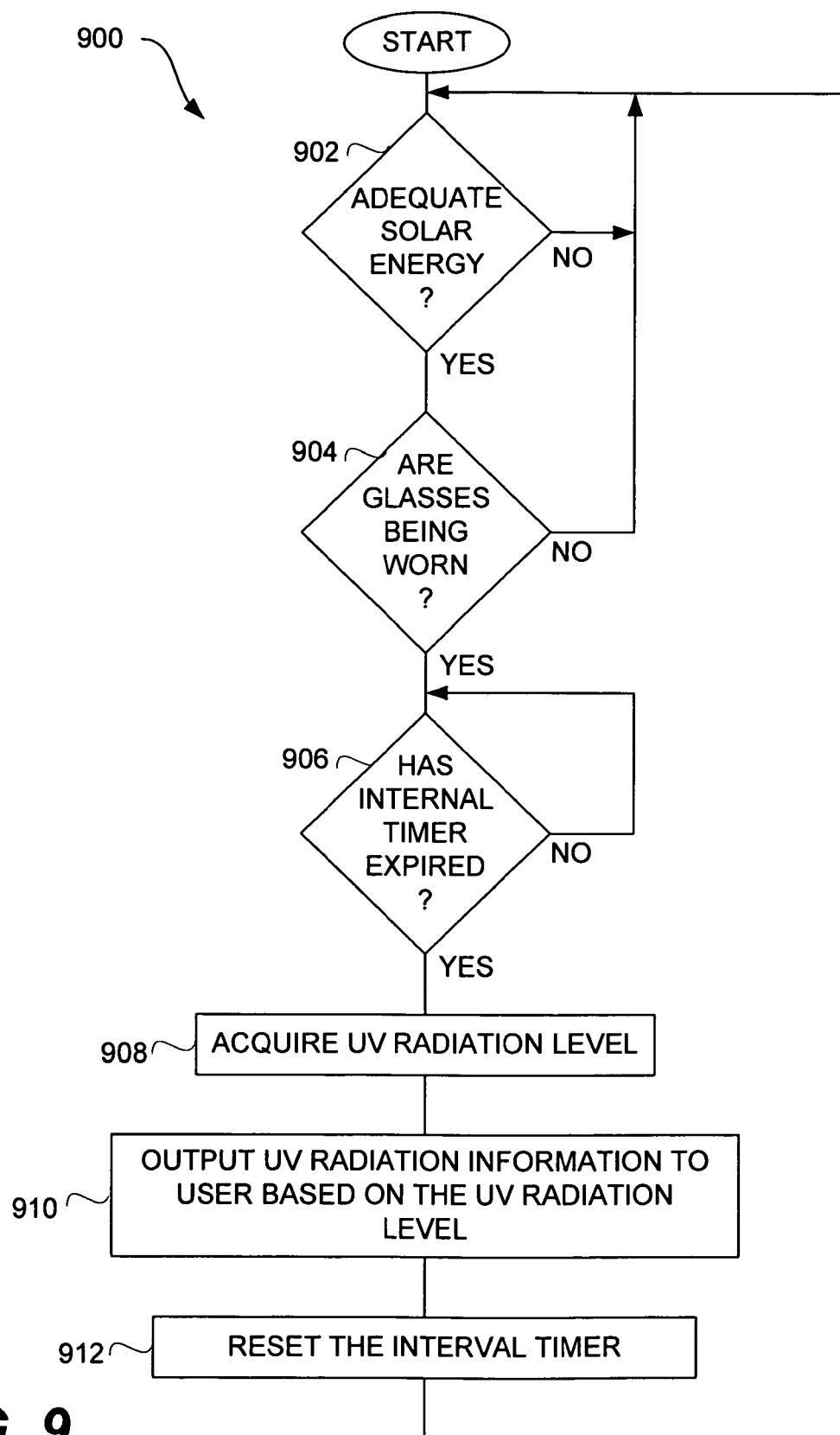
FIG. 9 is a flow diagram of a UV monitoring process according to another embodiment of the invention.

FIG. 9 is a flow diagram of a UV monitoring process 900 according to another embodiment of the invention. The UV monitoring process 900 is, for example, performed by a UV monitoring system embedded within and/or tethered to a pair of glasses. The UV monitoring system can, for example, represent any of the UV monitoring systems 300, 400, 450, 460, 470, 600, 700, 750, 770 or 770' discussed above with reference to FIGS. 3, 4A-4D, 6 and 7A-7D. However, the UV monitoring process 900 is particularly suitable for UV monitoring systems having "being worn" detection capability, such as the UV monitoring systems 450 and 770.

The UV monitoring process 900 begins with a decision 902 that determines whether adequate solar energy is present. In this embodiment, solar cells provide adequate solar energy for the UV monitoring process 900 to be performed. In other words, the UV monitoring system (and thus the glasses) operate in the presence of light. When the decision 902 determines that adequate solar energy (e.g., sunlight or artificial light) is not present, then the UV monitoring process 900 awaits adequate solar energy. In one implementation, the UV monitoring system performing the UV monitoring process 900 can automatically turn-off or deactivate when inadequate solar energy is present. Such operation facilitates passive UV monitoring with minimal user participation.

On the other hand, when the decision 902 determines that adequate solar energy is present, a decision 904 determines whether the glasses are being worn. When the decision 904 determines that the glasses are not being worn, then the UV monitoring process 900 returns to repeat the decision 902 and subsequent operations. In effect, the UV monitoring process 900 is not performed when the decision 904 determines that the glasses are not being worn by the user. As noted above, the determination of whether the glasses are being worn can be done in a variety of ways.

Optionally, a delay can be inserted when the decision 904 determines that the glasses are not being worn so as to save power consumption. Such a delay would allow the UV monitoring process 900 to stop, halt, inactivate or otherwise wait for the period of the delay prior to returning to the decision 902 and subsequent operations. While the UV monitoring process 900 is stopped, halted, inactivated or otherwise waiting, some or all of the UV monitoring system can be in a reduced power consumption state.

Alternatively, when the decision 904 determines that the glasses are being worn, a decision 906 can determine whether an interval timer has expired. The interval timer can determine how frequently the UV radiation level is checked and/or how frequently radiation information is output to a display. The interval timer can also thus lead to reduced power consumption (i.e., low-power mode for the electronic circuitry). When the decision 906 determines that the interval timer has not expired, the UV monitoring process 900 waits for the interval timer to expire. During this period of waiting, the UV monitoring process 900 can place some or all of the UV monitoring system in a low-power mode. Alternatively, during this period of waiting, the UV monitoring process 900 can perform processing of other auxiliary sensors that can produce other sensor data which can be processed in conjunction with UV radiation levels.

Once the decision 906 determines that the interval timer has expired, a UV radiation level is acquired 908. Then, UV radiation information is output 910 to the user of the glasses based on the UV radiation level. For example, the UV radiation information can pertain to an instantaneous radiation level, an accumulated radiation level, or some reference radiation indication. An example of a reference radiation indication can be a numerical value, text or a graphic indication. One example of a numerical value implementation is a value representing a percentage of recommended daily dosage. Another example of a numerical value implementation is a value representing UV intensity. One example of a text implementation would be a word (e.g., "ok", "Burnt", etc.). One example of a graphic implementation would be a bar-type graph. Another example of a graphic implementation would be a graphic symbol (e.g., a lobster symbol, a fire flames symbol, a picture of a sun, or a smiley face).

Next, the interval timer can be reset 912 and the UV monitoring process 900 can thereafter return to repeat the decision 902 and subsequent operations. As a result, the UV monitoring provided by the UV monitoring process 900 can be continuously performed so long as adequate solar energy is present and the glasses are being worn.

Figure 10:
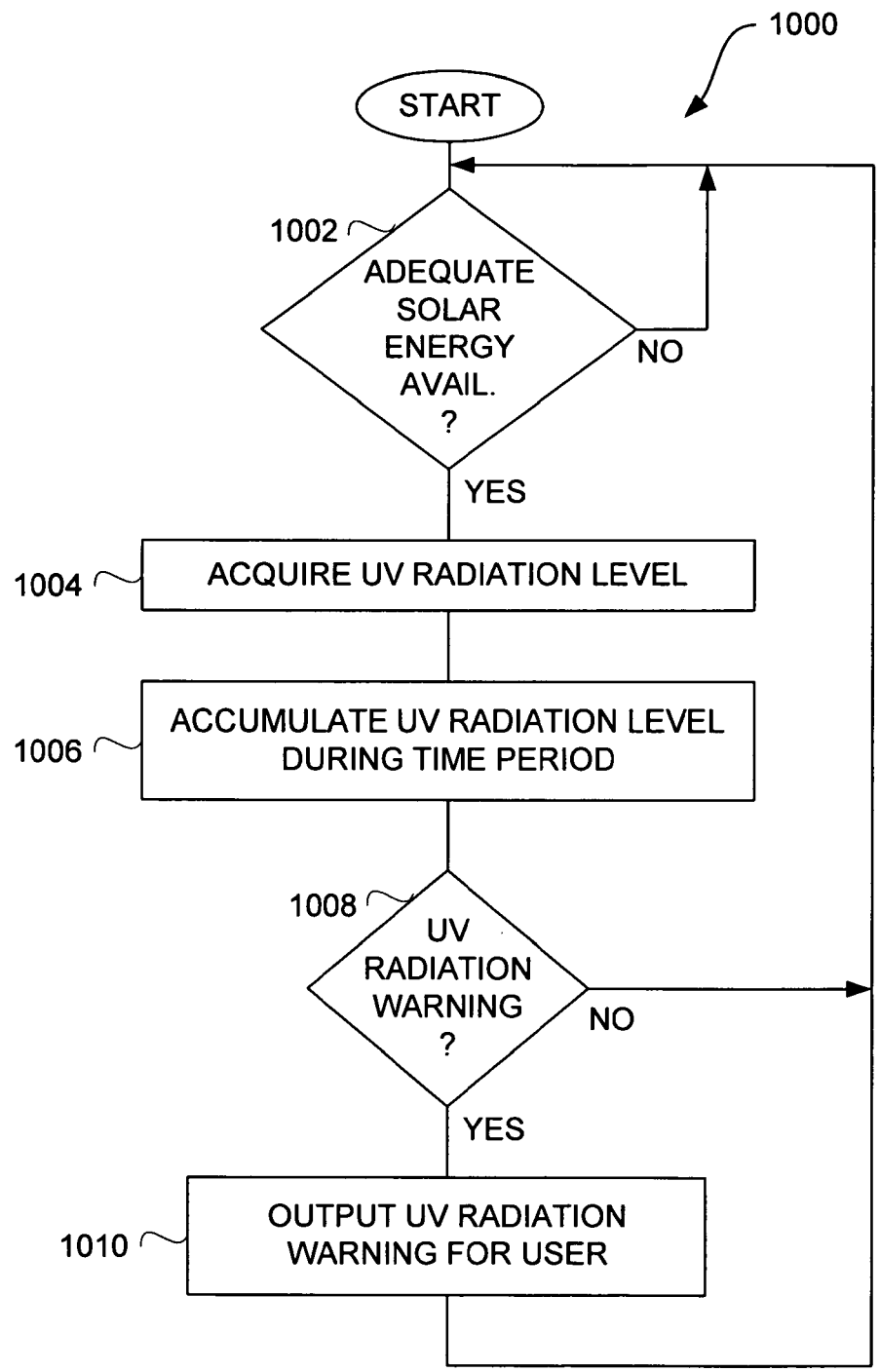
FIG. 10 is a flow diagram of a UV monitoring process according to yet another embodiment of the invention.

FIG. 10 is a flow diagram of a UV monitoring process 1000 according to yet another embodiment of the invention. The UV monitoring process 1000 is, for example, performed by a UV monitoring system embedded within and/or tethered to a pair of glasses. The UV monitoring system can, for example, represent any of the UV monitoring systems 300, 400, 450, 460, 470, 600, 700, 750, 770 or 770' discussed above with reference to FIGS. 3, 4A-4D, 6 and 7A-7D.

The UV monitoring process 1000 begins with a decision 1002 that determines whether adequate solar energy (e.g., sunlight or artificial light) is available. When the decision 1002 determines that adequate solar energy is not available, then the UV monitoring process 1000 is deactivated, blocked or effectively not invoked. In this embodiment, solar cells provide adequate solar energy for the UV monitoring process 1000 to be performed. In other words, the glasses operate in the presence of sufficient light. When the decision 1002 determines that adequate solar energy is not present, then the UV monitoring process 1000 awaits adequate solar energy.

Once the decision 1002 determines that adequate solar energy is available, then the UV monitoring process 1000 proceeds. Here, the UV monitoring process 1000 can optionally determine whether the glasses are being worn. In any case, as shown in FIG. 10, when the decision 1002 determines that adequate solar energy is available, a UV radiation level is acquired 1004. For example, the UV radiation level can be acquired by a UV detector.

Next, the UV radiation level is accumulated 1006 during a time period. Here, the UV radiation levels acquired over a predetermined period of time are accumulated 1006 so that the radiation information is based on an accumulation of radiation that has been acquired over the predetermined period of time. For example, the predetermined period of time can be one hour, four hours, eight hours, twelve hours, twenty-four hours, two days, four days, one week, one month or one year.

Thereafter, a decision 1008 determines whether a UV radiation warning is needed. Here, the accumulated UV radiation level can be compared with a threshold to determine whether the accumulated UV radiation is excessive. In one implementation, the threshold can vary with, or be personalized to, different users, such as based on skin type, age, or skin condition. A user of the glasses can input data (e.g., skin type) by way of at least one switch or button. In another implementation, a plurality of threshold levels can be used, e.g., to provide a progression of UV radiation levels (and notifications). Alternatively, the glasses can use predetermined settings and offer several versions (e.g., different glasses for different skin types).

When the decision 1008 determines that the UV radiation warning is not needed, then the UV monitoring process 1000 returns to repeat the decision 1002 and subsequent operations so that the UV radiation level can continuously or periodically be monitored. In one embodiment, the UV monitoring process 1000 can reset the accumulated UV radiation after the period of time has been exceeded. In another embodiment, the accumulated UV radiation can be reset after no significant UV radiation is present for a period of time (e.g., 6-12 hours), after no significant solar energy is present for a period of time (e.g., 6-12 hours), or after not being worn for a period of time (e.g., 6-12 hours), whereby each evening, for example, the reset can automatically occur. In another embodiment, the UV monitoring system, and thus the UV monitoring process 1000, can be automatically turned off (which also resets) after the period of time has been exceeded or after no significant UV radiation is present for a period of time.

On the other hand, when the decision 1008 determines that a UV radiation warning is needed, then a UV radiation warning is output 1010 to the user. The warning can be varied or personalized to the user, and/or can vary depending on the user, user preference, UV radiation level, or auxiliary sensor data. In one implementation, the warning can pertain to a recommendation (e.g., SPF recommendation, get out of sun, high exposure warning, etc.). The radiation warning can be output 1010 via the output device. For example, as noted above, the output device can be a display, a speaker or a vibration device. Hence, the warning can be output to the user by displaying text or graphics, audio sounds, or physical actions. Following the output 1010 of the UV radiation warning, the UV monitoring process 1000 can return to repeat the decision 1002 and subsequent operations so that UV monitoring can continue.

Although the circuitry in FIGS. 7A-7D and the processing in FIGS. 8-10 have been described in the context of monitoring UV radiation, it should be understood that such circuitry and processing are also applicable to monitoring other types of radiation.

Figure 11:
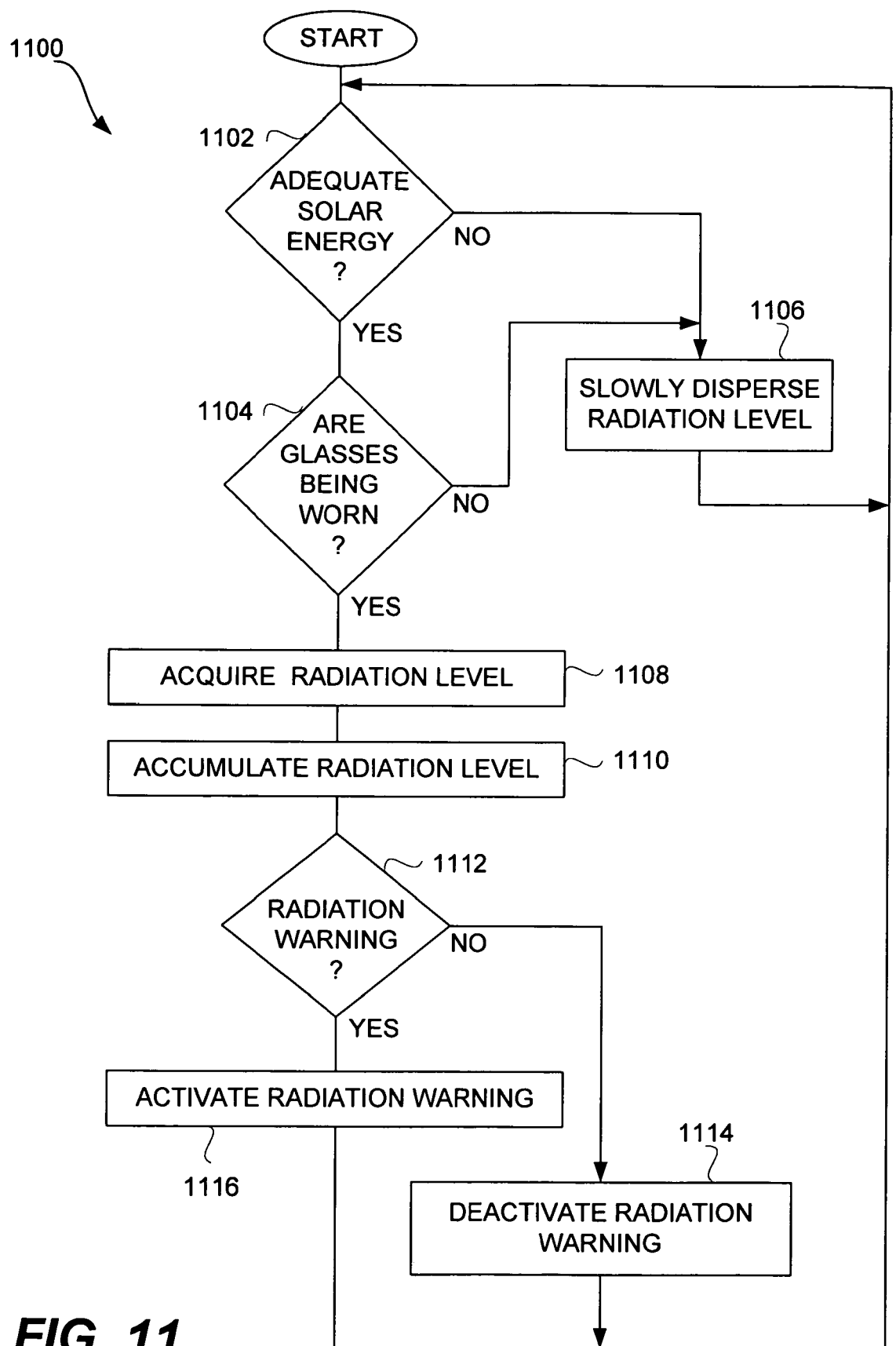
FIG. 11 is a flow diagram of a UV monitoring process according to still yet another embodiment of the invention.

FIG. 11 is a flow diagram of a monitoring process 1100 according to still yet another embodiment of the invention. The monitoring process 1100 is, for example, performed by a monitoring system embedded within and/or tethered to a pair of glasses. The monitoring system can, for example, represent any of the UV monitoring systems 300, 400, 450, 460, 470, 600, 700, 750, 770 or 770' discussed above with reference to FIGS. 3, 4A-4D, 6 and 7A-7D.

The monitoring process 1100 begins with a decision 1002 that determines whether adequate solar energy (e.g., light) is available. In one implementation, the monitoring system performing the monitoring process 1100 includes at least one solar cell or at least one phototransistor, and the solar cell or phototransistor can be used to determine whether there is adequate solar energy available. Hence, when the decision 1102 determines that adequate solar energy is not available, then the monitoring process 1100 is deactivated, blocked or effectively not invoked. In this embodiment, solar cells can provide adequate solar energy for the monitoring process 1000 to be performed. In another embodiment, a phototransistor can detect whether adequate solar energy is available. In other words, the glasses operate in the presence of sufficient light. When the decision 1102 determines that adequate solar energy is not present, then the monitoring process 1100 awaits adequate solar energy. In this condition, the monitoring system can be in a low power condition (e.g., essentially disabled).

Once the decision 1102 determines that adequate solar energy is available, then the monitoring process 1100 proceeds. Here, the monitoring process 1100 can optionally determine whether the glasses are being worn. In any case, as shown in FIG. 11, when the decision 1102 determines that adequate solar energy is available, a decision 1104 determines whether the glasses are being worn by a user. When the decision 1104 determines that the glasses are not being worn or when the decision 1102 determines that adequate solar energy is not present, then a radiation level previously acquired through accumulation (described below) can be slowly dispersed 1106. In one embodiment, the rate of dispersal is substantially slower that the rate of accumulation of the UV radiation level. For example, in a case where the radiation being monitored is UV radiation, the UV radiation level might accumulate to cause a UV radiation warning after 1-2 hours of extensive UV or sunlight exposure, but might take 6-12 hours to disperse the previously accumulated radiation level after the UV radiation is removed. Hence, the accumulation of radiation can gracefully tolerate interruption of radiation, such as when going indoors (e.g., within a building) for a period of time (e.g., 15 minutes, 1 hour, 4 hours, etc.) when UV radiation is being monitored. Following the block 1106, the monitoring process 1100 returns to repeat the decision 1102 and subsequent blocks.

On the other hand, when the decision 1104 determines that the glasses are being worn, a radiation level is acquired 1108. For example, the radiation level can be acquired by a detector (e.g., UV detector). Next, the radiation level is accumulated 1110. Here, the radiation levels acquired can be accumulated so that radiation information can be based on an accumulation of radiation that has been acquired while the glasses are being worn.

Thereafter, a decision 1112 determines whether a radiation warning is needed. Here, the accumulated radiation level can be compared with a threshold to determine whether the accumulated radiation is excessive. In one implementation, the threshold can vary with, or be personalized to, different users, such as based on skin type, age or skin condition. In another implementation, a plurality of threshold levels can be used, e.g., to provide a progression of radiation levels (and notifications). A user of the glasses can input data (e.g., skin type, preferences) by way of at least one switch or button. Alternatively, the glasses can use predetermined settings and offer several versions (e.g., different glasses for different skin types).

When the decision 1112 determines that the radiation warning is not needed, then the monitoring process 1100 deactivates 1114 the radiation warning. Alternatively, when the decision 1112 determines that the radiation warning is needed, then the monitoring process 1100 activates 1116 the radiation warning. The warning can be varied or personalized to the user, and/or can vary depending on the user, user preference, radiation level, or auxiliary sensor data. The radiation warning can be produced at an output device. For example, as noted above, the output device can be a display, a speaker or a vibration device. In one implementation, the warning is a graphical symbol or text that signals the user of the glasses that they have received a significant amount of radiation. Following the deactivation 1114 and the activation 1116, the monitoring process 1100 can return to repeat the decision 1102 and subsequent operations so that monitoring can continue.

The radiation warning can remain active anywhere from a brief period to continuously depending on the type of warning being provided, user preference or manufacturer setting. For example, an audio alert might sound for a few seconds, while a displayed alert might remain on for a longer duration. The radiation warning can be output differently depending on the power situation of the monitoring system. If the monitoring system is being solar powered, then the radiation warning can remain active until deactivated. However, when the monitoring system is being battery powered, the radiation warning might be active for only a brief period.

Figure 12:
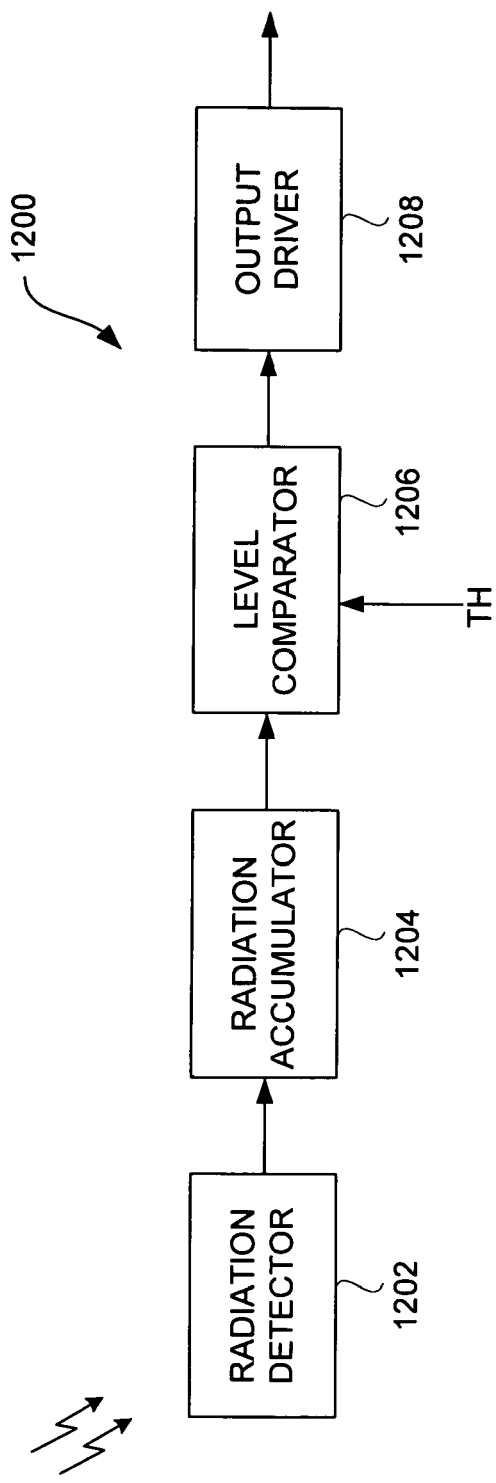
FIG. 12 is a block diagram of electronic circuitry according to one embodiment of the invention.

FIG. 12 is a block diagram of electronic circuitry 1200 according to one embodiment of the invention. The electronic circuitry 1200 can, for example, be used for at least a part of the electronic circuitry 302 shown in FIGS. 3, 4A, 4B, 4D and 6. The electronic circuitry 1200 includes a radiation detector 1202 that outputs a radiation level signal dependent on an amount of radiation impinging on the radiation detector 1202. For example, in the case where radiation from sunlight is being monitored, the radiation detector 1202 can principally detect ultraviolet or infrared radiation. In another example, in the case where radiation from x-ray machines or nuclear materials is being monitored, the radiation detector can principally detect gamma radiation. A radiation accumulator 1204 receives the radiation signal level and accumulates the radiation signal level to produce an accumulated radiation level. A level comparator 1206 can then compare the accumulated radiation level to a threshold level (TH). The threshold level can be fixed, selected or determined. When the accumulated radiation level exceeds the threshold level, then an output driver 1208 operates to output one or more signals to cause an output device to produce an output. The output can be visual, audio, and/or physical. The threshold can be varied or personalized to the user, and/or can vary depending on the user. The threshold can also depend on or vary in view of one or more of user preferences, position (e.g., closer equator), intensity level of radiation, user characteristics (e.g., skin color or type), or auxiliary sensor data, etc. The level comparator 1206 can also use one or more threshold levels.

In one embodiment, the threshold used by the level comparator 1206 can correspond to a recommended daily dosage of such radiation. For example, if the radiation detector 1202 is primarily detecting UV radiation, the recommended daily dosage would pertain to UV radiation.

Figure 13A:
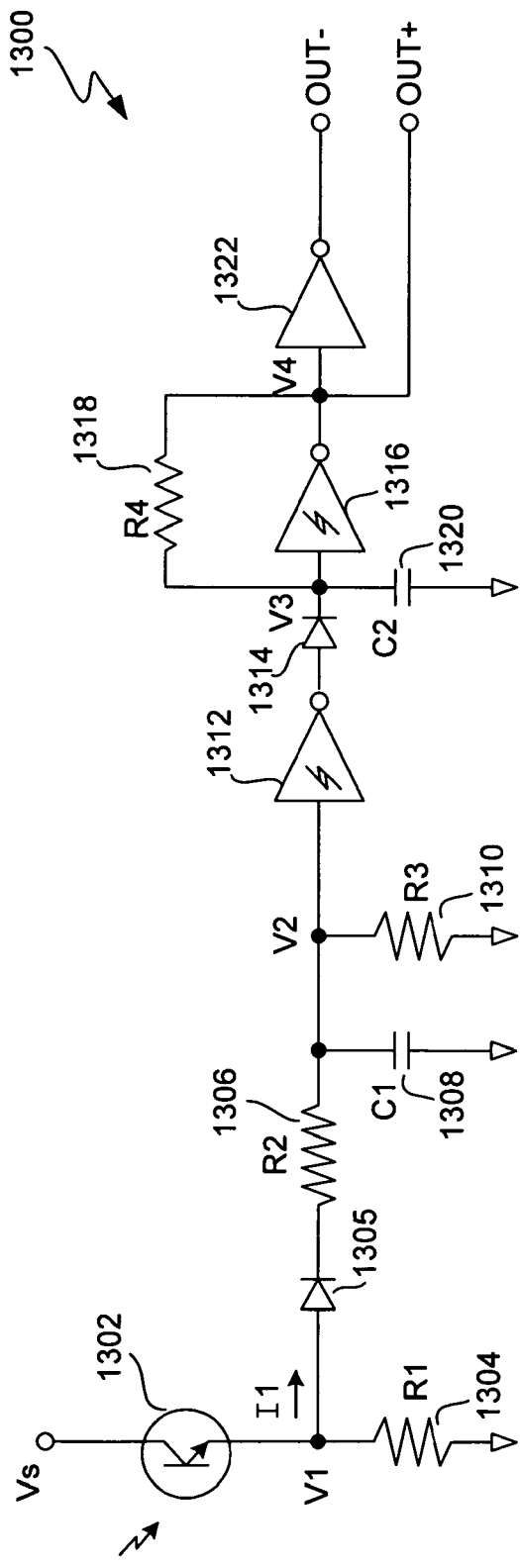
FIG. 13A is a schematic diagram of an electronic circuit for a UV detection system according to one embodiment of the invention.

FIG. 13A is a schematic diagram of an electronic circuit 1300 for a radiation detection system according to one embodiment of the invention. The electronic circuit 1300 is, for example, suitable for use as the electronic circuitry 1200 shown in FIG. 12.

The electronic circuit 1300 includes a phototransistor 1302 and a resistor (R1) 1304 coupled in series between a supply voltage (Vs) and ground. In this embodiment, the phototransistor 1302 implements a radiation detector. As radiation (of an appropriate frequency range) strikes the phototransistor 1302, a voltage V1 appears at a first node connecting the phototransistor 1302 to the resistor (R1) 1304. The voltage V1 induces a current I1 that passes through a diode 1305 and a resistor (R2) 1306. A voltage V2 at a second node then begins to rise from ground level to the level of V1 by the charging of a capacitor (C1) 1308 at a rate dependent on the amount of the current I1 and the capacitance of the capacitor (C1) 1308 and the resistances of the resistors (R2 and R3) 1306 and 1310, respectively. A Schmitt trigger inverter 1312 couples to the second node and receives the voltage V2 at its input. When the voltage V2 exceeds the turn-on voltage for the inverter 1312, the output of the inverter 1312 goes low and couples to a third node via a diode 1314. At this point, the low voltage (V3) at the third node couples to an input of a Schmitt trigger inverter 1316, which outputs a high voltage (V4) at a fourth node which charges a resistor (R4) 1318 and capacitor (C2) 1320. The resistor (R4) 1318 couples between the third and fourth nodes. The capacitor (C2) couples between the third node and ground. Once the voltage V3 has risen sufficiently, the inverter 1316 switches to output a low voltage (V4), thereby discharging the capacitor (C2) 1320. Hence, the inverter 1316, the resister (R4) 1318 and the capacitor (C2) 1320 form an oscillator. The outputs for the electronic circuit 1300 are complementary, a positive output from the fourth node and a negative output from an inverter 1322 coupled to the fourth node. These complementary outputs are applicable for driving a LCD type display device.

Although not shown in FIG. 13A, the electronic circuit 1300 can optionally further include a reset switch. For example, if provided, the reset switch can be coupled between the second node and ground. While the reset switch is normally open, when closed the reset switch discharges the capacitor (C1) 1308. As an example, the reset switch can be implemented by a push button switch. Although the electronic circuit 1300 can automatically reset after no significant UV radiation is present for a period of time (such as noted above), the reset switch permits a user to manually reset the electronic circuit 1300 so as to clear and restart monitoring (e.g., accumulation) of radiation.

The electronic circuit 1300 can facilitate low power operation. In one implementation, the resistor (R1) 1304 can be made large. In another implementation, power dissipated by resistor (R1) can be conserved by using a radiation detector, such as a phototransistor, that is responsive to the radiation of interest but with very low sensitivity to the radiation of interest. In the case of a phototransistor, sensitivity can be reduced by covering the phototransistor with a layer of aluminized Mylar. Aluminized Mylar can attenuate light passing through it by a factor of approximately one-thousand (1000). In still another implementation, the supply voltage (Vs) supplied to the phototransistor 1302 can be periodic, so that power consumed by the resister (R1), which, in this case, need not be a high resistance, is substantially reduced, yet the phototransistor 1302 has an extended dynamic range. The sensitivity of the radiation measurement can also be adjusted by changing the duty-cycle of the periodic supply voltage (Vs). These various implementations for low power operation can be used singly or in combination.

Figure 13B:
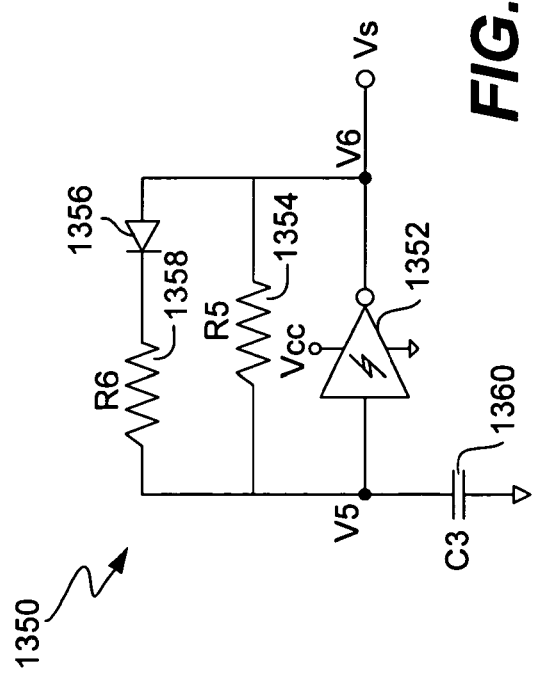
FIG. 13B is a schematic diagram of a periodic supply voltage circuit according to one embodiment of the invention.

FIG. 13B is a schematic diagram of a periodic supply voltage circuit 1350 according to one embodiment of the invention. The periodic supply voltage circuit 1350 is, for example, suitable for use to provide a supply voltage (Vs) to the electronic circuit 1300 for a radiation detection system. In this embodiment the supply voltage (Vs) is periodic. In this example, the supply voltage (Vs) uses pulse-width modulation. The periodic supply voltage circuit 1350 includes a Schmitt trigger inverter 1352 that is powered by a power supply (Vcc) when the radiation detection system is operating (i.e., turned-on). At this point, the voltage (V5) at an input node is assumed low and couples to an input of the Schmitt trigger inverter 1352, which outputs a high voltage (V6) at an output node which charges a capacitor (C3) 1360 via resistor (R5) 1354 and resistor (R6) 1358. A diode 1356 conducts during charging, but blocks during discharging. The resistor (R5) 1354 couples between the input and output nodes. The diode 1356 and the resistor (R6) 1358 are coupled in series between the input and output nodes. The capacitor (C3) 1360 couples between the input node and ground. Once the voltage (V5) at the input node has risen sufficiently, the inverter 1352 switches to output a low voltage (V6) at the output node, thereby discharging the capacitor (C3) 1360 via the resistor (R5) 1354. Hence, the periodic supply voltage circuit 1350 forms an oscillator. The output for the periodic supply voltage circuit 1350 at the output node (V6) can be the supply voltage (Vs) for the radiation detection system. Given the diode 1356, the supply voltage (Vs) is in the high state for a short time and in the low state for a longer period of time.

Although the resistance and capacitance values for the electronic circuit 1300 and the periodic supply voltage circuit 1350 can vary widely with implementation and application, some exemplary values are as follows. For example, for the electronic circuit 1300, the resistor (R1) 1304 can be 22 k ohms, the resistor (R4) 1318 can be 330 k ohms, and the capacitor (C2) 1320 can be 0.1 microfarads (µf). The resistor (R2) 1306 and the resistor (R3) 1310 can, for example, be in the range of 1-50 M ohms. The capacitor (C1) 1308 can, for example, be in the range of 1-100 µf. For example, for the periodic supply voltage circuit 1350, the resistor (R5) 1354 can be 10 M ohms, the resistor (R6) 1358 can be 200 k ohms, and the capacitor (C3) 1360 can be 0.01 µf.

Figure 14A:
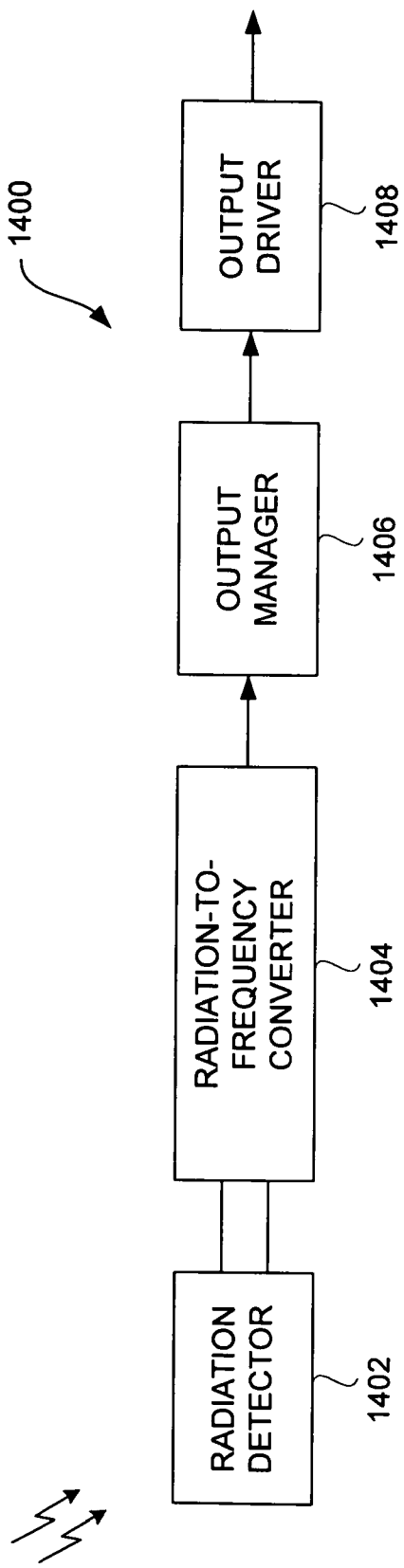
FIG. 14A is a block diagram of a radiation monitoring system according to one embodiment of the invention.

FIG. 14A is a block diagram of a radiation monitoring system 1400 according to one embodiment of the invention. The radiation monitoring system 1400 can, for example, be used for the electronic circuitry 302 shown in FIGS. 3, 4A, 4B, 4D and 6. The radiation monitoring system 1400 includes a radiation detector 1402 that detects impinging radiation, such as ultraviolet radiation, infrared radiation or light, and outputs a radiation indication to a radiation-tofrequency converter 1404. The radiation indication can represent an amount of radiation impinging on the radiation detector 1402. The radiation-to-frequency converter 1404 converts the radiation indication into a frequency signal. The frequency signal is supplied to an output manager 1406. The output manager 1406 coordinates when an output is to be provided for the radiation monitoring system 1400. In one embodiment, the output manager 1406 determines that an output indication should be provided based on a count or a division with respect to the frequency signal. For example, the greater the amount of radiation being detected by the radiation detector 1402, the greater the frequency of the frequency signal. Hence, when greater levels of radiation are detected, the output manager 1406 can more quickly provide an output indication (e.g., signaling substantial radiation exposure) as compared to a situation in which the amount of radiation being detected by the radiation detector 1402 is substantially less.

In any case, when the output manager 1406 determines that an output indication is to be provided, the output manager 1406 provides an output signal to an output driver 1408. The output driver 1408 controls an output device so as to produce an output indication. The output indication can be textual (including numerical) and/or graphical. For example, as a numerical output, the output could indicate a percentage of acceptable radiation for a day that has been already detected. As another example, the output could be a graphical output that pertains a symbol or a graph. In one embodiment, the output provided by the output device is a visual output on a display device. However, in general, the output can be visual and/or audio. For example, examples of audio outputs are beeping sounds, synthesized speech, or prerecorded audio messages.

The output manager 1406 receives the frequency signal from the radiation-to-frequency converter 1404 and can determines when an output indication should be provided. In one implementation, the output manager 1406 can include a divider that divides down the frequency signal from the radiation-to-frequency converter 1404 such that the output manager 1406 causes the output driver 1408 to produce an output indication based on an amount of radiation that has effectively been detected. As an example, a predetermined amount of radiation to be effectively detected can be controlled by altering the amount of division provided by the divider. Hence, the amount of division utilized by the output manager 1406 can correspond to a radiation threshold amount, such as a recommended daily dosage of ultraviolet radiation. The amount of division provided by the divider can also depend on or vary in view of one or more of user preferences, position (e.g., proximity to equator), intensity level of radiation, user characteristics (e.g., skin color or type), or auxiliary sensor data, etc. Alternatively, the output manager 1406 can include a counter that counts based on the frequency signal from the radiation-to-frequency converter 1404, wherein the amount of count utilized by the output manager 1406 can also correspond to a radiation threshold amount.

In an alternative embodiment, the radiation-to-frequency converter 1404 can instead be a radiation-to-pulse-width converter. The radiation-to-pulse-width converter can convert the radiation indication into a pulse-width signal. The pulse-width signal is supplied to an output manager 1406. The output manager 1406 arranges when an output is to be provided for the radiation monitoring system 1400. In one embodiment, the output manager 1406 determines that an output indication should be provided based on the width of the pulse of the pulse-width signal.

Figure 14B:
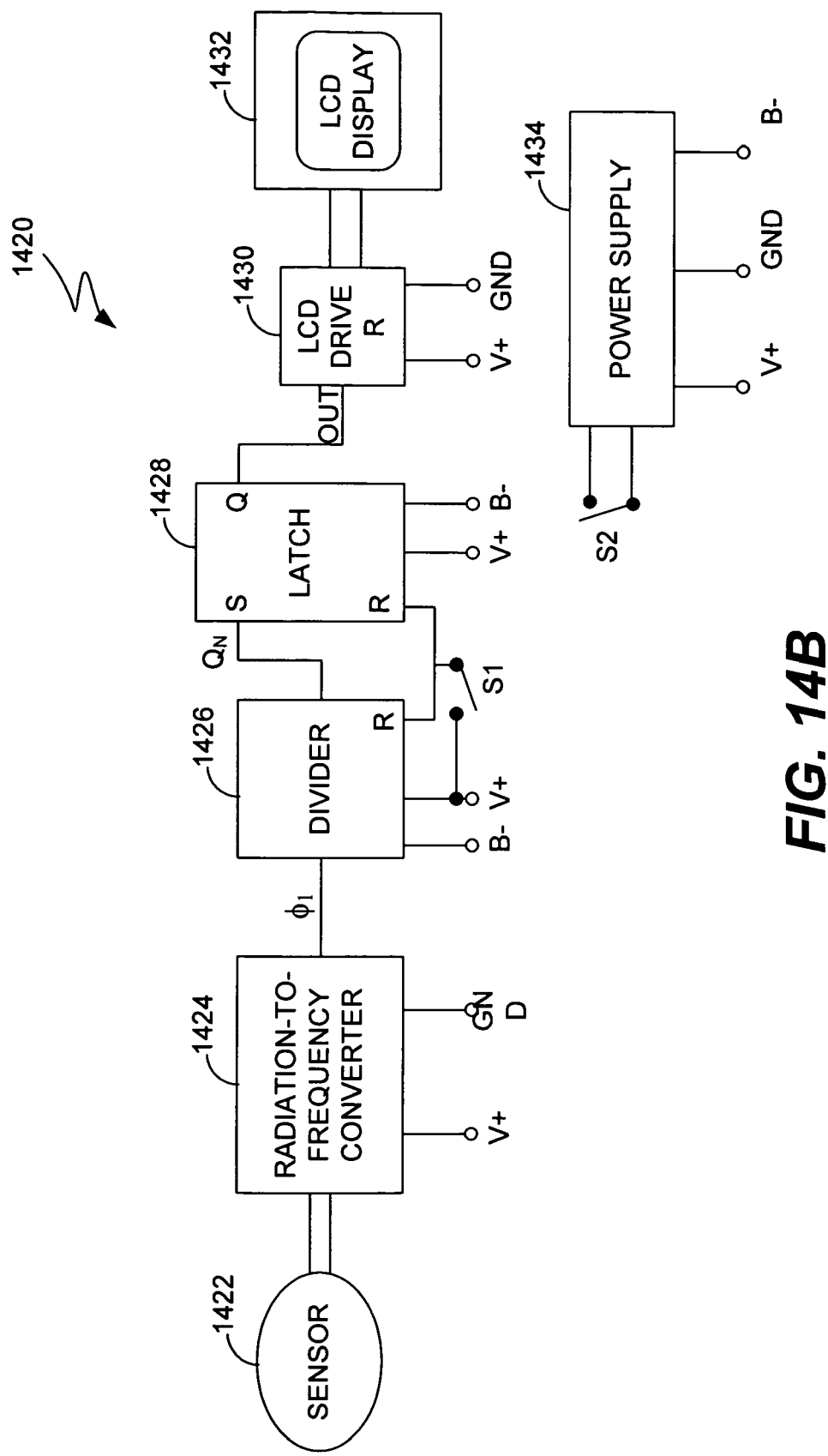
FIG. 14B is a block diagram of a radiation monitoring system according to another embodiment of the invention.

FIG. 14B is a block diagram of a radiation monitoring system 1420 according to another embodiment of the invention. The radiation monitoring system 1420 is, for example, a detailed embodiment of the radiation monitoring system 1400 illustrated in FIG. 14A.

The radiation monitoring system 1420 includes a sensor 1422. The sensor 1422 senses radiation, such as ultraviolet radiation or infrared radiation. The sensor 1422 outputs a radiation indication to a radiation-to-frequency converter 1424. The radiation-to-frequency converter 1424 outputs a frequency signal $\phi_1$ to a divider 1426. The divider 1426 divides the frequency signal $\phi_1$ and outputs a divided frequency signal $Q_N$. The divided frequency signal $Q_N$ is supplied to a latch 1428. As shown in FIG. 14B, in one embodiment, the latch 1428 can be a set-reset type of latch. The output of the latch 1428 is an output signal (OUT). The output signal (OUT) is supplied to a LCD driver 1430. When the output signal (OUT) is high, the LCD driver 1430 causes an output indication to be provided on a LCD display 1432.

Still further, the radiation monitoring system 1420 includes a power supply 1434 that supplies power to various components under the radiation monitoring system 1420. The power supply 1434 outputs a positive voltage (V+), a ground signal (GND), and a negative voltage (B−). The signals provided by the power supply 1434 are supplied to various components of the radiation monitoring system 1420 as shown in FIG. 14B. In addition, the radiation monitoring system 1420 includes a first switch (S1) and a second switch (S2). The first switch (S1) is a reset switch that is coupled to the divider 1426 and the latch 1428. When the first switch (S1) is closed a reset operation occurs so that the divider 1426 and the latch 1428 are reset. Hence, any accumulated data in these components is cleared. As a result, radiation monitoring can be cleared and restarted by closing and then opening the first switch (S1). The second switch (S2) is coupled to the power supply 1434 and serves as an on-off switch. When the second switch (S2) is closed (i.e., "switched on"), the power supply 1434 outputs various voltage signals. On the other hand, when the second switch (S2) is open (i.e., "switched off"), the power supply 1434 does not output the voltage levels.

As noted above, the radiation monitoring system 1420 is an example of a more detailed embodiment of the radiation monitoring system 1400 illustrated in FIG. 14A. As such, the divider 1426 and the latch 1428 together can correspond to the output manager 1406 in one embodiment, and the LCD driver 1430 can corresponds to the output driver 1408 in one embodiment.

Figure 14C:
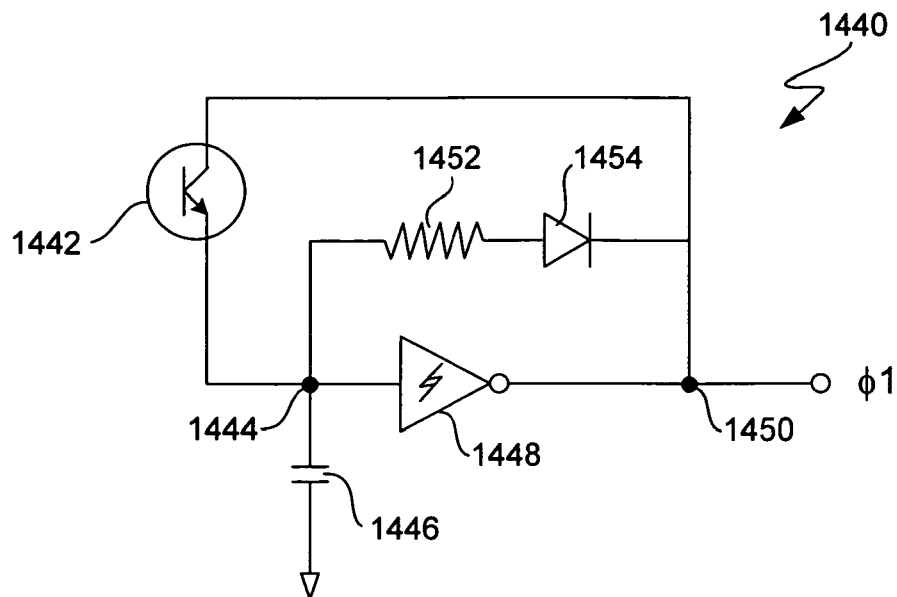
FIG. 14C is a schematic diagram of a radiation-to-frequency converter according to one embodiment of the invention.

FIG. 14C is a schematic diagram of a radiation-to-frequency converter 1440 and a sensor according to one embodiment of the invention. The radiation-to-frequency converter 1440 represents a detailed embodiment for the radiation-to-frequency converter 1424 illustrated in FIG. 14B. As shown in FIG. 14C, the sensor includes a phototransistor 1442 that serves as a radiation sensor. In particular, the phototransistor 1442 can be sensitive to a particular wavelengths of radiation, such as ultraviolet radiation or infrared radiation. As radiation impinges on the phototransistor 1442, a voltage dependent upon the amount of radiation impinging on the phototransistor 1442 is produced at a first node 1444. The first node 1444 is coupled to ground by a capacitor 1446. A Schmitt trigger inverter 1448 couples between the first mode 1444 and a second node 1450. The output of the radiation-to-frequency converter 1440 is provided at the second node 1450 and pertains to the frequency signal $\phi_1$. The phototransistor 1442 is also coupled between the first node 1444 and the second node 1450. In addition, a series combination of a resistor 1452 and a diode 1454 are also coupled between the first node 1444 and the second node 1450. The frequency signal $\phi_1$ being produced at the second node 1450 has a frequency that is dependent upon the resistance of the resistor 1452, the capacitance of the capacitor 1446, the sensitivity of the phototransistor 1442, and the amount of radiation impinging upon the phototransistor 1442. If the first node 1444 is low, the second node 1452 is high. In such a situation, radiation impinging upon the phototransistor 1442 causes the first node 1444 to transition to a "high" level, which then in turn causes the second node 1450 to transition to a "low" level. Subsequently, from such a state, the first node 1444 is discharged to a "low" state in accordance with a time constant set by the resistor 1452 and the capacitor 1446. The cycling continues so that the resulting frequency signal $\phi_1$ is produced. As an example, the resistance of the resistor 1452 can be 10 k ohms, and the capacitance of the capacitor 1446 can be 0.1 microfarads, and the resulting frequency for the resulting frequency signal $\phi_1$ is then about in a range of about 0-400 Hertz. The Schmitt trigger inverter 1448 can be implemented by a CD74HC14 chip, for example. Hence, the radiation-to-frequency converter 1440 can produce a digital output which has a frequency dependent on the amount of impinging radiation. The digital output is also produced in a power-efficient manner. In one embodiment, power-efficiency results because the Schmitt trigger inverter 1448 is power efficient, the capacitor 1446 is rather small, and the resulting frequency signal $\phi_1$ is low. Power consumption can be further reduced by only periodically supplying power to some or all of the components of the radiation-to-frequency converter 1440, or more generally, the radiation monitoring system 1400.

Figure 14D:
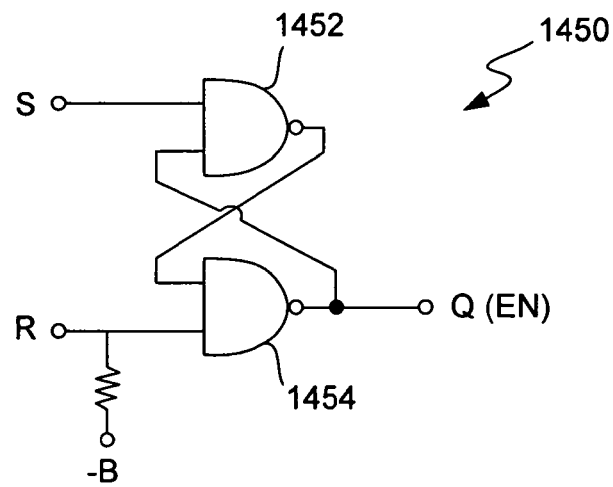
FIG. 14D is a schematic diagram of a latch according to one embodiment of the invention.

FIG. 14D is a schematic diagram of a latch 1450 according to one embodiment of the invention. The latch 1450 represents a detailed embodiment for the latch 1428 shown in FIG. 14B. The latch 1450 includes a first NAND gate 1452 and a second NAND gate 1454. These NAND gates 1452 and 1454 are connected as shown in FIG. 14D.

Figure 14E:
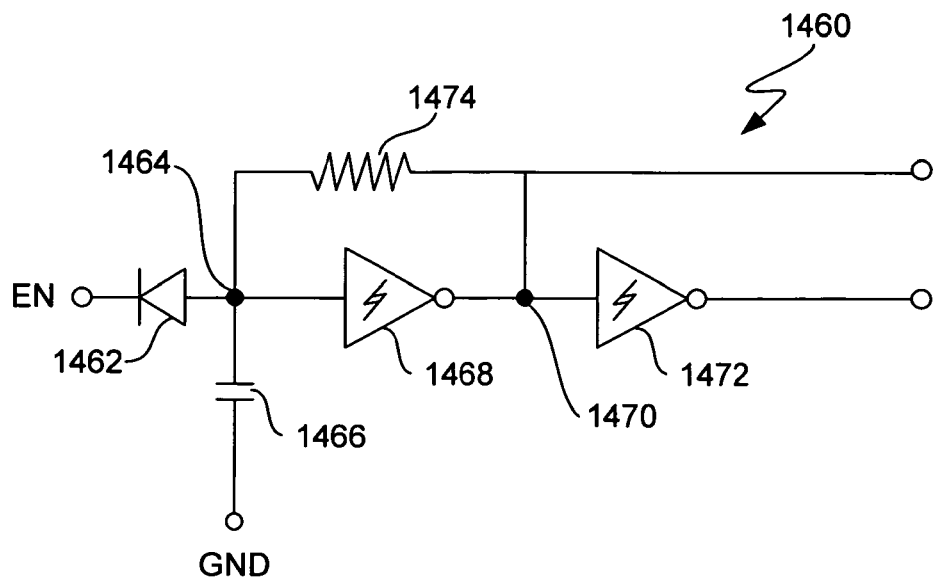
FIG. 14E is a schematic diagram of a LCD driver according to one embodiment of the invention.

FIG. 14E is a schematic diagram of a LCD driver 1460 according to one embodiment of the invention. The LCD driver 1460 represents a detailed embodiment for the LCD driver 1430 illustrated in FIG. 14B. The LCD driver 1460 includes a diode 1462 having a cathode terminal that receives the enable signal (EN) from the latch 1450, and an anode terminal that couples to a first node 1464. The LCD driver 1460 also includes a capacitor 1466 that couples between the first node 1464 and ground. Additionally, the LCD driver 1460 includes a first Schmitt trigger inverter 1468 coupled between the first node 1464 and a second node 1470, and a second Schmitt trigger inverter 1472 connected to the second node 1470. In addition, a resistor 1474 couples the first node 1464 and the second node 1470. The output of the LCD driver 1460 is provided from the second node 1470 and from the output of the second Schmitt trigger inverter 1472. These outputs are the designed to excite the appropriate one or more LCD elements of the LCD display 1432 so as to produce the desired output indication. As an example, the resistance of the resistor 1474 can be 330 k ohms, and the capacitance of the capacitor 1446 can be 0.1 microfarads, and the resulting frequency for the outputs (when enabled) is then about 200 Hertz. The Schmitt trigger inverters can be implemented by a CD74HC14 chip, for example. It should be noted that LCD driver 1460 is designed to excite a single LCD element or a single group of LCD elements. Hence, in cases in which the output indication is to excite multiple LCD elements at different times, additional circuitry would be required.

Figure 14F:
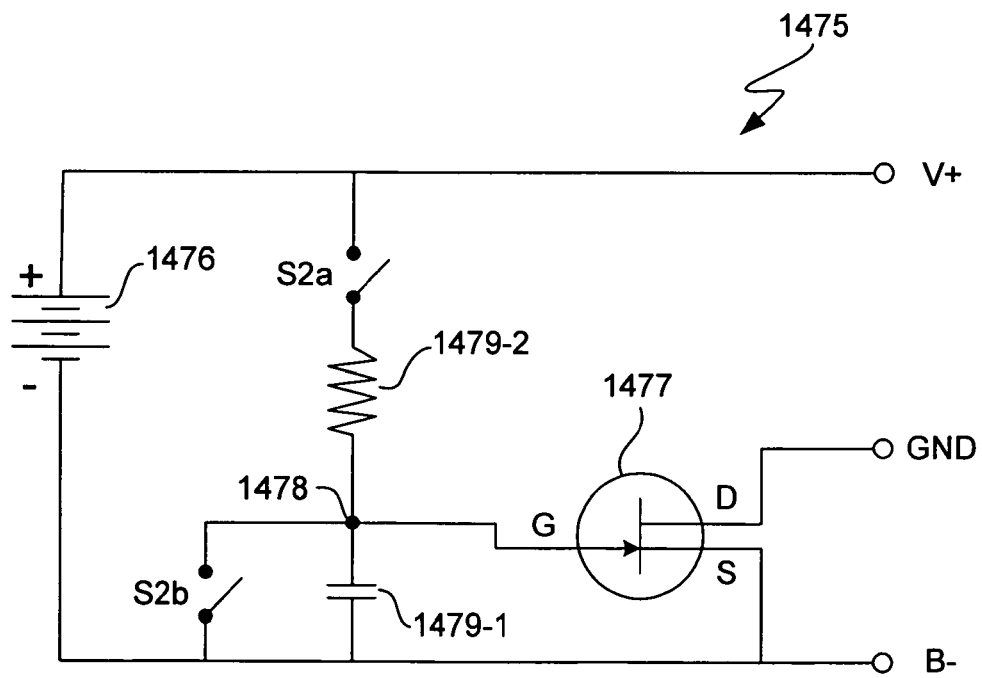
FIG. 14F is a schematic diagram of a power supply according to one embodiment of the invention.

FIG. 14F is a schematic diagram of a power supply 1475 according to one embodiment of the invention. The power supply 1475 represents a detailed embodiment of the power supply 1434 illustrated in FIG. 14B.

The power supply 1475 includes a battery 1476 that is coupled between a positive voltage terminal (V+) then a negative voltage terminal (B−). The power supply 1475 also includes a transistor 1477. In one embodiment, the transistor 1477 is an enhancement type n-channel MOSFET. The drain terminal of the transistor 1477 is coupled to the ground terminal of the power supply 1475, and a source terminal of the transistor 1477 is coupled to the negative voltage terminal (B−). A gate terminal of the transistor 1477 couples to a first node 1478. The first node 1478 is coupled to the negative voltage terminal (B−) by a capacitor 1479-1, and is coupled to the positive voltage terminal (V+) by a resistor 1479-2 and a switch S2a. The switch S2a is closed when the power supply 1475 is "on." The power supply 1475 also includes a switch S2b that is closed when the power supply 1475 is "off." Hence, only one of the switches S2a and S2b are closed at any one point. When the switch S2b is closed, the first node 1478 is coupled to the negative voltage terminal (B−) so that the transistor 1477 is "off." On the other hand, when the switch S2a is closed, the first node 1478 is able to hold a positive voltage which activates the transistor 1477. When the transistor 1477 is activated, the negative voltage provided on the negative voltage terminal (B−) is provided at the ground (GND) terminal. As an example, the resistance of the resistor 1479-2 can be 100 k ohms, and the capacitance of the capacitor 1479-1 can be 0.01 microfarads, and the battery can provide 3 Volts (e.g., 35 mA-H). The transistor 1477 can be implemented by a 2N708 chip, for example.

Figure 14G:
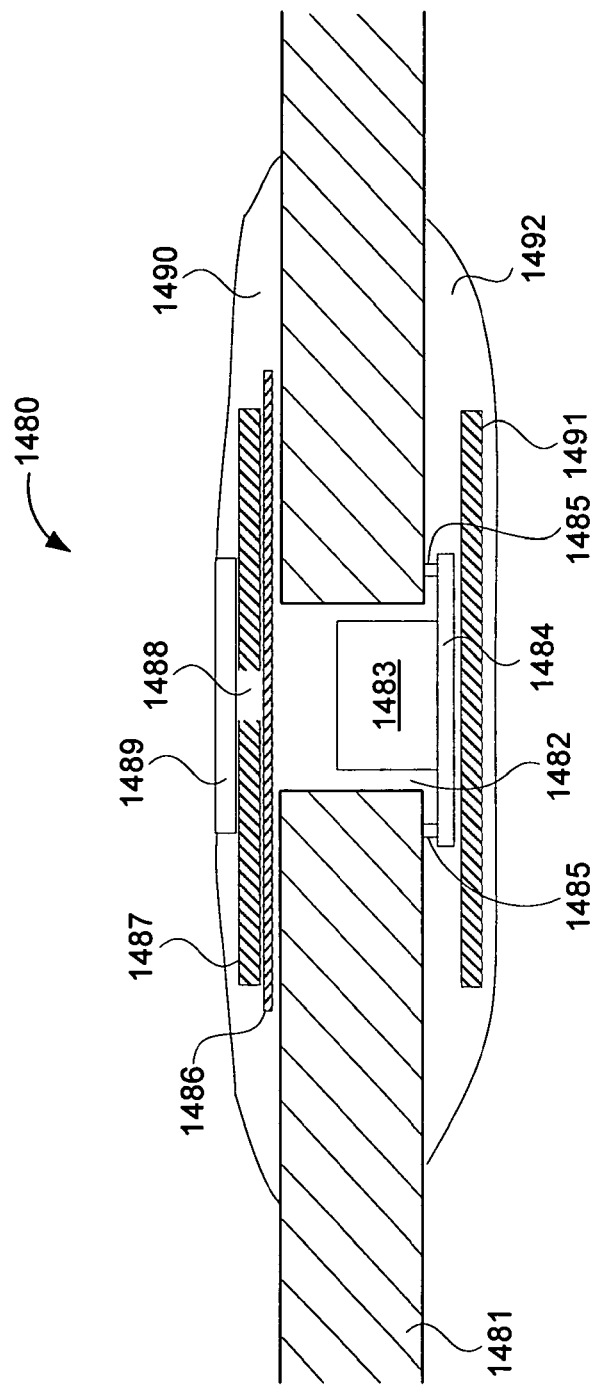
FIG. 14G is a cross-sectional view of a UV detector arrangement according to one embodiment of the invention.
Figure 14H:
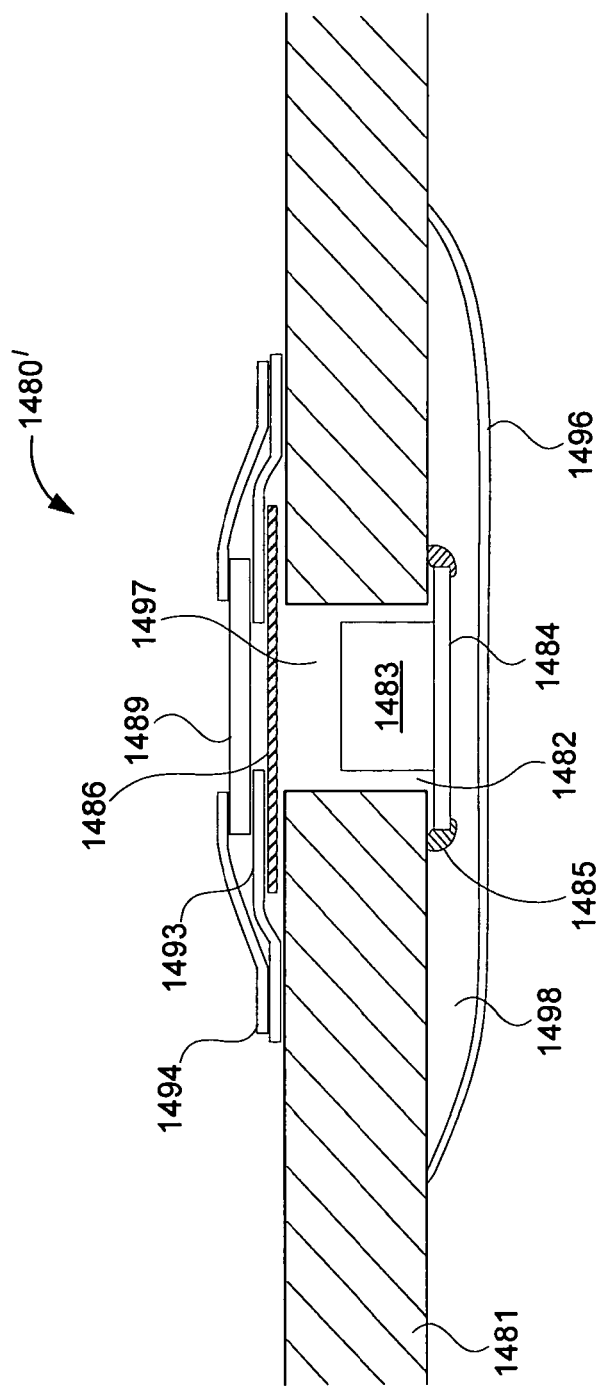
FIG. 14H is a cross-sectional view of a UV detector arrangement according to one embodiment of the invention.
Figure 14I:
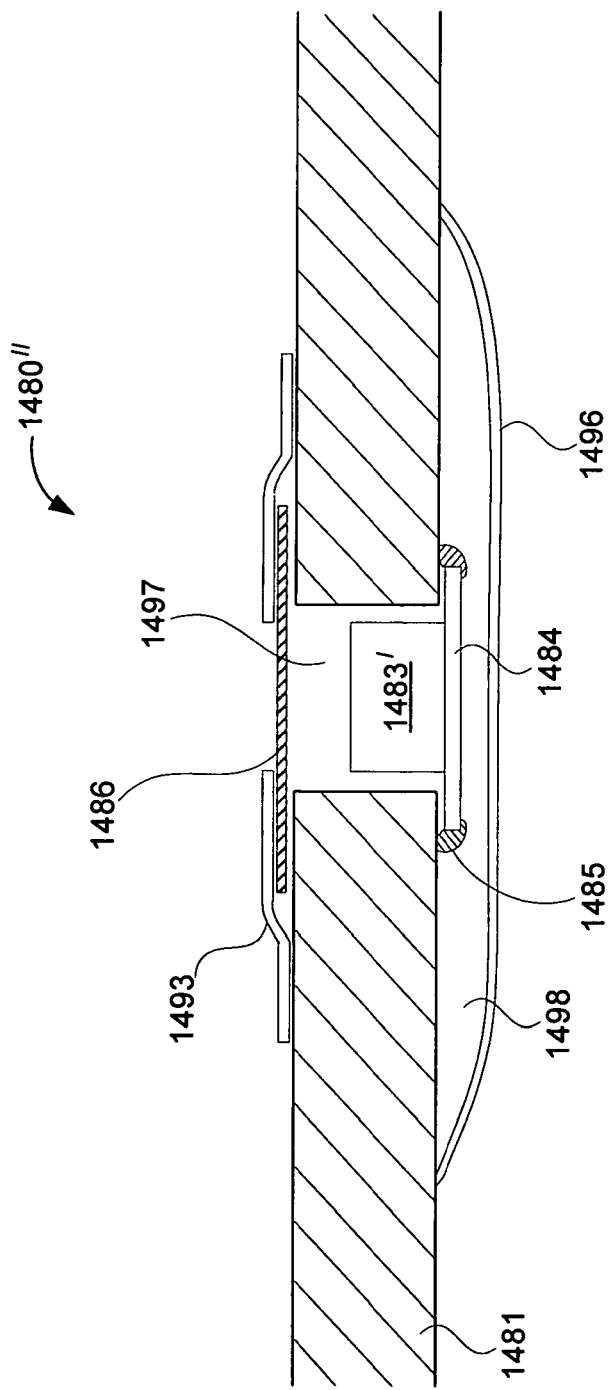
FIG. 14I is a cross-sectional view of a UV detector arrangement according to one embodiment of the invention.

In one embodiment, a radiation detector can be mounted on a substrate and couple to other circuitry so that radiation monitoring can be performed. The manner in which the radiation detector is mounted to the substrate can vary with implementation. In one implementation, the substrate is a printed circuit board (PCB) that supports not only the radiation detector but also the other circuitry. FIGS. 14G-14I illustrate examples of a few possible implementations in the case where the radiation detector is a UV detector; however, other implementations can be utilized.

FIG. 14G is a cross-sectional view of a UV detector arrangement 1480 according to one embodiment of the invention. The UV detector arrangement 1480 is formed on a printed circuit board 1481 that contains a hole (or opening) 1482. A phototransistor 1483 is placed in the hole 1482. A base 1484 for the phototransistor 1483 is used to electrically connect the phototransistor 1483 to the printed circuit board 1481 via solder 1485. A film of aluminized Mylar 1486 is attached to the top of the printed circuit board 1481 at the hole 1482. The aluminized Mylar 1486 serves as a sensitivity reducer since it generally attenuates the radiation (e.g., UV or IR radiation) that impinges on the phototransistor 1483. The aluminized Mylar 1486 can be attached to the printed circuit board 1481 by an adhesive, such as epoxy. Attached to the top of the aluminized Mylar 1486 is an aluminum sheet 1487 with an opening 1488. The opening 1488 corresponds to, but has a substantially smaller diameter than the hole 1482. Hence, the aluminum sheet 1487 further restricts radiation (i.e., restricts volume of radiation) impinging on the phototransistor 1483. An optical filter 1489 is placed over the aluminum sheet 1487 at the vicinity of the hole 1482. As an example, the optical filter 1489 primarily passes UV radiation. The UV radiation then is limited by the opening 1488 in the aluminum sheet 1487, attenuated by the aluminized Mylar 1486, and then the attenuated UV radiation is sensed by the phototransistor 1483. The aluminum sheet 1487 and the optical filter 1489 can be attached with an adhesive, such as epoxy.

Optionally, the back side of the printed circuit board 1481 at the vicinity of the phototransistor 1483 can attenuate or block radiation that might otherwise impinge on and be sensed by the phototransistor 1483. As shown in FIG. 14G, an aluminum sheet 1491 can be attached to the back side of the printed circuit board 1481 behind the phototransistor 1483. The aluminum sheet 1491 can be attached with an adhesive, such as epoxy.

Finally, the top of the UV detector arrangement 1480, except for the optical filter 1489, can be encapsulated by a top encapsulant 1490. For example, the top encapsulant 1490 can be epoxy. The bottom of the UV detector arrangement 1480 can be encapsulated by a bottom encapsulant 1492. For example, the bottom encapsulant 1492 can be epoxy. The epoxy used for the encapsulant 1490 or 1492 can be opaque (e.g., block epoxy) to further assist in blocking radiation.

FIG. 14H is a cross-sectional view of a UV detector arrangement 1480' according to one embodiment of the invention. The UV detector arrangement 1480' is formed on a printed circuit board 1481 that contains a hole (or opening) 1482. A phototransistor 1483 is placed in the hole 1482. A base 1484 for the phototransistor 1483 is used to electrically connect the phototransistor 1483 to the printed circuit board 1481 via solder 1485. A film of aluminized Mylar 1486 is attached to the top of the printed circuit board 1481 at the hole 1482. The aluminized Mylar 1486 serves as a sensitivity reducer since it generally attenuates the radiation that impinges on the phototransistor 1483. The aluminized Mylar 1486 can be attached to the printed circuit board 1481 by foil tape 1493 (that uses an adhesive). The foil tape 1493 does not cover the region of the aluminized Mylar 1486 above the phototransistor 1483. The foil tape 1493 further restricts radiation (i.e., restricts volume of radiation) impinging on the phototransistor 1483. Attached to the top of the foil tape 1493 is an optical filter 1489 at the vicinity of the hole 1482. Foil tape 1494 (that uses an adhesive) can be used to hold the optical filter 1489 in position. The foil tape 1494 may also serve to restrict radiation impinging on the phototransistor 1483. As an example, the optical filter 1489 primarily passes UV radiation. The UV radiation can then be limited by the opening in the foil tapes 1493 and 1494 as well as the aluminized Mylar 1486. A cavity 1497 in the hole 1482 above the phototransistor 1483 can be filled with an epoxy, such as clear epoxy.

Optionally, the back side of the printed circuit board 1481 at the vicinity of the phototransistor 1483 can attenuate or block radiation that might otherwise impinge on and be sensed by the phototransistor 1483. As shown in FIG. 14H, a foil tape 1496 can be attached to the back side of the printed circuit board 1481 behind the phototransistor 1483. A bottom cavity 1498 between the back side of the printed circuit board 1481 and the foil tape 1496 can be filled with an opaque substance, e.g., block epoxy, to further assist in attenuating or blocking radiation.

FIG. 14I is a cross-sectional view of a UV detector arrangement 1480" according to one embodiment of the invention. The UV detector arrangement 1480" shown in FIG. 14I is generally similar to the UV detector arrangement 1480' shown in FIG. 14H, except that the UV detector arrangement 1480" does not use the optical filter 1489 or the foil tape 1494. In such an embodiment, an optical filter (such as the optical filter 1489) is not required because the spectral response of the phototransistor 1483' is appropriate without filtering or because a coating provided on the phototransistor 1483' or its housing (package) effectuates similar filtering and obviates the need for a separate optical filter (such as the optical filter 1489).

The phototransistor 1483 or 1483' shown in FIGS. 14G-14I can be a photodiode as noted elsewhere in this patent application. In addition, the phototransistor 1483 or 1483' (or photodiode) can have a height greater than the thickness of the printed circuit board 1481.

Figure 14J:
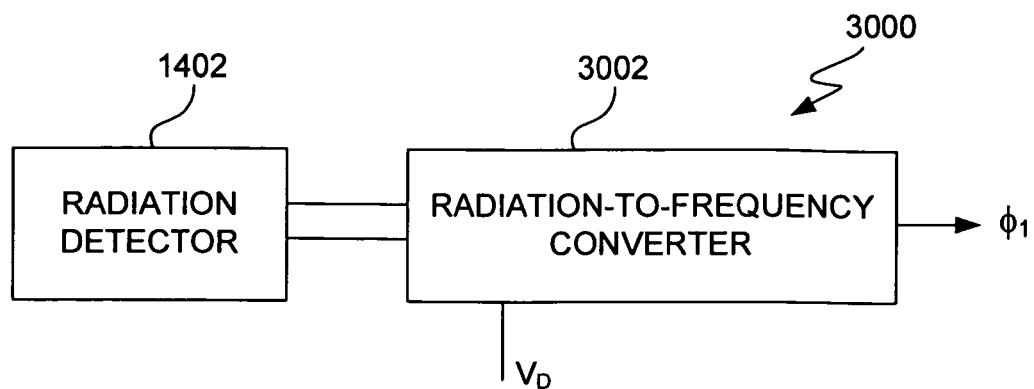
FIG. 14J is a partial block diagram of a radiation monitoring system according to one embodiment of the invention.

FIG. 14J is a partial block diagram of a radiation monitoring system 3000 according to one embodiment of the invention. The radiation monitoring system 3000 represents one implementation of a portion of the radiation monitoring system 1400 illustrated in FIG. 14A or a portion of the radiation monitoring system 1420 illustrated in FIG. 14B. In particular, the radiation monitoring system 3000 provides reduced power operation. The reduced power operation can substantially extend battery life. In this embodiment, a radiation-to-frequency converter 3002 receives a low duty cycle signal $V_D$. The low duty cycle signal $V_D$ causes the radiation-to-frequency to periodically operate briefly. The duty cycle and frequency for the low duty cycle signal $V_D$ can vary with implementation.

Figure 14K:
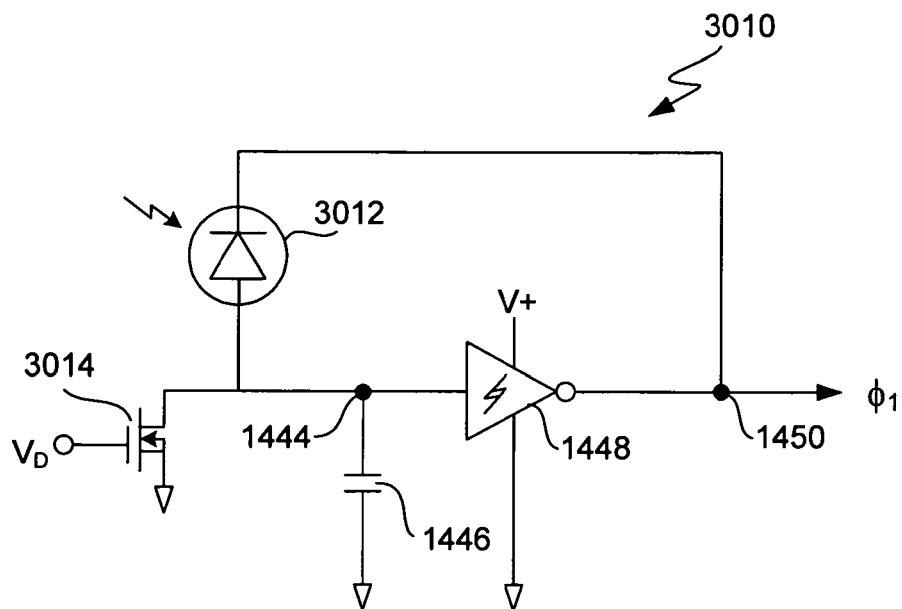
FIG. 14K is a schematic diagram of a radiation-to-frequency converter and a sensor according to one embodiment of the invention.

FIG. 14K is a schematic diagram of a radiation-to-frequency converter 3010 and a sensor according to one embodiment of the invention. The radiation-to-frequency converter 3010 is generally similar to the radiation-to-frequency converter 1440 illustrated in FIG. 14C. However, the radiation-to-frequency converter 3010 uses a photodiode 3012 instead of the phototransistor 1442. Also, the resistor 1452 and the diode 1454 illustrated in FIG. 14C are typically not needed as the photodiode 3012 is a diode and often includes an internal resistance. One example of such a photodiode is Everlight PD-15-22 (another is Everlight PD-93-21), though various different photodiodes can be used, and an optical filter may be used with the photodiode. Additionally, the radiation-to-frequency converter 3010 also include a transistor 3014. The transistor 3014 is controlled by the low duty cycle signal $V_D$ such that the low power operation results. Namely, only when the low duty cycle signal $V_D$ is "low" is significant power being consumed by the radiation monitoring system to monitor radiation. As a result, the radiation monitoring system can operate under battery power for extended durations.

Figure 14L:
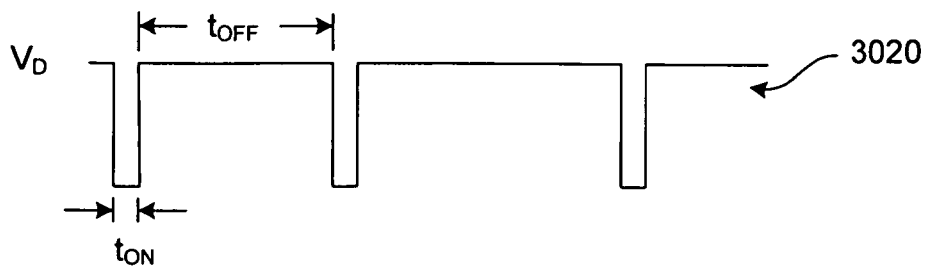
FIG. 14L is a diagram of a representative waveform of a low duty cycle signal $V_D$.

FIG. 14L is a diagram of a representative waveform 3020 of a low duty cycle signal $V_D$. The low duty cycle signal $V_D$ is "low" much less than it is "high." In this embodiment, radiation monitoring occurs when low duty cycle signal $V_D$ is "low." Hence, the on time for a periodic low duty cycle signal $V_D$ is denoted $t_{ON}$ and the off time is denoted $t_{OFF}$. As an example, the on time $t_{ON}$ can be 0.5 seconds, while the off time $t_{OFF}$ can be 128 seconds (which is a duty cycle of 256 to 1.

Figure 14M:
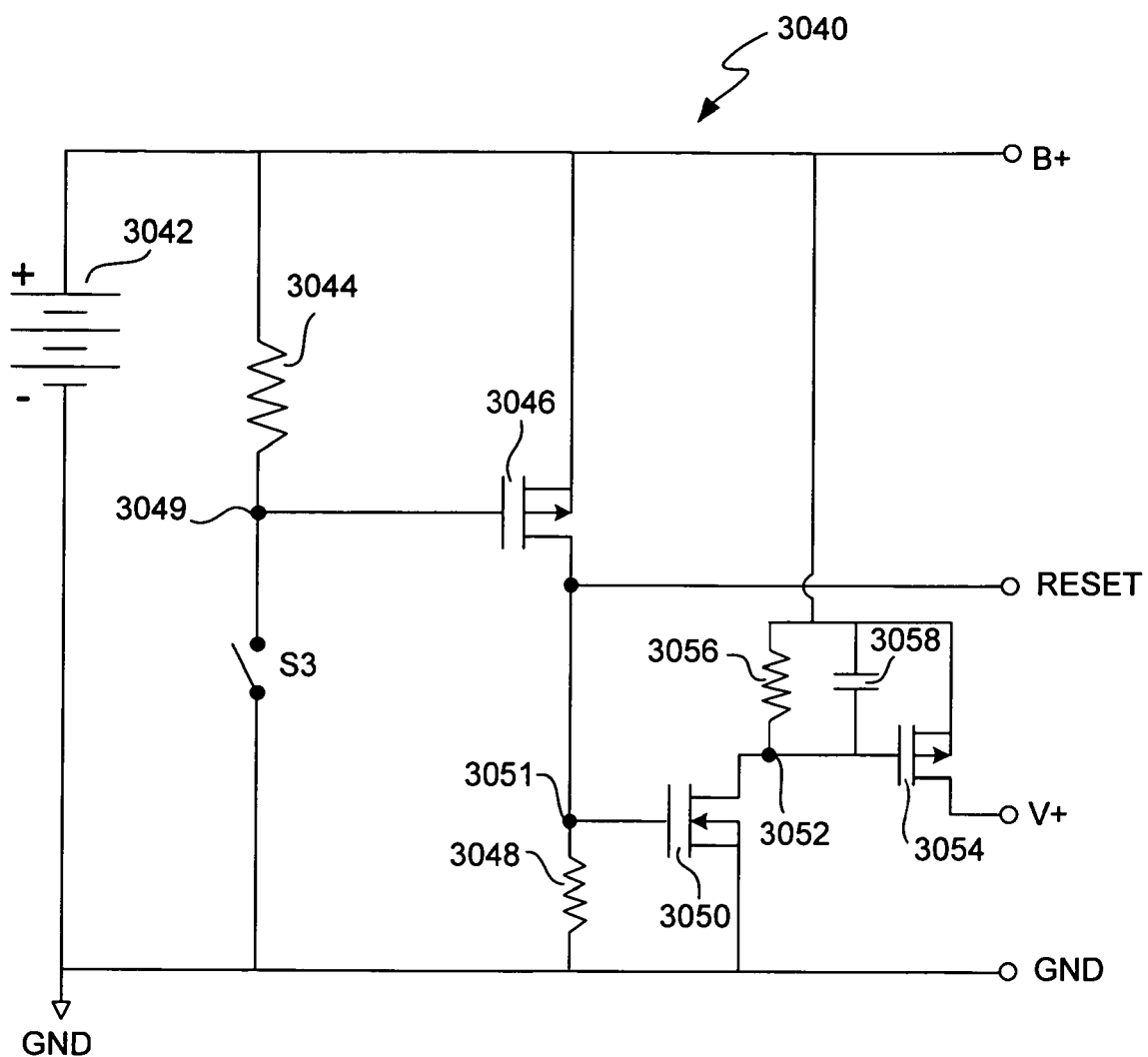
FIG. 14M is a schematic diagram of a power supply another according to one embodiment of the invention.

FIG. 14M is a schematic diagram of a power supply 3040 according to one embodiment of the invention. The power supply 3040 represents a detailed embodiment for a power supply that could be an alternative design for the power supply 1434 illustrated in FIG. 14B.

The power supply 3040 includes a battery 3042 that is coupled between a positive voltage terminal (B+) and ground terminal (GND). The power supply 3040 includes an on/off switch S3. When the switch S3 is closed the power supply is turned on. In one implementation, the switch S3 is a push button switch that is normally open (i.e., not close).

The power supply 3040 also includes a resistor 3044 and a transistor 3046. In one embodiment, the transistor 3046 is an enhancement type p-channel MOSFET. The drain terminal of the transistor 3046 is coupled to the ground terminal (GND) of the power supply 3040 via a resistor 3048, and a source terminal of the transistor 3046 is coupled to the positive voltage terminal (B+) of the battery 3042. A gate terminal of the transistor 3046 is coupled to a first node 3049. The first node 3049 is coupled to the positive voltage terminal (B+) by the resistor 3044, and can be coupled to the ground terminal (GND) via the switch S3. The power supply 3040 also includes a transistor 3050, having a gate terminal coupled to a second node 3051, a source terminal connected to the ground terminal (GND), and a drain terminal connected to a third node 3052. In one embodiment, the transistor 3050 is an enhancement type n-channel MOSFET. Further, the power supply 3040 includes a transistor 3054, a resistor 3056 and a capacitor 3058. In one embodiment, the transistor 3054 is an enhancement type p-channel MOSFET. The gate terminal of the transistor 3054 connects to the third node 3052, the source terminal of the transistor 3054 connects to the positive voltage terminal (B+), and the drain terminal of the transistor 3054 connects to a voltage output terminal (V+). The resistor 3056 and the capacitor 3058 are connected in parallel between the positive voltage terminal (B+) and the third node 3052.

The operation of the power supply 3040 can be briefly explained as follows. When the switch S3 is press (momentarily), the transistor 3046 pulls the second node 3051 to approximately the positive voltage terminal (B+), which activates the transistor 3050. When the transistor 3050 is activated, the third node is pulled to approximately ground, which activates the transistor 3054. When the transistor 3054 is activated, the voltage output terminal (V+) is capable of outputting power for use by other circuitry. Since the switch S3 is soon released, the transistors 3046 and 3050 deactivate. However, the transistor 3054 remains on for a period of time determined by a time constant determined by the resistor 3056 and the capacitor 3058. Hence, during the period of time, charge from the capacitor 3058 is slowly discharged. Once substantially discharged, the transistor 3054 deactivates, thus ceasing output of any power to the other circuitry. In effect, the power supply 3040 automatically turns off after the period of time. As an example, the period of time can be 12 hours (e.g., representing daily usage of a radiation monitoring system). The power supply 3040 can also receive a reset signal that serves to restart any "auto-off" timing that may be used.

It should be noted that a power supply for a radiation monitoring system can implemented in various ways. The power supply 1475 illustrated in FIG. 14F uses an "on" switch and an "off" switch. The power supply 3040 in FIG. 14M uses a single "on" switch (e.g., push button) and an "auto-off" feature. In still another embodiment, the power supply, and thus the radiation monitoring system, can always be powered on. With CMOS transistor devices, the power consumption is relatively low such that a radiation monitoring system could be battery powered for an extended period of time without the need to recharge or replace the battery (i.e., long battery life). When the radiation monitoring is only briefly performed periodically, such as discussed above with reference to FIGS. 14J, 14K and 14L, the power consumption is particularly low and the battery life can be particularly long.

Figure 14N:
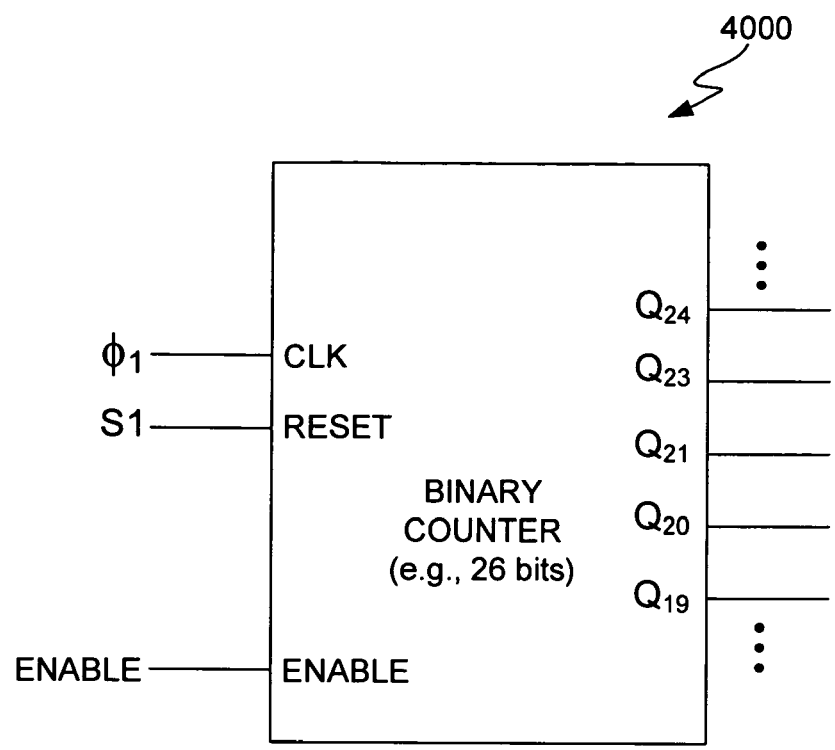
FIG. 14N is a diagram of a binary counter according to one embodiment of the invention.

FIG. 14N is a diagram of a binary counter 4000 according to one embodiment of the invention. The binary counter 4000 is, for example, suitable for use as at least a portion of the divider 1426 illustrated in FIG. 14B. As an example, the binary counter 4000 can be a 26-bit counter. The inputs to the binary counter 4000 include the frequency signal $\phi_1$ from a radiation-to-frequency converter (e.g., radiation-to-frequency converter 1424), a reset signal (such as from a switch S1), and an enable signal. The switch S1 is, for example, a push-button type switch. The binary counter 4000 can have a plurality of output lines (e.g., twenty-six (26) output lines), of which five such lines $Q_{19}$ through $Q_{24}$ are illustrated. These output are representative outputs that might be utilized by subsequent circuitry to control an output device. However, it should be understood that other output lines could alternatively be used. The enable input to the binary counter 4000 permits the binary counter to count when "high" but stops the binary counter 4000 from counting when "low."

Figure 14O:
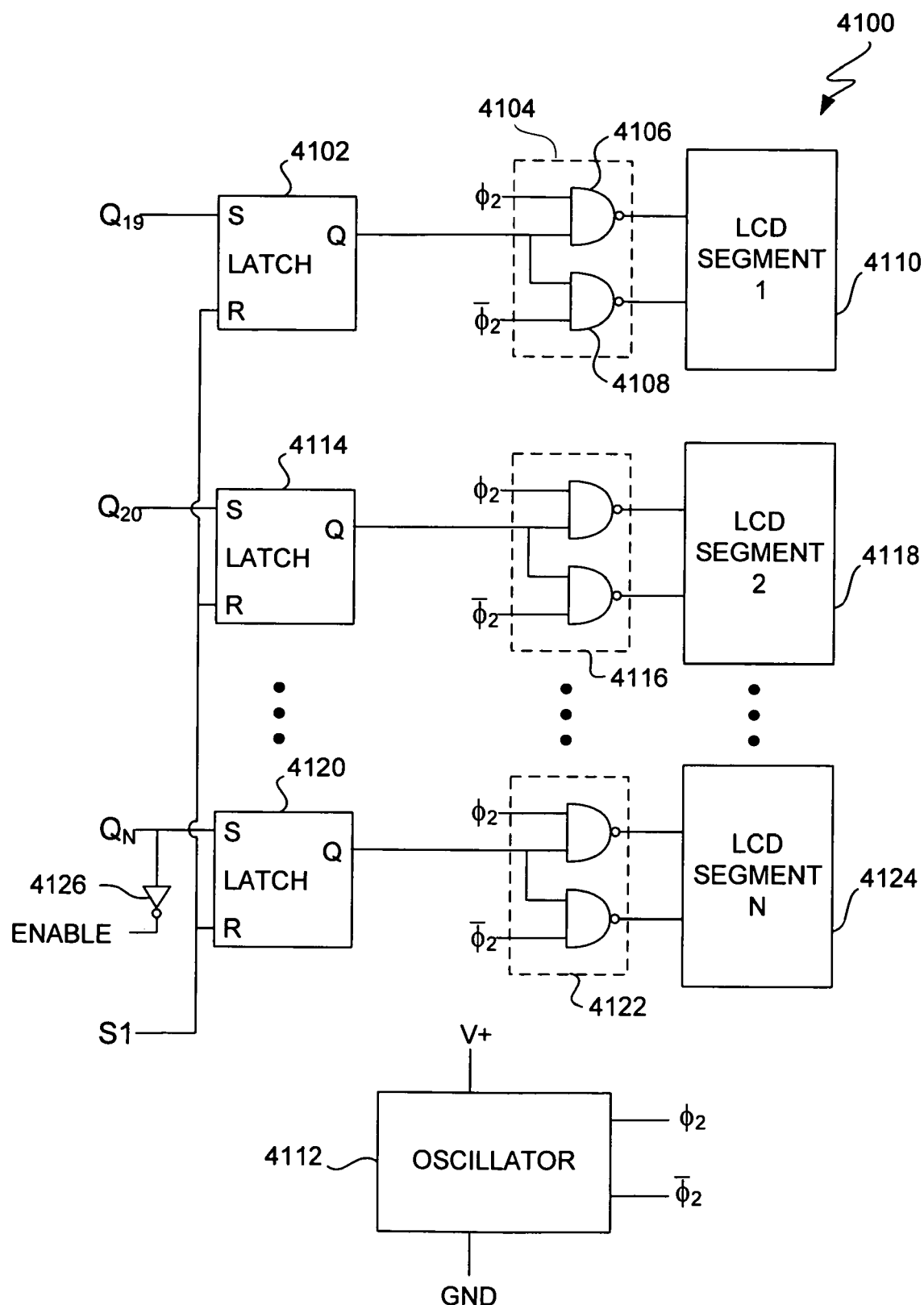
FIG. 14O is a block diagram of latch-driver circuitry according to one embodiment of the invention.

FIG. 14O is a block diagram of latch-driver circuitry 4100 according to one embodiment of the invention. In one embodiment, the latch-driver circuitry 4100 can correspond to the latch 1428, the LCD driver 1430 and the LCD display 1432 as shown in FIG. 14B.

In this embodiment, the latch-driver circuitry 4100 has the capability to separately drive a plurality of different segments. These segments can be segments of a LCD display and can be combined to form symbols or charts. For example, in one embodiment, the LCD segments can be utilized to form a bar graph output.

The latch-driver circuitry 4100 includes a latch 4102 that receives an input associated with output $Q_{19}$ from a divider (e.g., the binary counter 4000). The output of the latch 4102 is supplied to a LCD driver 4104. The LCD driver 4104 includes NAND gates 4106 and 4108. The outputs of the NAND gates 4106 and 4108 are supplied to a LCD segment-1 4110. The LCD driver 4104 also includes frequency signals $\phi_2$ and/$\phi_2$ from an oscillator 4112.

The latch-driver circuitry 4100 further includes a latch 4114, a LCD driver 4116 and a LCD segment-2 4418. The latch 4114 receives an input signal associated with the output $Q_{20}$ from the divider (e.g., the binary counter 4000). Likewise, for one or more other outputs from the divider (e.g., the binary counter 4000), the latch-driver circuitry 4100 can include a latch, a LCD driver and a LCD segment. In this regard, the output $Q_N$ from the divider represents a generic output signal which is supplied to a latch 4120. The output of the latch 4120 is supplied to a LCD driver 4122. The output of the display driver 4122 is coupled to a LCD segment-N 4124. Additionally, each of the latches 4102, 4114 and 4120 receives a reset signal from a switch S1.

Still further, the output $Q_N$ is coupled to an enable terminal of the divider (e.g., the binary counter 4000) via an inverter 4126. When the signal $Q_N$ is high, the LCD segments are fully illuminated; hence, the enable signal output by the inverter 4126 is "low" so that the divider (e.g., the binary counter 4000) is disabled, until reset.

Figure 14P:
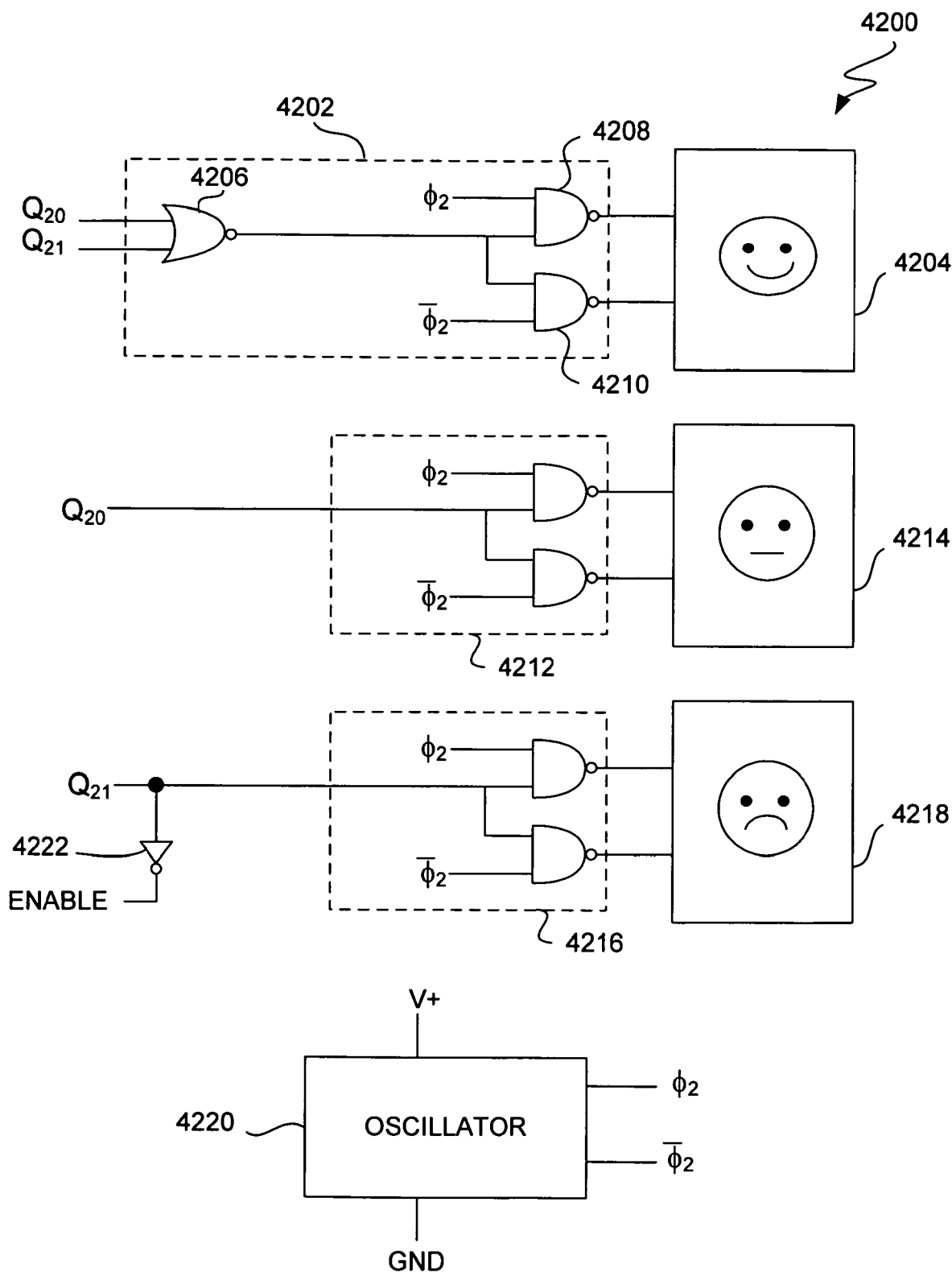
FIG. 14P is a block diagram of driver circuitry according to one embodiment of the invention.

FIG. 14P is a block diagram of driver circuitry 4200 according to one embodiment of the invention. The driver circuitry 4200 is coupled to one or more outputs from a divider (e.g., the binary counter 4000). In this illustrated embodiment, the driver circuitry 4200 couples to the outputs $Q_{20}$ and $Q_{21}$.

The driver circuitry 4200 includes a LCD driver 4202 that receives the outputs $Q_{20}$ and $Q_{21}$ from the divider (e.g., the binary counter 4000). These signals $Q_{20}$ and $Q_{21}$ are supplied to a NOR gate 4206 whose output is supplied to NAND gates 4208 and 4210. The outputs of the NAND gates 4208 and 4210 are supplied to a LCD graphic segment-1 4204. As shown in FIG. 14P, the LCD graphic segment-1 4204 represents a "happy" smiley face.

Additionally, the output $Q_{20}$ is supplied to a LCD driver 4212 whose output in turn drives a LCD graphic segment-2 4214. Further, the output $Q_{21}$ is supplied to a LCD driver 4216 whose output in turn drives a LCD graphic segment-3 4218. As shown in FIG. 14P, the LCD graphic segment-2 4214 is a "neutral" smiley face, and the LCD graphic segment-3 4248 is a "sad" smiley face. It should be understood that various other graphical symbols or images can be used in place of smiley faces.

The driver circuitry 4200 also includes an oscillator 4220 that supplies the output frequency signals $\phi_2$ and/$\phi_2$ to the LCD drivers 4202, 4212 and 4216. The driver circuitry 4200 further includes an inverter 4222 coupled to the output $Q_{21}$. The output of the inverter 4222 is coupled to the enable terminal of the divider (e.g., the binary counter 4000) so that the divider (e.g., the binary counter 4000) is stopped once the output $Q_{21}$ is "high."

Figure 14Q:
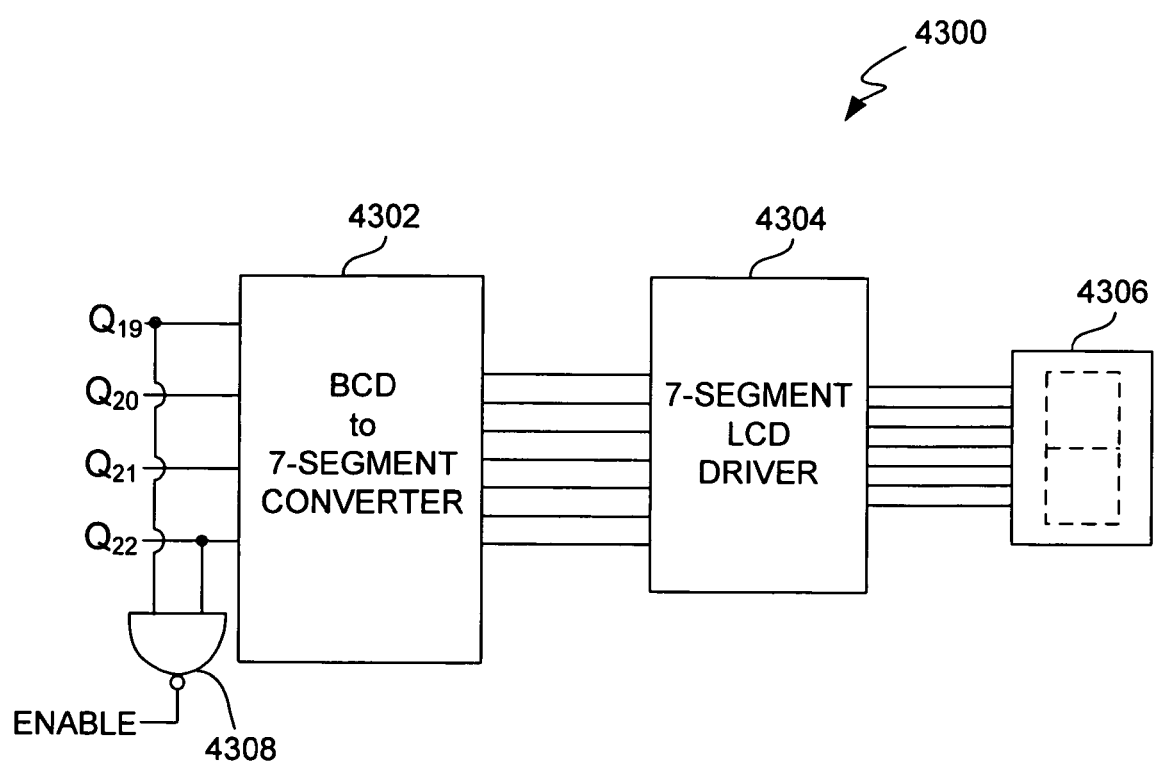
FIG. 14Q is a block diagram of driver circuitry according to another embodiment of the invention.

FIG. 14Q is a block diagram of driver circuitry 4300 according to another embodiment of the invention. In this embodiment, the output is a numerical value. In one embodiment, the driver circuitry 4300 can correspond to the latch 1428, the LCD driver 1430 and the LCD display 1432 as shown in FIG. 14B.

In this embodiment, the driver circuitry 4300 has the capability to separately drive a plurality of different segments. These segments are segments of a LCD display and can be combined to form numerical values. For example, in one embodiment, the segments can be utilized to output numerical values from 0-9. In other embodiments, the range of numerical outputs could be more or less than 0 through 9.

The driver circuitry 4300 receives a plurality of outputs from a divider (e.g., the binary counter 4000), such as outputs $Q_{19}$, $Q_{20}$, $Q_{21}$ and $Q_{22}$. These outputs are supplied to a BCD-to-7 segment converter 4302. The output of the converter 4302 is supplied to a 7-segment LCD driver 4304. The 7-segment LCD driver 4304 couples to a 7-segment display 4306. Here, the outputs from the divider (e.g., the binary counter 4000) are converted such that a numerical range is output on the 7-segment display 4306. For example, the 7-segment display 4306 can display a number from 0 to 9 indicating a quantity or intensity of radiation. A NAND gate 4308 is coupled to the output $Q_{19}$ and the output $Q_{22}$ so as to decode a value of "9" at the outputs and cause the enable signal to go "low", thereby ceasing operation of the divider (e.g., binary counter 4000) when such reaches its maximum value.

Figure 14R:
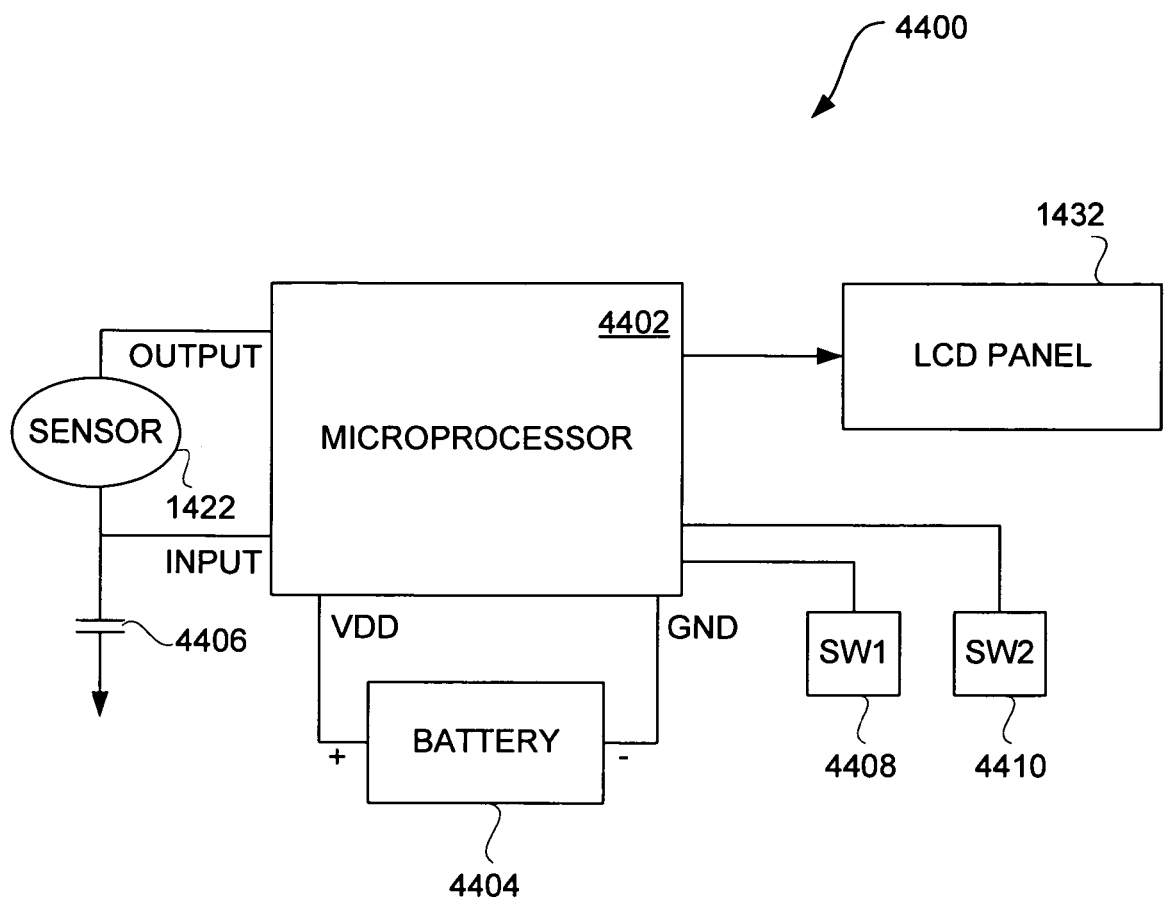
FIG. 14R is a block diagram of a radiation monitoring system according to another embodiment of the invention.

The radiation monitoring system can also be implemented by primarily digital design. FIG. 14R is a block diagram of a radiation monitoring system 4400 according to another embodiment of the invention. The radiation monitoring system 4400 uses a microcontroller 4402 and can be considered a primarily digital implementation. As an example, the radiation monitoring system 4400 can implement functions similar to the radiation monitoring system 1400 shown in FIG. 14A as well as the radiation monitoring system 1420 shown in FIG. 14B, using either radiation-to-frequency techniques or, alternatively, radiation-to-pulse-width techniques. However, the flexibility provided by the digital implementation is not limited to implementing these particular techniques.

In addition to the microcontroller 4402, the radiation monitoring system 4400 includes a battery 4404 and a capacitor 4406. The battery 4404 provides power to the microcontroller 4402. The capacitor 4406 together with the sensor 1422 and the microcontroller 4402 can be used to monitor radiation. The microcontroller 4402 also determines whether and what to display on the LCD panel 1432. In one implementation, the microcontroller 4402 can include a display driver for driving the LCD panel 1432. One example of a suitable microcontroller for the microcontroller 4402 is the 4-bit microcontroller TM8704 available from Tenx Technology, Inc.

In one embodiment, the monitoring of radiation by the radiation monitoring system 4400 is performed using a pulse-width measurement technique. In such an embodiment, periodically, the microcontroller 4402 outputs a HIGH signal (digital "1" signal) on an OUTPUT pin and then monitors an INPUT pin for a HIGH signal. In one implementation, the sensor 1442 is implemented by a photodiode having its anode connected to the INPUT pin and its cathode connected to the OUTPUT pin. When the photodiode detects radiation, the photodiode conducts. Then, the HIGH signal on the OUTPUT pin propagates to the INPUT pin and charges up the capacitor 4406. The higher the intensity of the radiation, the faster the capacitor 4406 is charged to the HIGH signal. The duration of time between the outputting of the HIGH signal on the OUTPUT pin and the detection of a HIGH signal on the INPUT pin is dependent on the radiation intensity detected by the sensor 1422 and the capacitance of the capacitor 4406. The microcontroller 4402 measures this duration of time. The radiation intensity measured by the microcontroller 4402 is thus inversely proportional to the period of time. An intensity value can be computed as a value that is proportional to a constant divided by the period of time. This intensity value is then accumulated with the prior accumulated intensity value to determine a current accumulated intensity value. The current accumulated intensity value is then compared to one or more threshold levels to determine an output indication to be displayed on the LCD panel 1432. As discussed elsewhere in this patent application, the output indication can take many different forms. One exemplary form is a series of increasing bars that are activated as the accumulated current intensity value exceeds a corresponding series of threshold levels.

In one embodiment, upon turn-on of the radiation monitoring system 4400, such as via a switch (SW1) 4408, the current accumulated intensity value maintained by the microcontroller 4402 can be cleared or set to zero. Hence, the turn-on can also act as a reset. In an alternative embodiment, the current accumulated intensity value could be very gradually reduced to provide a slow discharge of the accumulated intensity value as a function of time. In the alternative embodiment, the current accumulated intensity value need not be reset.

In one embodiment, to assist in the efficient power utilization of the radiation monitoring system 4400, the microcontroller 4402 can be placed in a low power state when not acquiring a radiation measurement. This can be achieved by a sleep, halt or stop mode or other approaches to reduce power consumption. Then, periodically the microcontroller would briefly operate in an active or non-low power state to acquire and accumulate the radiation measurement. The periodicity can vary with implementation, such as from fifteen (15) seconds to fifteen (15) minutes. The greater the period the longer battery life, but the less the accuracy. A reasonable solution might use a period on the order of about three (3) minutes. In acquiring the period of time (for the radiation measurement), a maximum time-out can be provided so that power is not wasted. Typically, if the radiation monitoring system is monitoring light or UV radiation in the dark (or for UV, the environment has very low UV, such as at night or inside a car with windows closed), then the time period being measured would time-out. Thereafter, if desired, the periodicity by which re-measurement is performed can be made longer so as to further conserve power. In another embodiment, once the radiation monitoring system 4400 is turned-on, it can remain on for a predetermined period of time and then automatically turn itself off (or enter a very low power mode). For example, after being turned-on with no user input for eight (8) hours, the radiation monitoring system 4400 can automatically turn itself off.

The radiation monitoring system 4400 can also include a second switch (SW2) 4410 to enable a user's skin type to be selected. For example, the second switch 4410 can provide different switch positions for different skin types (e.g., light, medium and dark). The switch position can affect the various threshold levels that are used when comparing with the current accumulated intensity value to determine an output indication to be displayed on the LCD panel 1432. As an example, when the output indication is presented as a series of five segments (S1-S5) of increasing bars that are activated as the accumulated current intensity value exceeds a series of threshold levels, Table I provided below provides illustrative threshold levels for various skin types.

TABLE I

| Skin Type | S1 | S2 | S2 | S4 | S5 |
| --- | --- | --- | --- | --- | --- |
| Light | .25 | .5 | 1 | 2 | 4 |
| Medium | .5 | 1 | 2 | 4 | 8 |
| Dark | 1 | 2 | 4 | 8 | 16 |

The times (durations) provided in Table I are in units of hours and are times for the various segments of the LCD panel to activate in the presence of medium-to-light radiation (e.g., UV index (UVI) of about 3). It should be noted that if the radiation present were greater than medium-to-light, then these times in Table I would be shorter. Likewise, if the radiation present were less than medium-to-light, then these times in Table I would be longer.

Figure 15A:
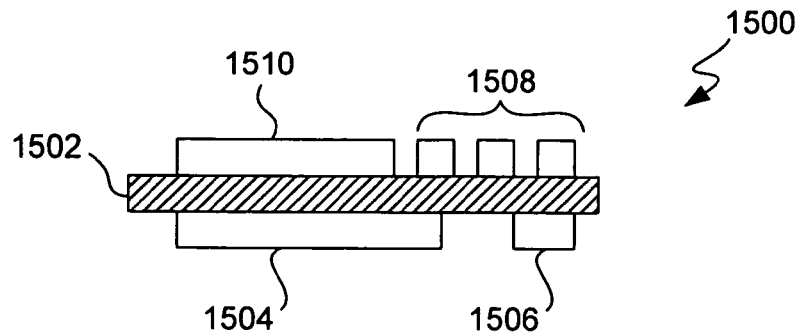
FIGS. 15A-15C are cross-sectional diagrams of a radiation detection systems according to different embodiments of the invention.
Figure 15B:
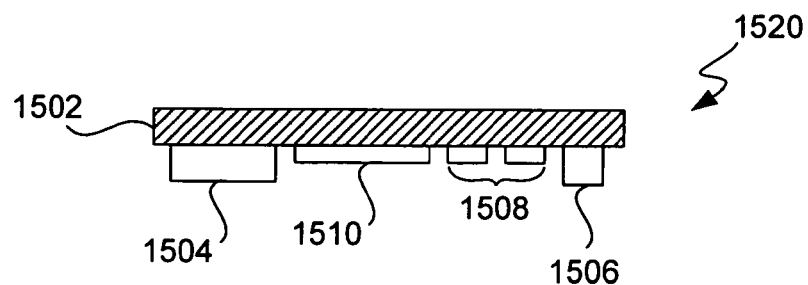
Figure 15C:
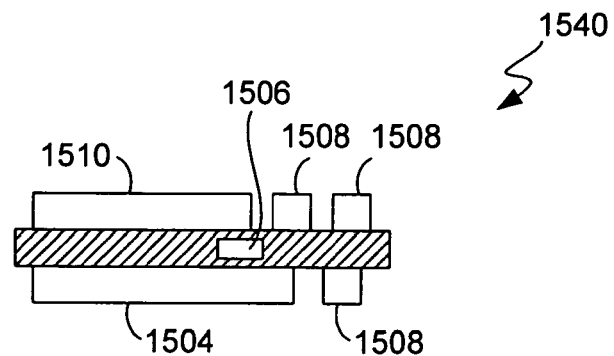

FIGS. 15A, 15B and 15C are radiation detection systems according to different embodiments of the invention. These radiation detection systems are described in the context of UV radiation detection (which uses a UV sensor); however, it should be understood that these radiation detection systems can be also be used to detect other types of radiation. This can be accomplished, for example, by replacing the UV sensor in the radiation detection system with another type of sensor, such as an infrared sensor or light sensor. These UV detection systems are compact modular systems. The UV detection systems can be built on a single substrate that is designed to be inserted into an end product. Since the UV detection system is compact and modular, the end product need only have an opening, cavity or container to hold or encompass the UV detection system. As such, the end product can quickly be transformed into an end product capable of providing UV monitoring. Advantageously, in one embodiment, the UV detection system is such that has minimal impact on design of the end product and no tedious wiring is required. For example, in case in which the end product is an eyeglass frame, a temple of the eyeglass frame can have an opening, cavity or container to hold or encompass the UV detection system, whereby no other changes or complications to the eyeglass frames need be imposed. Other such end-products can include: hats, shoes, tee-shirts, swimming-suits, key rings, purses, beverage can holders, and other consumer products.

FIG. 15A is a cross-sectional diagram of a UV detection system 1500 according to one embodiment of the invention. The UV detection system 1500 is build on a substrate 1502. The substrate 1502 can be a printed circuit board, a flexible tape or film (e.g., Kapton® polyimide film), ceramic, and the like, as known in the art. The UV detection system 1500 includes a power source 1504, an UV sensor 1506, electrical circuitry 1508 and a display device 1510 (e.g., LCD or LED). The display device 1510 is one type of output device, so it should be recognized that other embodiments can utilize other types of output devices. The power source 1504 is, for example, a battery or a solar panel of one or more solar cells. For example, if the power source 1504 is a battery, the battery can be a coin battery, such as often used in electronic watches. In one embodiment, the UV sensor 1506 includes a phototransistor. In one embodiment, the electrical circuitry 1508 includes one or more of analog electrical components (e.g., capacitors, resistors, diodes, transistors) or integrated circuits. Any such integrated circuits can be provided in a variety of packages, but surface mount packages can help maintain a thin profile for the UV detection system 1500. The various electrical components can be wire bonded onto the substrate 1502. For example, a SiC or GaN phototransistor (or photodiode) can serve as at least part of a UV sensor and be wire bonded onto the substrate 1502 or other electrical component. The UV detection system 1500 shows components of the system mounted to both sides of the substrate 1502.

FIG. 15B is a cross-sectional diagram of a UV detection system 1520 according to another embodiment of the invention. The UV detection system 1520 can utilize the same or similar components as the UV detection system 1500. However, unlike the UV detection system 1500, the UV detection system 1520 mounts all components on one side of the substrate 1502. The effect of the UV detection system 1520 is a thinner module, though the substrate 1502 may be longer, as compared to the UV detection system 1500 shown in FIG. 15A.

FIG. 15C is a cross-sectional diagram of a UV detection system 1540 according to another embodiment of the invention. The UV detection system 1540 can utilize the same or similar components as the UV detection system 1500. However, unlike the UV detection system 1500, the UV detection system 1540 mounts the UV sensor 1506 at or near the edge of the substrate 1502. This has the potential advantage of positioning the UV sensor 1506 in a position so that it is better able to receive incident radiation (e.g., sunlight). The mounting of the UV sensor 1506 with respect to the substrate 1502 can also be flexible so that the UV sensor 1506 can be positioned, such as angularly positioned with respect to the substrate 1502 and/or angularly oriented when assembled into an opening, cavity or container of an end-use product. For example, the UV sensor 1506 could be soldered onto the substrate 1502 tipped at an angle. Alternatively, a small prism could be mounted on top of the UV sensor 1506, providing an angled direction of sensitivity. For example, the prism could be formed in place by filling a small, angled, box with clear optical adhesive (such as epoxy) that, when set would provide a prism, efficiently-coupled to the UV sensor 1506.

The UV sensor 1506 utilized in the UV detection systems 1500, 1520 and 1540 may use an optical filter with an optical sensor. For example, the optical sensor can respond to light, UV and infrared radiations, and the sensitivity of the optical filter causes the optical sensor to capture primarily the target radiation (e.g., UV) wavelengths of light. Hence, the UV sensor 1506 can include such optical filter. For example, the optical filter can be implemented as a coating on the optical filter. Alternatively, the optical filter can also be a separate component that is positioned proximate to the optical sensor when the end product is assembled. In other words, an optical filter can be another component of the UV detection system, or can be a separate component that is inserted when assembled into the end product. In one embodiment, an optical adhesive can be used to secure the optical filter to the optical sensor.

Figure 16A:
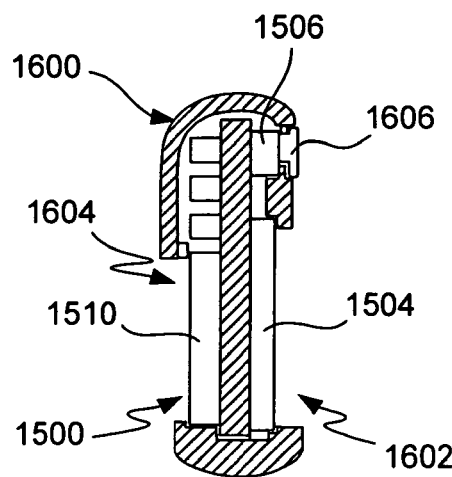
FIG. 16A is a cross-sectional view of an eyewear housing containing a radiation detection system according to one embodiment of the invention.

FIG. 16A is a cross-sectional view of an eyewear housing 1600 containing a UV detection system according to one embodiment of the invention. Here, the eyewear housing 1600 can represent a portion of the temple region of a frame for a pair of glasses. Typically, the portion of the temple region is forward of the user's ear (i.e., towards the lens holders) when the glasses are being worn. The UV detection system contained within the eyewear housing 1600 is, for example, the UV detection system 1500 shown in FIG. 15A. The eyewear housing 1600 has an opening, cavity or container to receive the UV detection system. The eyewear housing 1600 also has a first opening 1602 and a second opening 1604. The first opening 1602 is aligned with the power supply 1504, which would in such an embodiment be a solar panel. Hence, the first opening 1602 can allow light to impinge on the solar panel. The second opening 1604 is aligned with the display device 1510 so that information displayed can be seen. The eyewear housing 1600 also includes an optical filter 1606 that is positioned proximate to the UV sensor 1506. In one embodiment, the optical filter 1606 is a separate component that inserted into an opening in the eyewear housing 1600 that is proximate (e.g., adjacent) to the UV sensor 1506. In another embodiment, the optical filter 1606 is integral with the UV sensor 1506.

Figure 16B:
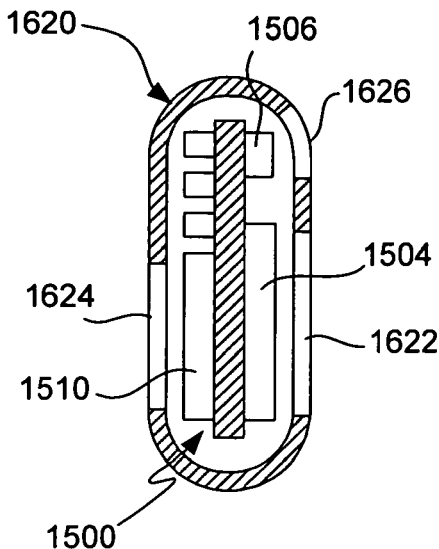
FIG. 16B is a cross-sectional view of an eyewear housing containing a radiation detection system according to another embodiment of the invention.

FIG. 16B is a cross-sectional view of an eyewear housing 1620 containing a UV detection system according to another embodiment of the invention. The eyewear housing 1620 has an opening, cavity or container to receive the UV detection system, such as the UV detection system 1500 shown in FIG. 15A. The eyewear housing 1620 also has a first window 1622 and a second window 1624. The first window 1622 is aligned with the power supply 1504, which would in such an embodiment be a solar panel. Hence, the first window 1622 can allow light to impinge on the solar panel. The second window 1624 is aligned with the display device 1510 so that information displayed can be seen. The eyewear housing 1600 also includes a third window 1626. The third window 1626 is positioned proximate to the UV sensor 1506. The third window 1626 can, in one embodiment, operate as an optical filter for the UV sensor 1506. The first and second windows 1622 and 1624 can be clear or colored so long as adequate light passes through.

Figure 16C:
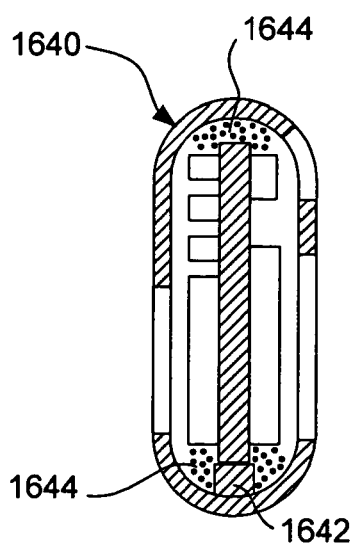
FIG. 16C is a cross-sectional view of an eyewear housing containing a radiation detection system according to still another embodiment of the invention.

FIG. 16C is a cross-sectional view of an eyewear housing 1640 containing a UV detection system according to still another embodiment of the invention. The eyewear housing 1640 is generally similar to the eyewear housing 1620 illustrated in FIG. 16B. However, FIG. 16C illustrates one way to secure the UV detection system within the portion of the temple region of the eyewear housing 1640. In particular, the eyewear housing 1640 include a stand 1642 and an adhesive material 1644. When assembled, the UV detection system can be placed within the temple region of the eyewear housing 1640 and positioned against the stand 1642, then the adhesive 1644 can be provided within the temple region to secure the UV detection system in position. The adhesive can vary widely, such as glue, double-stick tape, silicone rubber, epoxy, etc.

Figure 16D:
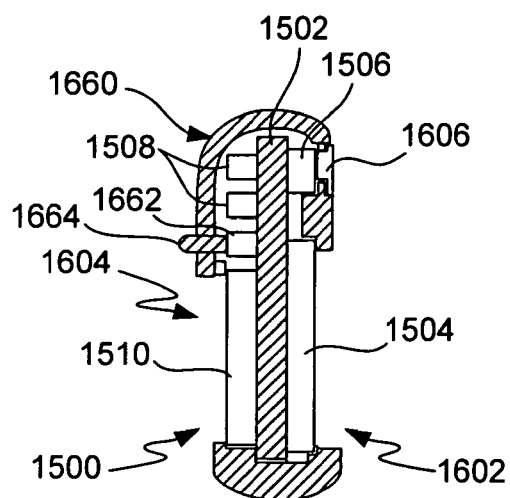
FIG. 16D is a cross-sectional view of an eyewear housing containing a UV detection system according to yet still embodiment of the invention.

FIG. 16D is a cross-sectional view of an eyewear housing 1660 containing a UV detection system according to yet still embodiment of the invention. The eyewear housing 1660 is generally similar to the eyewear housing 1600 illustrated in FIG. 16A, except that the electrical circuitry 1508 may be repositioned on the substrate 1502 and a switch base 1662 and a switch 1664, such as a button switch, are provided. As shown in FIG. 16D, the switch base 1662 can attach to the substrate 1502 and thereby support the switch 1664 that protrudes outside of the eyewear housing 1660 (or is otherwise accessible) so that a user can activate the switch (e.g., press the button).

Figure 16E:
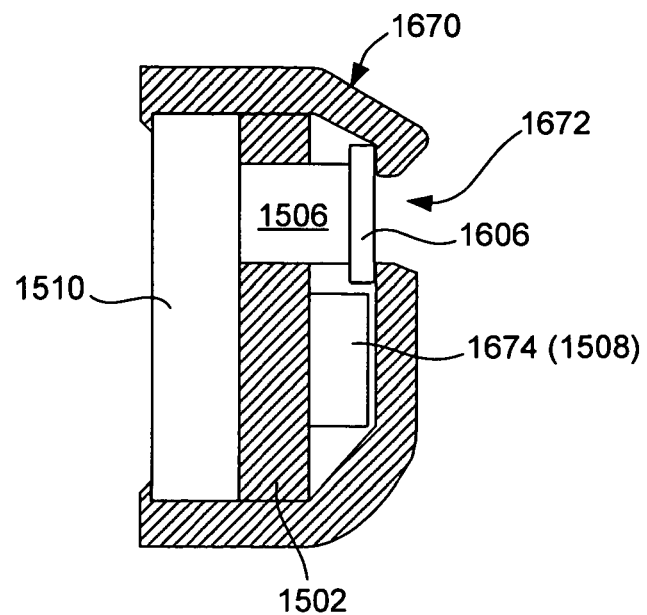
FIG. 16E is a cross-sectional view of an eyewear housing containing a radiation monitoring system according to one embodiment of the invention.

FIG. 16E is a cross-sectional view of an eyewear housing 1670 containing a radiation monitoring system according to one embodiment of the invention. The eyewear housing 1670 includes a substrate 1502, such as a printed circuit board. The UV sensor 1506, more generally a radiation sensor, can be placed in an opening or indentation of the substrate 1502, or on the substrate 1502. The optical filter 1606 is provided proximate to the radiation sensor which is also adjacent to an opening 1672 in the eyewear housing 1670. As an example, the eyewear housing 1670 can correspond to a temple of a pair of eyeglasses. The electrical circuitry 1508 can also be attached to the substrate 1502. In this embodiment, the electrical circuitry 1508 includes an integrated circuit chip 1674 that is attached or bonded to a first side of the substrate 1502 (e.g., printed circuit board). As an example, the integrated circuit chip 1674 can be a microcontroller, such as the microcontroller 4402 illustrated in FIG. 14R. The display device 1510 can be attached to a second side of the substrate. For example, the display device 1510 can be a LCD panel. Optionally, the opening 1672 can contain an optical element, such as a lens, to focus radiation onto the radiation sensor, thereby broadening sensitivity to the angle of incident radiation. broadening angle sensitivity. The optical element may also service as a radiation attenuator and/or an optical filter. For example, a tinted diffuser dome can act as a lens and an attenuator. Hence, if such an optical element is used, the optical element may obviate the need for the separate optical filter 1606. More generally, the optical filter 1606 may not be necessary when the sensitivity of the radiation sensor is adequate to limit the measurement to the desired radiation. Although not shown in FIG. 16E, the radiation monitoring system could also typically include a power source, such as a battery or solar cell, one or more switches, and additional electrical circuitry 1508 (e.g., capacitor) besides the integrated circuit chip 1674.

In general, the UV detection system according to the invention can make use of zero or more switches. One type of switch is a button switch, such as a push-button switch. As an example, the switch can serve as a reset switch, an on/off switch, or an on (and reset) switch.

Figure 17A:
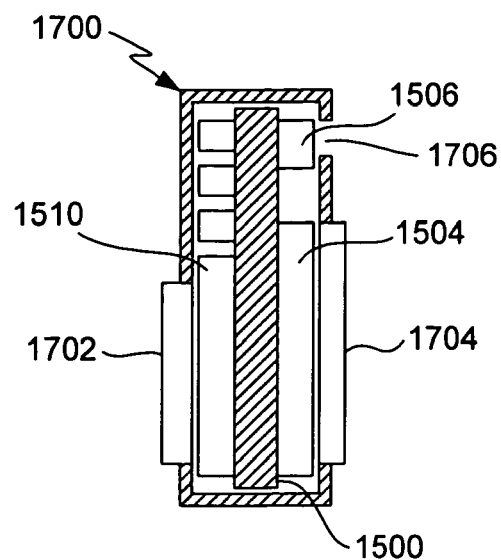
FIG. 17A is a cross-sectional view of a module housing according to one embodiment of the invention.

FIG. 17A is a cross-sectional view of a module housing 1700 according to one embodiment of the invention. As shown in FIG. 17A, the module housing 1700 can operate as a housing for the UV detection system 1500 shown in FIG. 15A. The module housing 1700 includes a first window 1702 and a second window 1704. The first window 1702 can be proximate to the display device 1510, and the second window 1704 can be proximate to the power supply 1504, which would in such an embodiment be a solar panel. The first and second windows 1702 and 1704 can be clear or colored so long as adequate light passes through. In one embodiment, the thickness of the first and second windows 1702 and 1704 is greater than the thickness of the walls of the module housing 1700. The module housing 1700 can also include an opening 1706 that is positioned proximate to the UV sensor 1506. Still further, although not illustrated in FIG. 17A, the module housing 1700 can further include one or more vents or holes so that air can circulate through the module housing 1700. Alternatively, the module housing 1700 does not include vents or holes, so as to be water-resistant or water-proof.

The module housing 1700 is a housing for a module, such as a UV detection system. The module housing 1700 is then placed into an opening, cavity or container of an eyewear housing, such as a temple region of the eyewear housing. The module housing 1700 protects the module. The module housing 1700 can also be used to regularize or standardize the form factor for the UV detection system, such that the opening, cavity or container of the eyewear housing can be regularized or standardized.

Figure 17B:
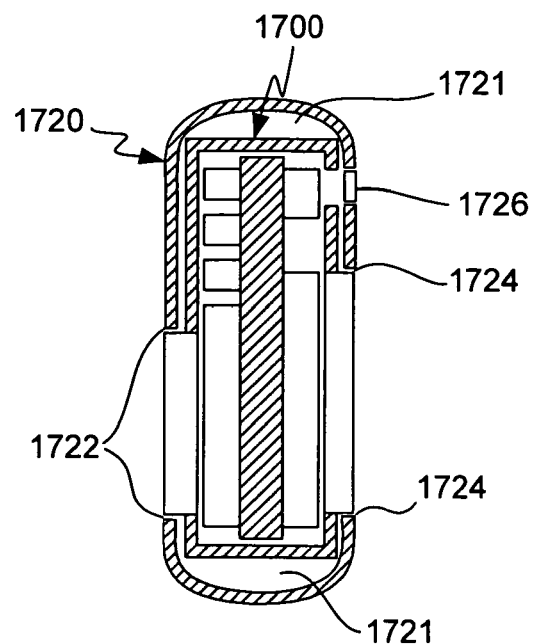
FIG. 17B is a cross-sectional view of an eyewear housing according to one embodiment of the invention.

FIG. 17B is a cross-sectional view of an eyewear housing 1720 according to one embodiment of the invention. The eyewear housing 1720 has an opening, cavity or container 1721 for receiving the module housing 1700. As shown in FIG. 17B, the module housing 1700 is contained by the eyewear housing 1720. The eyewear housing 1720 includes an opening 1722 that corresponds to the first window 1702 of the module housing 1700. The eyewear housing 1720 also includes an opening 1724 that corresponds to the second window 1704 of the module housing 1700. Still further, the eyewear housing 1720 can optionally further include an optical filter 1726 corresponding to the third opening 1706 of the module housing 1700 (and thus proximate to the UV sensor 1506). The module housing 1700 can, for example, be held in position with respect to the eyewear housing 1720 by an adhesive or by an interference fit.

Figure 18:
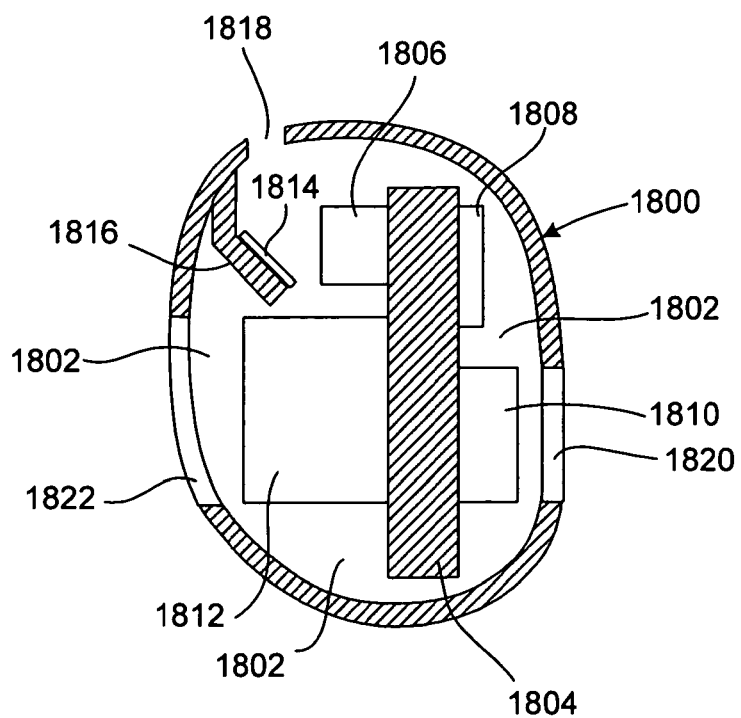
FIG. 18 is a cross-sectional view of an eyewear housing having a reflective-type filter according to one embodiment of the invention.

FIG. 18 is a cross-sectional view of an eyewear housing 1800 having a reflective-type filter according to one embodiment of the invention. Here, the eyewear housing 1800 can represent a temple region of a frame for a pair of glasses. Typically, a large percentage of the temple region is in front of the user's ear when the glasses are being worn. The eyewear housing 1800 has an internal cavity 1802 where a circuit board 1804 is provided. Electrically coupled to the circuit board 1804 are a UV detector 1806 (e.g., based on a photodetector), electrical circuitry 1808, a display device (e.g., LED, LCD) 1810, and solar cell(s) 1812. As a result, the circuit board 1804 and the UV detector 1806, the electrical circuitry 1808, the display device 1810 and the solar cell(s) 1812 are within the internal cavity 1802 and thus embedded within the eyewear housing 1800.

A UV reflector 1814 is mounted on an internal support 1816. Light impinges on the UV reflector 1814 via an opening 1818 in the eyewear housing 1800. The opening 1818 allows radiation to pass through to the UV reflector 1814. In one embodiment, there can be a piece of transparent material at the opening 1818 to prevent dust or dirt from getting through the opening 1818 into the internal cavity 1802. The opening 1818 can also be considered a transparent region in the eyewear housing 1800. The UV reflector 1814 selectively reflects primarily the UV portion of the radiation towards the UV detector 1806. As a result, the reflector 1814 serves as a reflective-type filter, that is, a type of optical filter. For example, the reflector 1814 can be made of a material that substantially reflects UV light but does not reflect non-UV light. An example of one such reflector is known as a UV hot mirror. Also, the eyewear housing 1800 can also include transparent portions 1820 and 1822 which are adjacent to the display device 1810 and the solar cell(s) 1822, respectively. The transparent portion 1820 allows light from the display device 1810 to be seen from the outside of the eyewear housing 1800. The transparent portion 1822 allows light from an external light source to impinge on the solar cell(s) 1812. Alternatively, the display device 1810 could extend to and conform with an outer surface of part of the eyewear housing 1800, and the solar cell(s) 1812 could extend to and confirm with an outer surface of part of the eyewear housing 1800. Alternatively, if a battery were used in place of the solar cell(s) 1822, then the transparent portion 1822 would not be needed.

In one embodiment, a number of previously described transparent regions, portions, or sheets of materials, such as the transparent portions 1820 and 1822 in FIG. 18, can be translucent (including partially translucent). Still another alternative is that the eyewear housing 1800 could be primarily translucent.

The optical sensor or UV sensor can receive impinging light from a variety of different directions (i.e., angle of incidence) depending on implementation. For example, the light can come from an opening in the top of the temple, such as shown in FIG. 18, or at a side of the temple, such as shown in FIGS. 16A-16C and 17B. As another example, the light can come from an opening at an angle between the top and the side of the temple. Typically, the optical sensor or the UV detector would be aligned with the opening at whatever angle it takes, such alignment tends to maximize sensitivity of the optical sensor or the UV detector. The optimal angle can also be based on the latitude. Thus, at the equator, the UV detector should point upward. And at the north pole, the sensor should point horizontally. In one embodiment, the size of the opening can be larger to increase impinging light, or can be smaller to decrease impinging light. In another embodiment, the opening can be flared outward so as to increase the amount of impinging light. Further, the opening can also support a lens for focusing impinging light.

The UV detection system can also have a "being-worn" switch as noted above. In one embodiment, the "being-worn" switch enables the UV monitoring system to automatically determine when to monitor UV radiation and when not to monitor UV radiation. In particular, the UV radiation can be monitored when an eyeglass frame having the UV detection system is "being-worn" and not when the eyeglass frame is not "being-worn." The "being-worn" switch can be positioned in the temple portion with the other components of the UV detection system. In one embodiment, the UV detection system is provided, as a module as noted above, and which further includes a switch. The switch can, for example, be a "being worn" switch. By having the switch in the module, the manufacture and assembly of the end-product having the UV detection system can be simplified. As examples, the "being-worn" switch can be an optical, magnetic or mechanical switching device.

The "being-worn" switch can make use of the situation that the temples are in an open position when the eyeglass frame is being worn, and in a closed position when not being worn. In one embodiment, the "being-worn" switch can be positioned at a temple proximate to a region that couples the temple to its corresponding lens holder. For example, the UV detection system (e.g., module) can be provided within the temple region near the end of the temple so that the "being worn" switch is adjacent the lens portion of the eyeglass frame.

Figure 19:
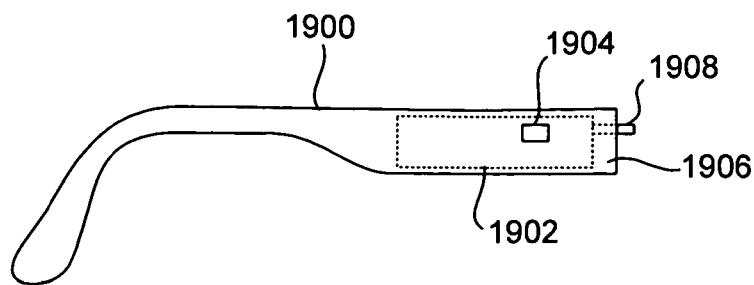
FIG. 19 is a side view of a temple for an eyeglass frame according to one embodiment of the invention.

FIG. 19 is a side view of a temple 1900 for an eyeglass frame according to one embodiment of the invention. The side view of FIG. 19 shows an outer side of the temple 1900, namely, the side of the temple 1900 that faces outward when being worn. The temple 1900 includes therein a UV detection system 1902 internal to the temple 1900. A window 1904 is provided in the temple 1900 for light (e.g., sunlight) to impinge on a UV sensor of the UV detection system 1902. The window 1904 can also provide some optical filtering effects, such as noted above. Although not shown in FIG. 19, the temple 1900 may also have a window or opening for a solar panel. At a forward end 1906 of the temple 1900 where a hinge is typically provided, a pin 1908 is exposed. The pin 1908 passes through an opening at the forward end 1906 of the temple 1900. The pin 1908 is coupled to a switch internal to the temple 1900 and part of the UV detection system 1902. When the pin 1908 is not depressed, as shown in FIG. 19, the switch informs the UV detection system 1902 that the eyeglass frame is closed, i.e., not being worn. On the other hand, when the eyeglass frame is opened, i.e., presumably being worn, the pin 1908 is depressed by the forward end 1906 abutting against a portion of its corresponding lens holder, thereby informing the UV detection system 1902 that the eyeglass frame is opened. In one embodiment, the pin 1908 is only depressed when the temple 1900 of the eyeglass frame is fully opened, such that the eyeglass frame would almost necessarily be worn (particularly when there is a bias against the eyeglass frame being fully open).

Figure 20A:
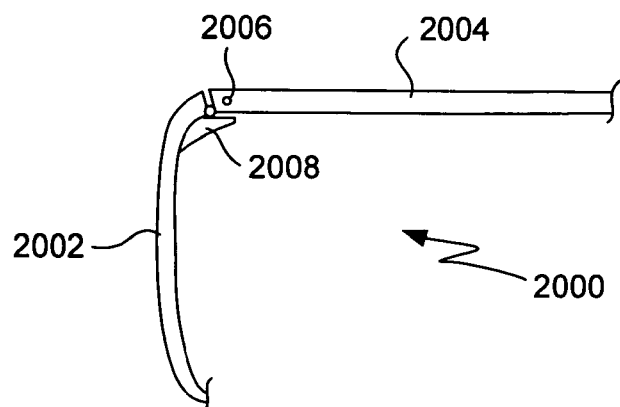
FIGS. 20A and 20B are top view diagrams of a portion of an eyeglass frame according to one embodiment of the invention.
Figure 20B:
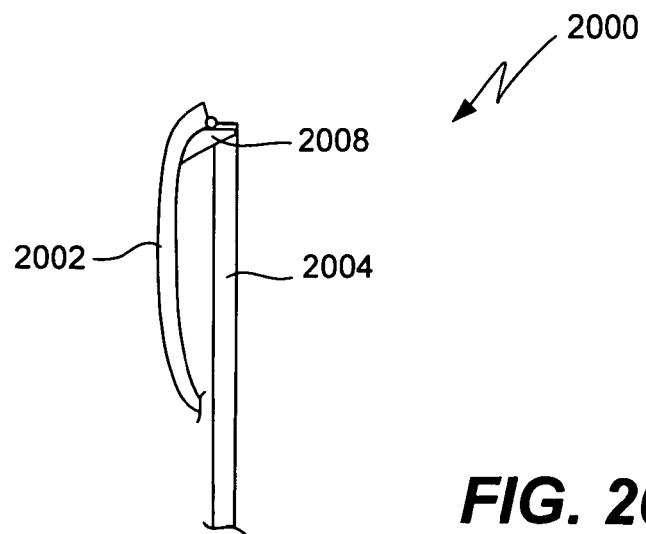

FIGS. 20A and 20B are top view diagrams of a portion of an eyeglass frame 2000 according to one embodiment of the invention. The eyeglass frame 2000 includes a lens holder 2002 and a temple 2004. The temple 2004 includes a UV detection system therein. The UV detection system includes an opening or window 2006 that corresponds to an optical sensor used by the UV detection system. The optical sensor is used as a "being-worn" switch. When the eyeglass frame 2000 is in the open position as shown in FIG. 20A, the optical sensor detects significant light, thereby informing the UV detection system that the eyeglass frame 2000 is presumably being worn. On the other hand, when the eyeglass frame 2000 is in the closed position as shown in FIG. 20B, the opening or window 2006 is covered by a flap 2008 provided on the lens holder 2002. When the flap 2008 covers the opening or window 2006, no significant light can be detected by the optical sensor. In such case, the UV detection system is informed that the eyeglass frame 2000 is not being worn.

Figure 21:
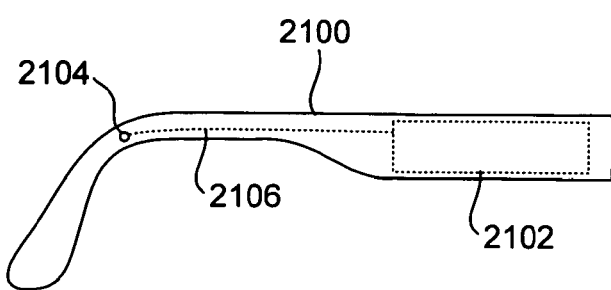
FIG. 21 is a side view of a temple for an eyeglass frame according to one embodiment of the invention.

FIG. 21 is a side view of a temple 2100 for an eyeglass frame according to one embodiment of the invention. The side view of FIG. 21 shows an inner side of the temple 2100, namely, the side of the temple 2100 that faces inward when being worn. The temple 2100 includes therein a UV detection system 2102 internal to the temple 2100. The temple 2100 may also have a window or opening (not shown) that corresponds to an output device (e.g., display). A window or opening 2104 is provided at a rearward portion of the temple 2100. The window or opening 2104 corresponds to an optical sensor (internal to the temple 2100) provided at the window or opening 2104. The window or opening 2104 allows light (e.g., sunlight) to impinge on the optical sensor. The optical sensor is coupled to the UV detection system 2102 via one or more electrical wires 2106. When the temple 2100 of the eyeglass frame is being worn by a user, the optical sensor will be blocked from receiving significant amounts of light, thereby informing the UV detection system 2102 that the eyeglass frame is being worn. For example, the optical sensor can be blocked by the user's head or hair when the eyeglass frame is being worn. On the other hand, when the temple 2100 of the eyeglass frame is not being worn by a user, the optical sensor will receive significant amounts of light, thereby informing the UV detection system 2102 that the eyeglass frame is not being worn. Of course, at night often little or no light will impinge on the optical sensor. Optionally, in such case the lack of any significant light (e.g., detected by another optical sensor or solar cell) can be used to ensure that the UV detection system does not operate at night, such that the eyeglass frame can be considered not being worn at night (even if being worn at night).

Figure 22:
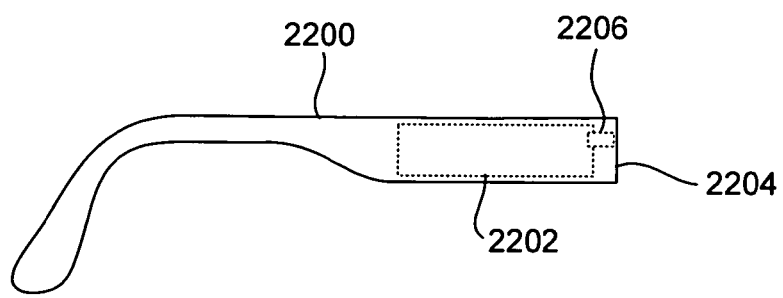
FIG. 22 is a side view of a temple for an eyeglass frame according to another embodiment of the invention.

FIG. 22 is a side view of a temple 2200 for an eyeglass frame according to another embodiment of the invention. The side view of FIG. 22 shows an outer side of the temple 2200, namely, the side of the temple 2200 that faces outward when being worn. The temple 2200 includes therein a UV detection system 2202 internal to the temple 2200. Although not shown in FIG. 22, the temple 2200 may also have windows or openings for a solar panel and/or an optical sensor. At a forward end 2204 of the temple 2200, a magnetic switch 2206 is provided. The magnetic switch 2206 is internal to the temple 2200 and part of the UV detection system 2202. The magnetic switch 2206 can use a magnet to provide a switch. The magnetic switch 2206 switches from a first position to a second position when a metallic material is adjacent the forward end 2204 of the temple 2200. For example, such metallic material can be provided in a portion of a lens holder that abuts the forward end 2204 when the temple 2200 is in the open position. Here, when the switch is in the open position, the metallic material is adjacent the forward end 2204 of the temple 2200, and the UV detection system 1902 understands that the eyeglass frame is opened, i.e., presumably being worn. In such case, the switch can be considered to be in the second position. On the other hand, when the eyeglass frame is closed, i.e., not being worn, the switch is in the first position because the metallic material is no longer adjacent the forward end 2204 of the temple 2200. Then, the UV detection system 2202 understands that the eyeglass frame is closed (i.e., not being worn). In one embodiment, the magnetic switch 2206 can be implemented by a Hall effect sensor. Alternatively, it should be understood that the magnetic switch could be provided at a portion of a lens holder that abuts the forward end 2204 when the eyeglass frame has the temple 2200 open, and the metallic material could be at the forward end 2204.

The "being worn" switch can also be used by a user to signal the UV detection system to provide its output at an output device, such as a display device. For example, when the "being worn" switch is initially closed (i.e., being worn), the UV detection system can output its text or graphical output to the display device. Typically, the displayed output would be displayed only for a limited period of time (e.g., 10 seconds). Such an approach is power efficient, yet permits the user to obtain the output information when desired. Alternatively, another switch (e.g., dedicated output switch) could be used to cause the output to be displayed for a limited period of time or while the switch is depressed.

The UV detection system can also make use of one or more switches to change operational settings, such as threshold levels, output type, user preferences, user physical characteristics (e.g., skin type), accumulation mode or non-accumulation mode, activation/deactivation of auxiliary sensors.

The UV detection system can make use of one or more variable capacitors or resistors within the design of the electronic circuit to facilitate a manufacturer or dispenser to calibrate the UV detection. Such can assist with quality control as well as consistency or uniformity. The UV detection system can also alter another aspect of the electronic circuitry, such as a count or divide amount (FIG. 14B), to calibrate the UV detection.

Calibration or customization of the UV detection system can also be performed after manufacturer by a user or dispenser. As one example, the eyewear can be sold or dispensed with one or more stickers available for placement over the radiation detector (e.g., UV sensor). The stickers can attenuate the radiation impinging on the radiation detector. In other words, the stickers can perform sensitivity adjustment on the UV detection system. Different ones of the stickers can offer different degrees of attenuation. A user can thus select an appropriate sticker based on their skin type (or amount of exposure they prefer) and place it over the radiation detector, thereby calibrating or customizing the UV detection system to the user.

As previously noted, the optical sensor (e.g., UV sensor) can be implemented by at least one photodetector, such as a phototransistor. Although various different phototransistors can be utilized, one example of a suitable phototransistor is Part No. PT100MCOMP available from Sharp Microelectronics of the Americas. As another example, a suitable phototransistor for the phototransistor is Part No. EL-PT15-21B (1206 phototransistor) available from Everlight Electronics Co., Ltd. As still another example, other suitable phototransistors are GaN or SiC phototransistors. Alternatively, although the discussion above at times refers to phototransistors, the photodetector can also be a photodiode. In the case of a photodiode, similar circuitry to that noted above would be utilized. Although various different photodiodes can be utilized, one example of a suitable photodiode is Part No. PD100MCOMP available from Sharp Microelectronics of the Americas.

The radiation sensors or detectors, including phototransistors and photodiodes, used for radiation monitoring are often designed for sensing or detecting certain types of radiation. For example, a UV sensor or UV detector would be an electronic device that is sensitive to UV radiation, namely, the wavelengths of light pertaining to UV spectrum. While such electronic device may be primarily sensitive to such radiation of interest (e.g., UV radiation), they may also be somewhat sensitive to other radiation. Optical filters can be used to assist these sensors or detectors in sensing the desired type of radiation. Nevertheless, radiation monitoring can be achieved even though the radiation sensors or detectors are sensitive to non-desired radiation so long as they are primarily or principally responsive to the desired radiation.

When the radiation to be monitored is UV radiation, the optical filter described above is typically implemented by a material that passes radiation in the UV wavelength band and blocks radiation not in the UV wavelength band. Various materials can be used in this regard. In one embodiment, the material providing the optical filtering can be known as a UV cold mirror. However, in another embodiment, the optical filter may have other characteristics, such as a material (e.g., polycarbonate) that passes radiation not in the UV wavelength band and blocks radiation in the UV wavelength band. In another embodiment, the optical filter can utilize a material that passes light primarily associated with the ultraviolet wavelength range while substantially blocking light of other wavelengths. Such a material can, for example, be a filter made from quartz-glass with nickel oxide, such is commonly known as Wood's glass. The material implementing the optical filter can also be configured in various ways, such as a plug for an opening or a coating on a surface (or on the photodetector itself). In one embodiment, the material implementing the optical filter can either pass or reflect the UV radiation.

An output (e.g., notification, such as a warning) to the user can vary in content and type. The type can be visual and/or audio. The content can be numerical, graphical, musical, textual, synthesized text, etc. A progression of warnings can be used to give more substantial warning (such as when prior warnings are ignored). The output can also be predetermined, dynamically determined or configurable. Still further, the output can be dependent on user preferences, user physical characteristics (e.g., skin type), auxiliary sensor information (e.g., location), and degree of health risk.

The radiation monitoring system can also include one or more connectors with the eyewear. The connectors can, for example, facilitate electrical or mechanical interconnection with an external electrical device (e.g., computing device, media player, headset, power source). Although the format and size of the connectors can vary, in one embodiment, the connector is a standard audio connector or a peripheral bus connector (e.g., USB connector).

The radiation monitoring system can also include one or more switches with the eyewear. The switches can, for example, facilitate user input or control with respect to the radiation monitoring system. For example, the switches can provide one or more of on/off, reset, on, on (and reset), and calibration. One example of a calibration switch is a skin type switch that provides switch positions for different skin types (e.g., light, medium and dark). The radiation monitoring system can also provide a user with an indication of whether the system is currently on or off, such as by a graphical image on a display device or by a LED.

A radiation monitoring system can also include a memory. The memory can be volatile or non-volatile. The memory can also be removable or non-removable with respect to the eyewear. If the memory is volatile, the radiation monitoring system could include a battery to provide power to the memory so that stored data (e.g., accumulated radiation, user preferences, etc.) can be retained even when adequate solar energy is not available. As an example, the presence of a memory can allow storage of radiation information for an extended period of time to acquire a historical understanding of radiation information.

In one embodiment, an eyeglass frame can include memory that can store acquired radiation information, such stored radiation information can be subsequently uploaded to a computer, in a wired or wireless manner. The radiation information can then be analyzed by the computer. For example, a doctor may require a patient to keep track of his exposure to UV radiation, or other radiations, to assist the doctor to evaluate risks or symptoms.

In another embodiment, a user of an eyeglass frame interact with a switch provided on the eyeglass frame to set a calibration level. As an example, in the case of UV radiation, the calibration level can correspond to the user's skin type. In general, the calibration level causes the amount of acceptable radiation (e.g., threshold levels) to vary.

In still another embodiment, a user can go through a calibration procedure when the user purchases the eyeglasses. The calibration procedure can operate to personalizes the UV detection system for the user. For example, the complexion of the user's skin affects the user's sensitivity to UV. Based on the skin complexion, a UV monitoring system adjusts the levels of acceptable exposure to UV. The calibration procedure can be performed wired or wirelessly. For example, the calibration can be done by a computer, with the calibration data downloaded to the eyeglasses through a connector integral with the eyeglasses.

A radiation monitoring system can also include a communication module. The communication module would allow data transmission to and from the radiation monitoring system (namely, the eyewear) and an external device. The data being transmitted can, for example, be radiation information, configuration data, user preferences, or auxiliary sensor data. The data transmission can be wireless or wireline based. The eyewear can further include a connector operatively connected to the radiation monitoring system. Such a connector can facilitate data transmission with respect to the radiation monitoring system or the eyewear.

A temple of a pair of glasses can be removable of the remainder of the frame. Such facilitates replacement of temples. For example, a convention temple could be removed from a frame and replaced with a temple having a least one electrical component at least partially embedded therein.

A radiation monitoring system can be partially or fully contained in a temple arrangement associated with a temple of a pair of glasses. In one embodiment, the temple arrangement can be removable from the temple. A temple arrangement can be a temple tip, a temple cover or a temple fit-over.

A radiation monitoring system can be partially or fully tethered to a pair of glasses. For example, some of the components for monitoring radiation or one or more auxiliary sensors can be tethered to the eyewear. In one embodiment, the tethered components can be tethered at the neck or upper back region of the user. Tethering components allows for increased design freedom with the eyewear as well as additional area with which to house the components.

Still further, a radiation monitoring system could be partially or completely within a device or a base that can be tethered to eyewear.

A number of embodiments have been described above for an eyeglass frame, i.e., primary frame. Such embodiments are also applicable to an auxiliary frame. An auxiliary frame can attach to a primary frame through different techniques, such as using clips. Another technique to attach an auxiliary frame to a primary frame is by way of magnets. Examples of using magnets as an attachment technique can be found, for example, in U.S. Pat. No. 6,012,811, entitled, "EYEGLASS FRAMES WITH MAGNETS AT BRIDGES FOR ATTACHMENT."

Although much of the discussion above concentrates on UV monitoring, the invention is generally applicable to radiation monitoring. The radiation can, for example, pertain to one or more of UV, infrared, light and gamma radiation. Light, namely visible light, can be referred to as ambient light.

Also, the above discussion concerning UV sensor or UV monitor is generally applicable to radiation sensors or monitors. One embodiment of a radiation sensor or monitor which principally measures light is a light sensor or a light monitor. More particularly, in measuring light, sunlight is a dominant source of light, such that a radiation sensor or monitor which principally measures light can be referred to as a sun sensor or a sun monitor. In such case, radiation monitoring can be considered light monitoring or sunlight monitoring.

Visible light is part of everyday life and is generally not considered harmful to persons. In one embodiment, the measurement of light can be used to infer a measurement of harmful radiation (e.g., UV radiation).

A number of embodiments have been described where a radiation monitoring system is embedded in a temple of an eyeglass frame. However, in other embodiments, the radiation monitoring system can be in other parts of the eyeglass frame, such as the bridge or lens holder region. Also, for eyewear having shield(s) or wrap-around lenses, the radiation monitoring system can also be in such shield(s) or lenses.

Although much of the above discussion pertains to providing radiation (e.g., radiation) monitoring capabilities in eyewear, it should be understood the any of the various embodiment, implementations, features or aspects noted above can also be utilized is other or on end products besides eyewear. Examples of other such end-products can include: hats (e.g., soft hats, hard-hats, helmets), watches or watch bands, bracelets, bracelet accessories, necklaces, necklace accessories, rings, shoes (e.g., sandals, athletic shoes, beach shoes), shoe accessories, clothing (e.g., tee-shirt, swimming-suit, ties, pants, jackets, etc.), belts, belt accessories, zippers, key rings, purses, beach-tags, containers (e.g., cups, bottle, tube—such as a sun tan lotion bottle or tube); container holders (e.g., can holders, coasters, coolers, etc.), and other consumer products.

Figure 23A:
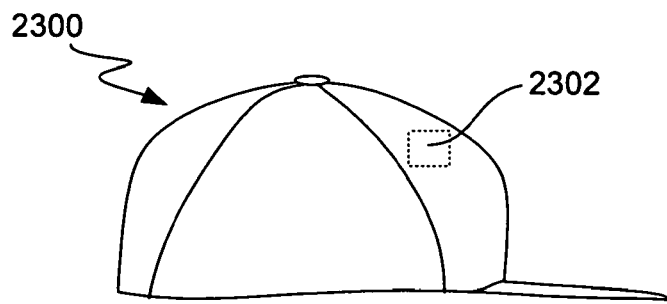
FIGS. 23A-23G illustrate examples of various end products having radiation monitoring capability.
Figure 23B:
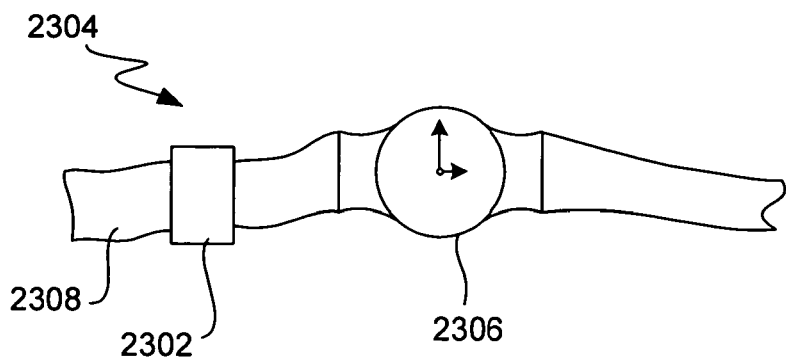
Figure 23C:
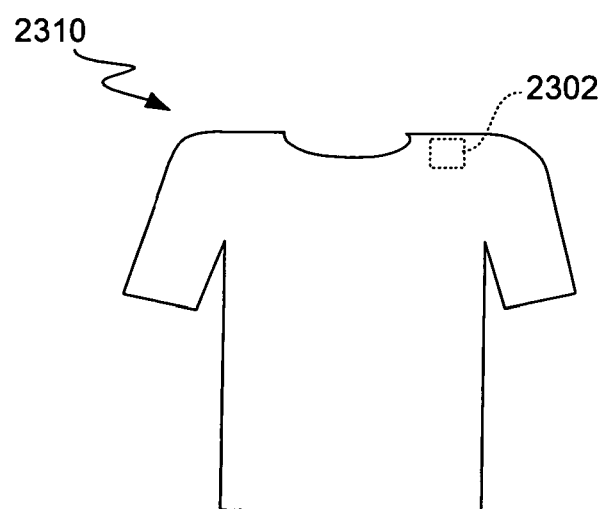
Figure 23D:
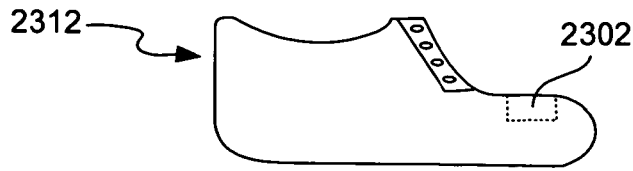
Figure 23E:
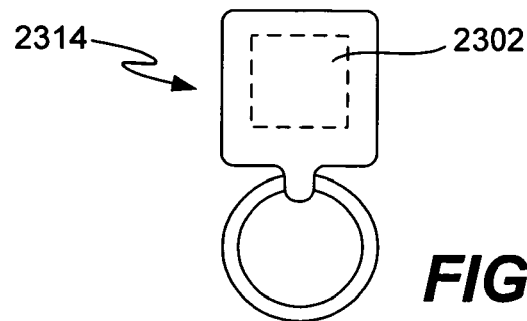
Figure 23F:
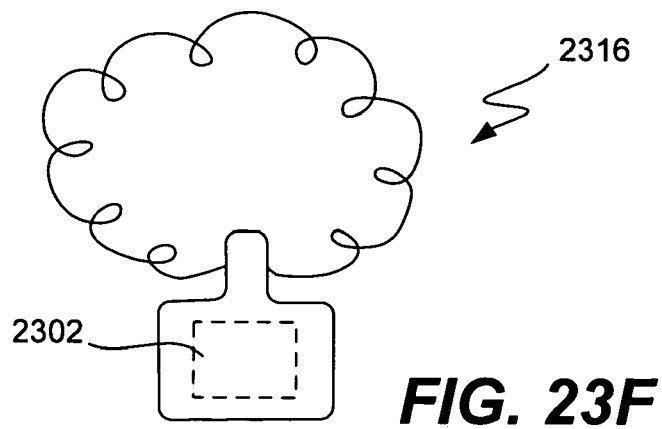
Figure 23G:
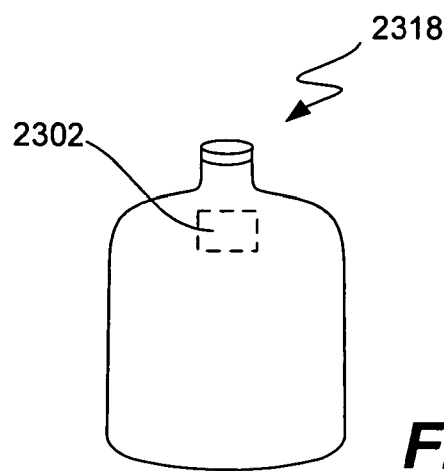

FIGS. 23A-23G illustrate examples of various end products having radiation monitoring capability. FIG. 23A illustrates a hat 2300 having a radiation monitoring system 2302. The radiation monitoring system 2302 can be attached to or embedded within the hat 2300. FIG. 23B illustrates a watch 2304 having a radiation monitoring system 2302. The watch 2304 can have a base 2306 and a band 2308. The radiation monitoring system 2302 can be coupled to the band 2308 as illustrated in FIG. 23B. Alternatively, the radiation monitoring system 2302 can be coupled to the base 2306. FIG. 23C illustrates a shirt 2310 having a radiation monitoring system 2302. As shown in FIG. 23C, in one embodiment, the radiation monitoring system 2302 can be placed in the upper, chest, back or shoulder region of the shirt 2310. FIG. 23D illustrates a shoe 2312 having a radiation monitoring system 2302. The radiation monitoring system 2302 can, for example, be placed at the top, upper portion of the shoe 2312. FIG. 23E illustrates a key chain 2314 having a radiation monitoring system 2302. FIG. 23F illustrates a bracelet or necklace 2316 having a radiation monitoring system 2302. FIG. 23G illustrates a bottle or tube 2318 having a radiation monitoring system 2302.

If the end product is soft or made of cloth (e.g., clothing, purse, hat, etc.), then the radiation monitoring system (e.g., provided as a module) can be sewn onto the cloth or adhered to the cloth using an adhesive (e.g., adhesive tape). The module, or a case for the module, can have thin flanges about its periphery which can be easily sewn onto the cloth. The case for the radiation monitoring system can be molded into its desired shape (e.g., injection molded, compression molded or vacu-formed). The case can be soft (vinyl, thin polypropylene, soft polyurethane, or PET). Typically, if flanges are utilized for sewing, they would be thin and soft. Alternatively, the case can be hard (e.g., PVC, polypropylene, nylon, polycarbonate, or styrene). If the end product is hard, the case can also be hard.

When the end product is a container, such as the bottle or tube 2318 shown in FIG. 23G, the radiation monitoring system 2302 can be attached to the bottle or tube 2318 or can be molded into the bottle or tube 2318. In one embodiment, the bottle or tube 2318 is a plastic container. The radiation monitoring system 2302 is particularly well suited to be attached or integral with a bottle or tube, often plastic, that contains sun tan lotion. Sun tan lotion includes sun tan or sun block lotions, including sun tan or sun block oils.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

The invention can be implemented in software, hardware or a combination of hardware and software. A number of embodiments of the invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield one or more of the following advantages. One advantage of the invention is that radiation monitoring can be inconspicuously performed in conjunction with eyewear. Another advantage of the invention is that electrical components for radiation monitoring can be embedded within a frame (e.g., temple) of eyewear. Still another advantage of the invention is that radiation monitoring can be intelligently performed such that it operates only at likely appropriate times to improve accuracy and usefulness. Yet another advantage of the invention is that eyewear may further include one or more auxiliary sensors that can cause additional output to be provided to the user.

Numerous specific details are set forth in order to provide a thorough understanding of the invention. However, it will be understood by those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

In the foregoing description, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

The many features and advantages of the invention are apparent from the written description and, thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. Eyewear, comprising:
   a supporting structure for the eyewear, the supporting structure including at least a forward portion;
   an optical detector, at least partially internal to the forward portion of the supporting structure, to capture data;
   an electronic circuit at least partially within the forward portion of the supporting structure and electrically connected to the optical detector, the electronic circuit configured to determine data based at least in part on at least the data captured by the optical detector;
   a wireless communication module operable to transmit or receive data from or to the eyewear in a wireless manner, the wireless communication device being at least partially within the forward portion of the supporting structure;
   a controller operatively connected to the electronic circuit and the wireless communication module, the controller configured to control an operation of the eyewear, and the controller being at least partially within the forward portion of the supporting structure; and
   a circuit substrate provided internal to the forward portion of the supporting structure of the eyewear, the electronic circuit being coupled to the circuit substrate, and the optical detector being electrically connected to the electronic circuit.

2. Eyewear as recited in claim 1, wherein the eyewear comprises:
   a motion detector to capture motion data, the motion detector being an electrical component that is provided within the supporting frame.

3. Eyewear as recited in claim 1, wherein the forward portion of the supporting structure includes an opening and the optical detector is provided at least partially internal to the supporting structure but adjacent the opening so as to be exposed to an environment of the eyewear.

4. Eyewear as recited in claim 1, wherein the forward portion of the supporting structure includes at least one lens holder supporting at least one lens for which a user is able to look through when the eyewear is being worn.

5. Eyewear as recited in claim 1, wherein the eyewear comprises:
   a color liquid-crystal display (LCD) display, operatively connected to the circuit substrate, that a user is able to view while the eyewear is being worn.

6. Eyewear as recited in claim 1, wherein the eyewear comprises:
   at least one physical sensor to sense an attribute of a user of the eyewear.

7. Eyewear as recited in claim 6, wherein the controller is configured to determine an emotion of the user based on at least the attribute of the user being sensed by the at least one physical sensor.

8. Eyewear as recited in claim 6, wherein the controller is configured to determine a heart-beat of the user based on at least the attribute of the user being sensed by the at least one physical sensor.

9. Eyewear as recited in claim 1, wherein the eyewear further comprises:
   at least one infrared sensor to sense an attribute of a user of the eyewear, wherein the infrared sensor is directed towards the head of the user when the eyewear is being worn by the user.

10. Eyewear as recited in claim 1, wherein the eyewear comprises:
    at least one radiation emitter to direct radiation energy towards a user's head when the eyewear is being worn by the user; and
    at least one radiation detector to sense at least a portion of the radiation energy that is reflected from the user's head when the eyewear is being worn by the user.

11. Eyewear as recited in claim 10, wherein the radiation energy comprises infrared radiation.

12. Eyewear as recited in claim 1, wherein the eyewear comprises:
at least one wireless sensor configured to capture data, and wireless communication the data to the wireless communication module.

13. Eyewear, comprising:
a supporting structure for the eyewear, the supporting structure including at least a forward portion;
an optical detector, at least partially internal to the forward portion of the supporting structure, to capture data;
an electronic circuit at least partially within the forward portion of the supporting structure and electrically connected to the optical detector, the electronic circuit configured to determine data based at least in part on at least the data captured by the optical detector;
a data communication module operable to transmit or receive data from or to the eyewear in a wired and/or wireless manner, the data communication device being at least partially within the forward portion of the supporting structure;
a controller operatively connected to the electronic circuit and the data communication module, the controller configured to control an operation of the eyewear, and the controller being at least partially within the forward portion of the supporting structure; and
a circuit substrate provided internal to the forward portion of the supporting structure of the eyewear, the electronic circuit being coupled to the circuit substrate, and the optical detector being electrically connected to the electronic circuit.

14. Eyewear as recited in claim 13, wherein the eyewear comprises:
a color liquid-crystal display (LCD) display, operatively connected to the circuit substrate, that a user is able to view while the eyewear is being worn.

15. Eyewear as recited in claim 13, wherein the eyewear comprises:
a motion detector to capture motion data, the motion detector being an electrical component that is provided within the supporting frame.

16. Eyewear as recited in claim 13, wherein the eyewear comprises:
at least one electrical component tethered to the eyewear, the at least one electrical component tethered to the eyewear being electrically connected with the controller or the electronic circuit.

17. Eyewear as recited in claim 13, wherein the eyewear further comprises:
at least one sensor within the eyewear, the at least one sensor being electrically connected with the controller or the electronic circuit.

18. Eyewear as recited in claim 13, wherein the eyewear further comprises:
an infrared sensor configured to be directed towards the head of the user when the eyewear is being worn by the user.

19. Eyewear as recited in claim 13, wherein the eyewear comprises:
a photodiode configured to be directed towards the head of the user when the eyewear is being worn by the user, the photodiode being at least partially within the forward portion of the supporting structure.

20. Eyewear as recited in claim 13, wherein the eyewear comprises:
at least one radiation emitter to direct radiation energy towards a user's head when the eyewear is being worn by the user; and
at least one radiation detector to sense at least a portion of the radiation energy that is reflected from the user's head when the eyewear is being worn by the user.

21. Eyewear as recited in claim 20,
wherein the radiation detector comprises a photodiode, and
wherein the radiation emitter comprises a Light Emitting Diode (LED).

22. Eyewear as recited in claim 13, wherein the eyewear comprises:
a connector configured to facilitate a wired electrical interconnection with an external electrical device.

23. Eyewear as recited in claim 22, wherein the external electronic device is a computing device.

24. Eyewear as recited in claim 23, wherein the connector is electrically connected with the controller, the data communication module or the electronic circuit of the eyewear.

25. Eyewear as recited in claim 24, wherein the eyewear comprises:
a motion detector to capture motion data, the motion detector being an electrical component that is provided within the supporting frame; and
a sensor configured to be directed towards the head of the user when the eyewear is being worn by the user.

26. Eyewear as recited in claim 25, wherein the sensor comprises a photodiode, the photodiode being at least partially within the forward portion of the supporting structure.

27. Eyewear, comprising:
a supporting structure for the eyewear, the supporting structure including at least a forward portion;
at least one radiation emitter to direct radiation energy towards a user's head when the eyewear is being worn by the user; and
at least one radiation detector to sense at least a portion of the radiation energy that is reflected from the user's head when the eyewear is being worn by the user;
an electronic circuit at least partially within the forward portion of the supporting structure and electrically connected to the at least one radiation detector, the electronic circuit configured to determine data based at least in part on at least the data captured by the radiation detector;
a data communication module operable to transmit or receive data from or to the eyewear in a wired and/or wireless manner, the data communication device being at least partially within the forward portion of the supporting structure;
a controller operatively connected to the electronic circuit and the data communication module, the controller configured to control an operation of the eyewear, and the controller being at least partially within the forward portion of the supporting structure; and
a circuit substrate provided internal to the forward portion of the supporting structure of the eyewear, the electronic circuit being coupled to the circuit substrate, and the radiation detector being electrically connected to the electronic circuit.

28. Eyewear as recited in claim 27, wherein the eyewear comprises:
a motion detector to capture motion data, the motion detector being an electrical component that is provided within the supporting frame.

29. Eyewear as recited in claim 27, wherein the radiation energy comprises infrared radiation.

30. Eyewear as recited in claim 27, wherein the forward portion of the supporting structure includes at least one lens holder supporting at least one lens for which a user is able to look through when the eyewear is being worn.

31. Eyewear as recited in claim 27, wherein the eyewear comprises:
a color liquid-crystal display (LCD) display, operatively connected to the circuit substrate, that a user is able to view while the eyewear is being worn.

32. Eyewear as recited in claim 27, wherein the eyewear comprises:
at least one physical sensor to sense an attribute of a user of the eyewear.

33. Eyewear as recited in claim 32, wherein the controller is configured to determine an emotion of the user based on at least the attribute of the user being sensed by the at least one physical sensor.

34. Eyewear as recited in claim 32, wherein the controller is configured to determine a heart-beat of the user based on at least the attribute of the user being sensed by the at least one physical sensor.

35. Eyewear as recited in claim 27, wherein the eyewear comprises:
at least one wireless sensor configured to capture data, and wireless communication the data to the wireless communication module.

36. Eyewear as recited in claim 27, wherein the eyewear comprises:
at least one electrical component tethered to the eyewear, the at least one electrical component tethered to the eyewear being electrically connected with the controller.

37. Eyewear as recited in claim 36, wherein the at least one electrical component tethered to the supporting structure is tethered to the supporting structure via at least a strap.

38. Eyewear as recited in claim 37, wherein the at least one electrical component tethered to the supporting structure is a battery.

39. Eyewear as recited in claim 27, wherein the eyewear comprises:
at least one sensor within the eyewear, the at least one sensor being electrically connected with the controller.

40. Eyewear as recited in claim 39, wherein the at least one sensor, alone or with at least the controller, is configured to determine velocity of movement of the eyewear.

41. Eyewear as recited in claim 39, wherein the at least one sensor, alone or with at least the controller, is configured to determine distance traveled by the eyewear.

42. Eyewear as recited in claim 41, wherein the distance traveled includes at least an elevation amount traveled.

43. Eyewear as recited in claim 27, wherein the at least one sensor, alone or with at least the controller, is configured to determine an activity level carried out by a user of the eyewear.

44. Eyewear as recited in claim 27,
wherein the radiation detector comprises a photodiode, and
wherein the radiation emitter comprises a Light Emitting Diode (LED).

45. Eyewear as recited in claim 27, wherein the eyewear comprises:
an optical detector, at least partially internal to the forward portion of the supporting structure, to capture data,
wherein the forward portion of the supporting structure includes an opening and the optical detector is provided at least partially internal to the supporting structure but adjacent the opening so as to be exposed to an environment of the eyewear.

46. Eyewear as recited in claim 27, wherein the eyewear comprises:
a light sensor within the eyewear, the light sensor being electrically connected with the controller or the electronic circuit.

* * * * *